United States Patent
Finlay

(10) Patent No.: US 10,683,350 B2
(45) Date of Patent: Jun. 16, 2020

(54) ANTI-CD47 ANTIBODY MOLECULES

(71) Applicant: ULTRAHUMAN FOUR LIMITED, Sandwich (GB)

(72) Inventor: William James Jonathan Finlay, Sandwich (GB)

(73) Assignee: ULTRAHUMAN FOUR LIMITED, Sandwich (GB)

(*) Notice: Subject to any disclaimer, the term of this patent is extended or adjusted under 35 U.S.C. 154(b) by 0 days.

(21) Appl. No.: 16/543,884

(22) Filed: Aug. 19, 2019

(65) Prior Publication Data

US 2019/0375840 A1 Dec. 12, 2019

Related U.S. Application Data

(63) Continuation of application No. PCT/GB2018/052347, filed on Aug. 17, 2018.

(30) Foreign Application Priority Data

Aug. 18, 2017 (GB) .................................. 1713298.6
Feb. 16, 2018 (GB) .................................. 1802595.7
May 24, 2018 (GB) .................................. 1808570.4

(51) Int. Cl.
  *C07K 16/28* (2006.01)
  *C07K 16/30* (2006.01)
  (Continued)

(52) U.S. Cl.
  CPC .......... *C07K 16/2803* (2013.01); *A61P 35/00* (2018.01); *A61K 39/39558* (2013.01);
  (Continued)

(58) Field of Classification Search
  None
  See application file for complete search history.

(56) References Cited

U.S. PATENT DOCUMENTS 9,221,908 B2 * 12/2015 Frazier ............... C07K 16/2803
9,518,117 B2 * 12/2016 Frazier ............... C07K 16/2803
(Continued)

FOREIGN PATENT DOCUMENTS

WO  WO 2011/143624 A2   11/2011
WO  WO 2013/119714 A1   8/2013
(Continued)

OTHER PUBLICATIONS

International Search Report and Written Opinion dated Dec. 17, 2018 for International Application No. PCT/GB2018/052347, 19 pages.
(Continued)

*Primary Examiner* — Claire Kaufman
(74) *Attorney, Agent, or Firm* — Cooley LLP; Ivor R. Elrifi

(57) ABSTRACT

The invention relates to antibody molecules and antigen-binding portions thereof which bind specifically to CD47 (Cluster of Differentiation 47, also known as integrin associated protein [IAP]). In aspects of the invention, the anti-CD47 antibody molecules and antigen-binding portions thereof specifically bind to human CD47 and cynomolgus monkey CD47. Medical uses of the anti-CD47 antibody molecules and antigen-binding portions of the invention are disclosed. The anti-CD47 antibody molecules and antigen-binding portions of the invention represent modified and optimised binding molecules compared with a VxP037 murine/humanized anti-CD47 antibody described in WO2014/093678A2.

10 Claims, 23 Drawing Sheets

Specification includes a Sequence Listing.

(51) Int. Cl.
*A61P 35/00* (2006.01)
*A61K 39/395* (2006.01)

(52) U.S. Cl.
CPC ...... *C07K 2317/21* (2013.01); *C07K 2317/24* (2013.01); *C07K 2317/33* (2013.01); *C07K 2317/565* (2013.01); *C07K 2317/76* (2013.01)

(56) References Cited

U.S. PATENT DOCUMENTS

| 10,259,873 | B2* | 4/2019 | Frazier | C07K 16/2803 |
| 2014/0140989 | A1 | 5/2014 | Eckelman et al. | |
| 2017/0073395 | A1 | 3/2017 | Finlay et al. | |

FOREIGN PATENT DOCUMENTS

| WO | WO 2014/093678 A2 | 6/2014 |
| WO | WO 2015/191861 A1 | 12/2015 |
| WO | WO 2016/081423 A1 | 5/2016 |
| WO | WO 2016/109415 A1 | 7/2016 |
| WO | WO 2017/049251 A2 | 3/2017 |
| WO | WO 2017/121771 A1 | 7/2017 |
| WO | WO 2019/185717 A1 | 10/2019 |

OTHER PUBLICATIONS

UKIPO Search Report dated May 23, 2018 for GB Application No. GB1713298.6, 1 page.
Ahmadi, M. et al., "Small Amounts of Sub-Visible Aggregates Enhance the Immunogenic Potential of Monoclonal Antibody Therapeutics," Pharm Res, 32:1383 (2005); https://doi.org/10.1007/s11095-014-1541-x, 12 pages.
Almagro, J. C. & Fransson, J., "Humanization of antibodies," Frontiers in Bioscience, 13:1619-1633 (2008).
Bagshawe, K. D. et al., "Antibody-Enzyme Conjugates Can Generate Cytotoxic Drugs from Inactive Precursors at Tumor Sites," Antibody, Immunoconjugates, and Radiopharmaceuticals, 4(4):915-922 (1991).
Fennell, B. J. et al., "CDR-restricted engineering of native human scFvs creates highly stable and soluble bifunctional antibodies for subcutaneous delivery," mAbs, 5(6):882-895 (2013).
Finlay, W. J. et al., "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," J. Mol. Biol., 388:541-558 (2009).
Finlay, W. J. J. et al., "Optimized Generation of High-Affinity, High-Specificity Single-Chain Fv Antibodies from Multiantigen Immunized Chickens," Dermot Walls and Sinéad T. Loughran (eds.), Protein Chromatography: Methods and Protocols, Methods in Molecular Biology, vol. 681; doi:10.1007/978-1-60761-913-0_21, 19 pages, (2011).

Harding, F. A. et al., "The immunogenicity of humanized and fully human antibodies. Residual immunogenicity resides in the CDR regions," mAbs, 2(3):256-265 (2010).
Henikoff, S. & Henikoff, J. G., "Amino acid substitution matrices from protein blocks," Proc. Natl. Acad. Sci. USA, 89:10915-10919 (1992).
Holliger, P. & Hudson, P. J., "Engineered antibody fragments and the rise of single domains," Nature Biotechnology, 23(9):1126-1136 (2005).
Hwang, W. Y. K. & Foote, J., "Immunogenicity of engineered antibodies," Methods, 36:3-10 (2005).
Jones, P. T. et al., "Replacing the complementarity-determining regions in a human antibody with those from a mouse," Nature, 321:522-525 (1986).
Ledermann, J. A. et al., "A Phase-I Study of Repeated Therapy with Radiolabelled Antibody to Carcinoembryonic Antigen Using Intermittent or Continuous Administration of Cyclosporin A to Suppress the Immune Response," Int. J. Cancer, 47:659-664 (1991).
Melero, I. et al., "Agonist Antibodies to TNFR Molecules That Costimulate T and NK Cells," Clin Cancer Res, 19(5):1044-1053 (2013), and Correction, 1 page.
Mouquet, H. et al., "Polyreactivity increases the apparent affinity of anti-HIV antibodies by heteroligation," Nature, 467(7315):591-595 (2010); doi:10.1038/nature09385.
Nelson, A. L. et al., "Development trends for human monoclonal antibody therapeutics," Nature Reviews Drug Discovery, 9:767-774 (2010).
North, B. et al., "A New Clustering of Antibody CDR Loop Conformations," J. Mol. Biol. (2010); doi:10.1016/j.jmb.2010.10.030, 29 pages.
Swindells, M. B. et al., "abYsis: Integrated Antibody Sequence and Structure—Management, Analysis, and Prediction," J. Mol. Biol., 429:356-364 (2017).
Tiller, T. et al., "A fully synthetic human Fab antibody library based on fixed VH/VL framework pairings with favorable biophysical properties," mAbs, 5:3:1-26 (2013).
Townsend, S. et al., "Augmented Binary Substitution: Single-pass CDR germ-lining and stabilization of therapeutic antibodies," PNAS, 112(50):15354-15359 (2015).
Tu, C. et al., "Combination of Structural and Empirical Analyses Delineates the Key Contacts Mediating Stability and Affinity Increases in an Optimized Biotherapeutic Single-chain Fv (ScFv)," The Journal of Biological Chemistry, 291(3):1267-1276 (2016).
Van Aerts, L. Agjm et al., "Biosimilars entering the clinic without animal studies," mAbs, 6(5):1155-1162 (2014).
Van Meer, P. J. K. et al., "Immunogenicity of mAbs in non-human primates during nonclinical safety assessment," mAbs, 5(5):810-816 (2013).
Zhou, F. et al., "A general user interface for prediction servers of proteins' post-translational modification sites," Nature Protocols, 1(3):1318-1321 (2006).

\* cited by examiner

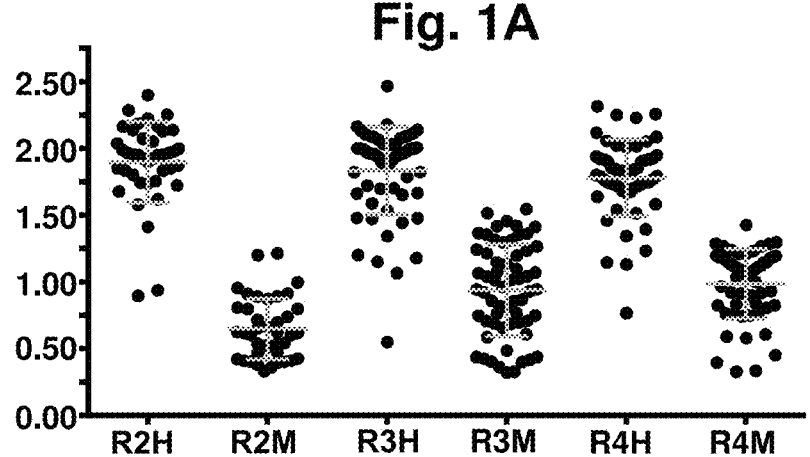
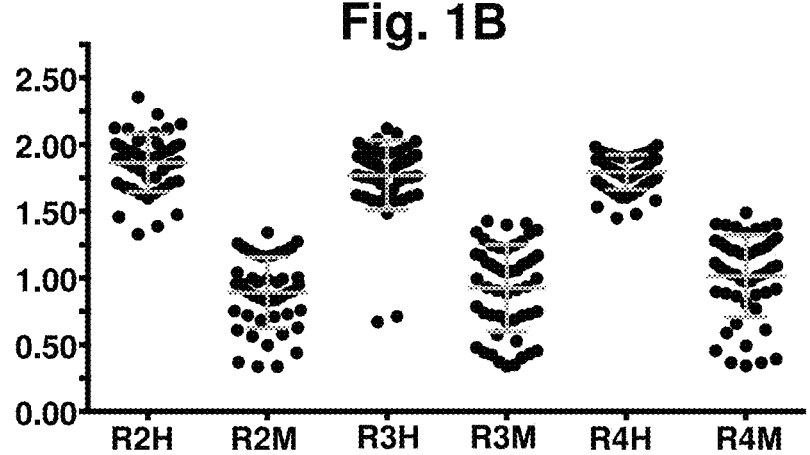
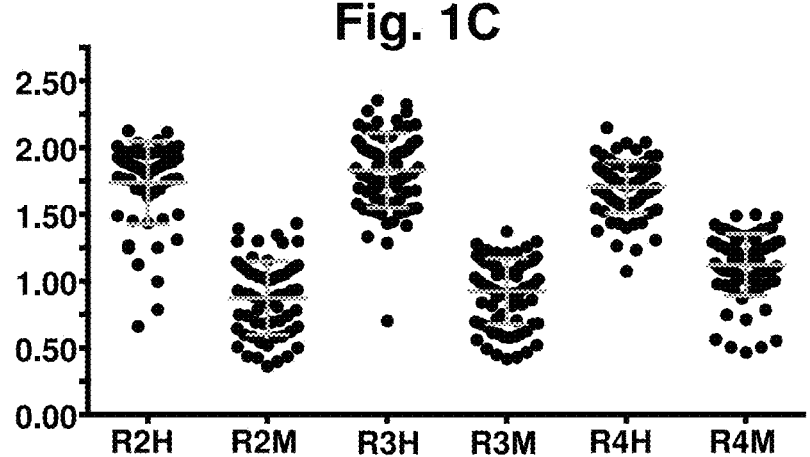

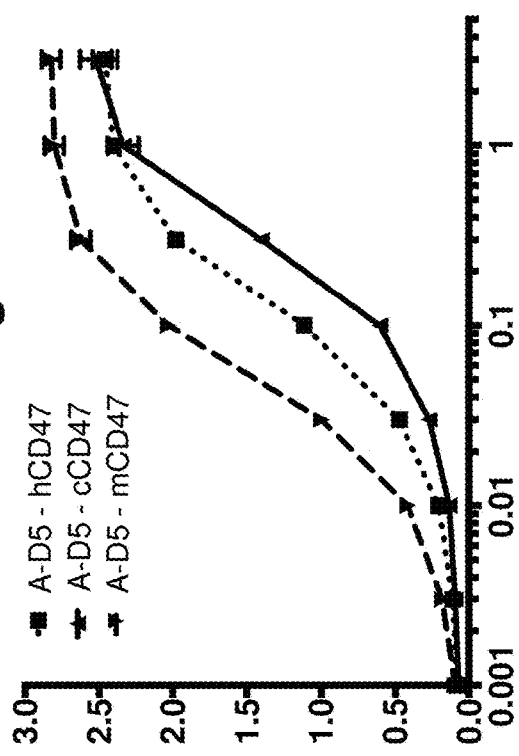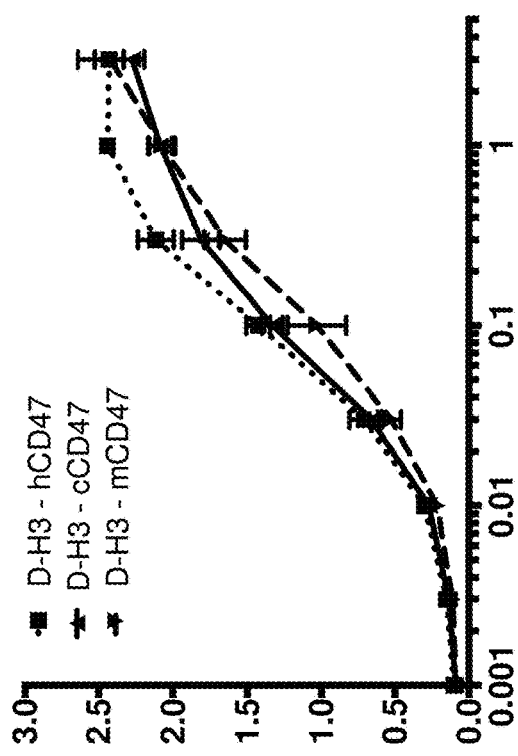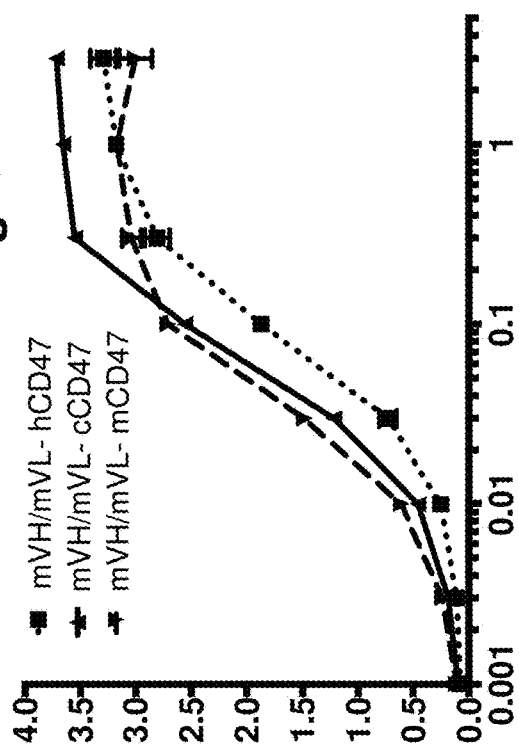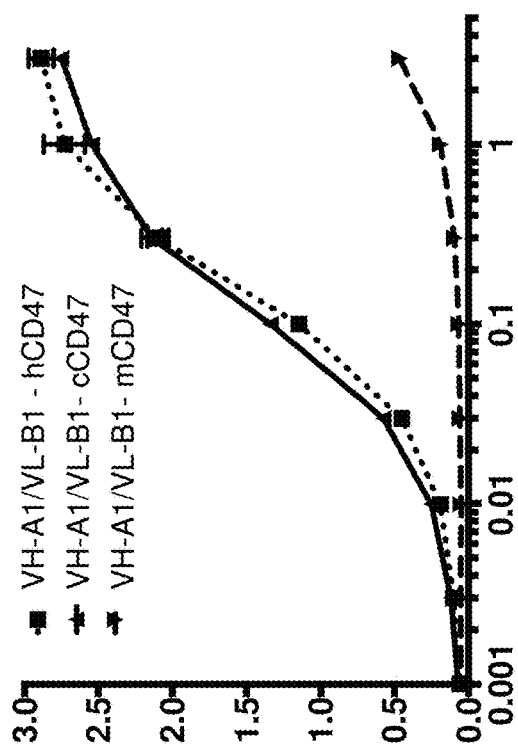

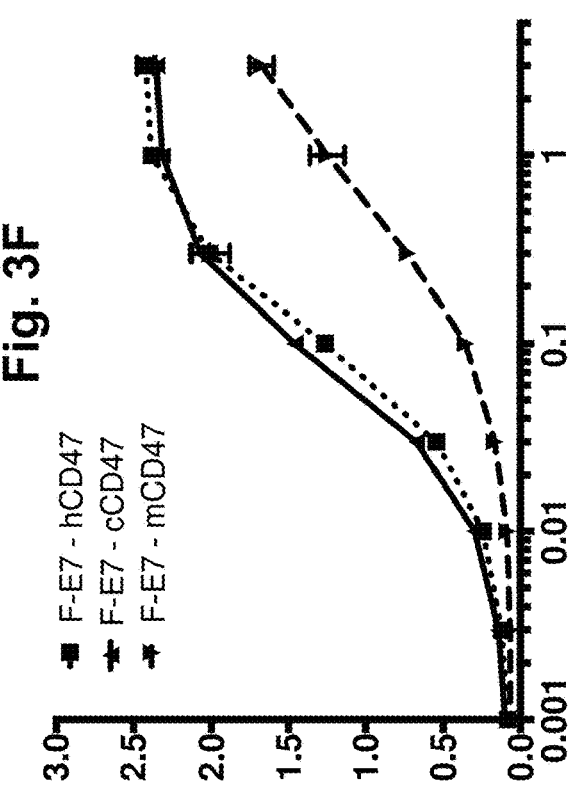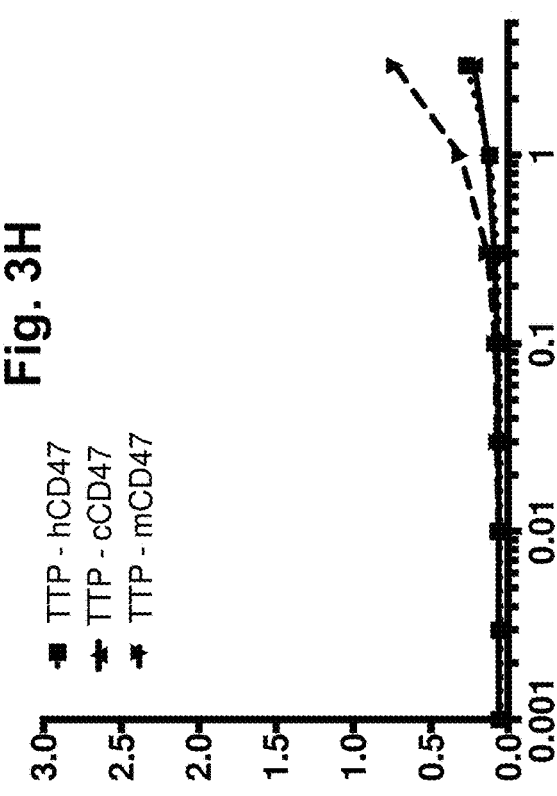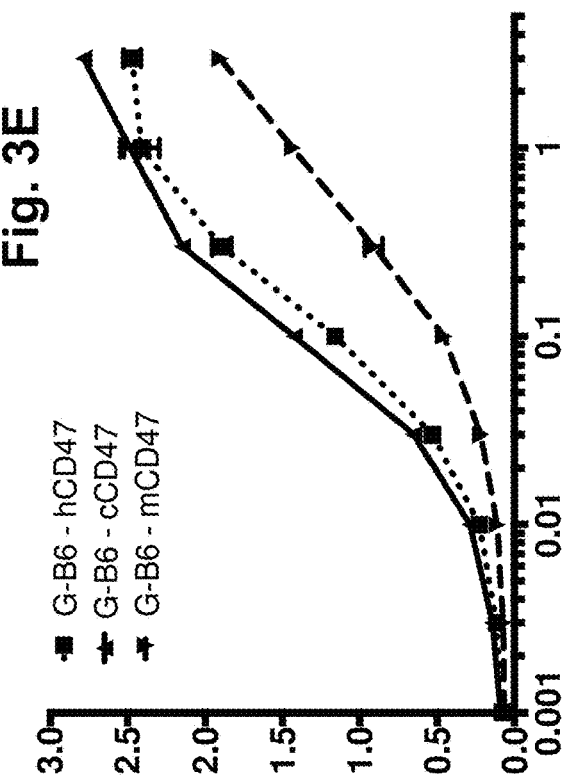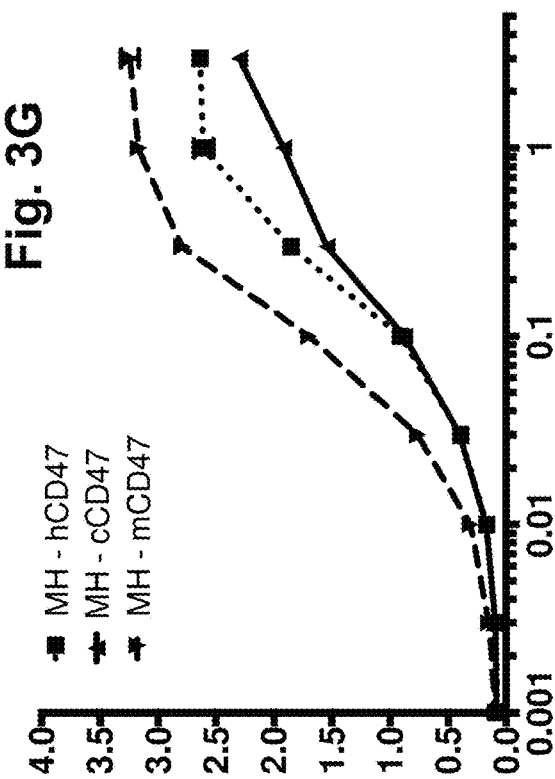

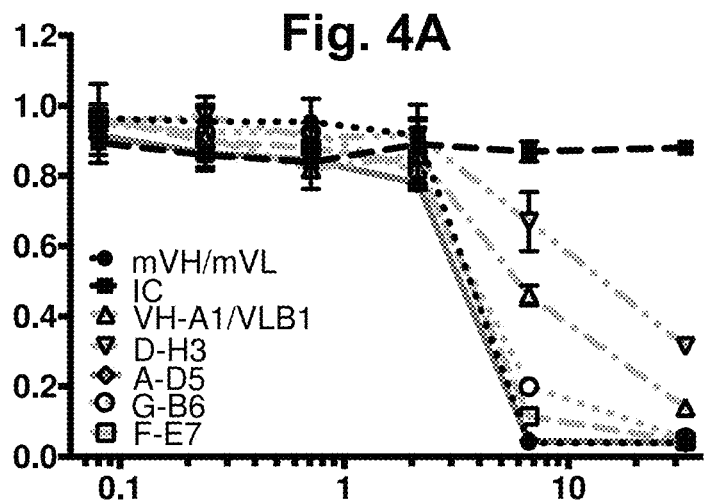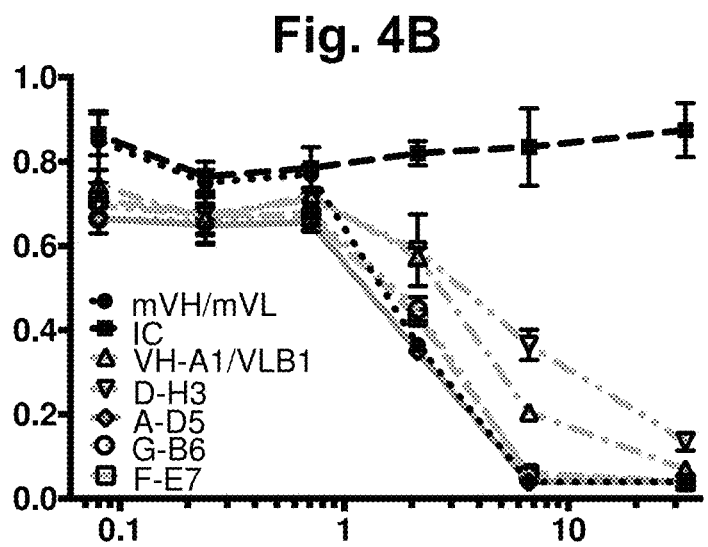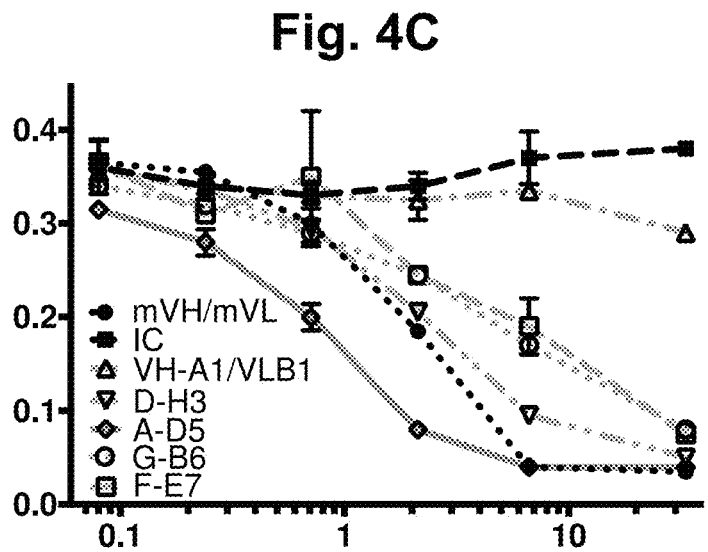

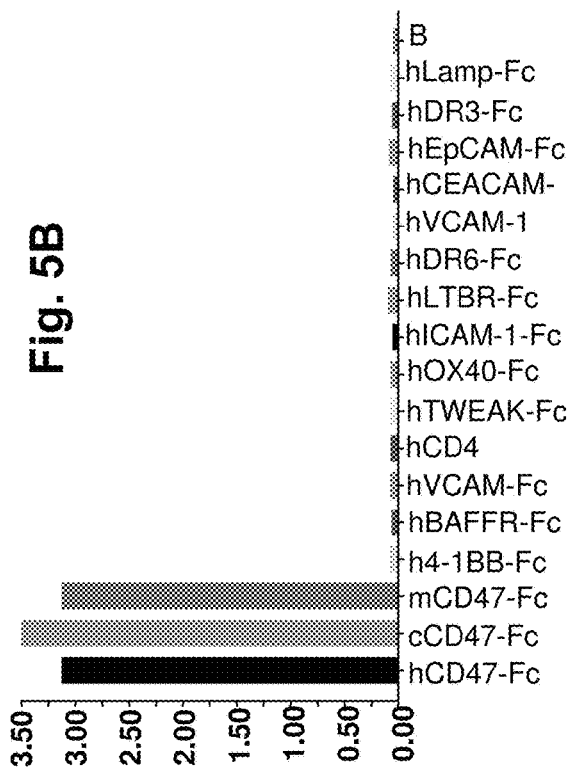
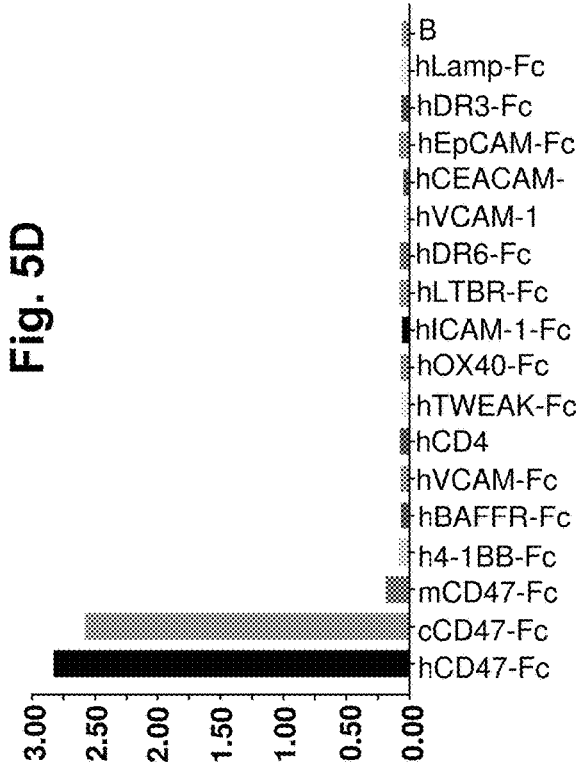
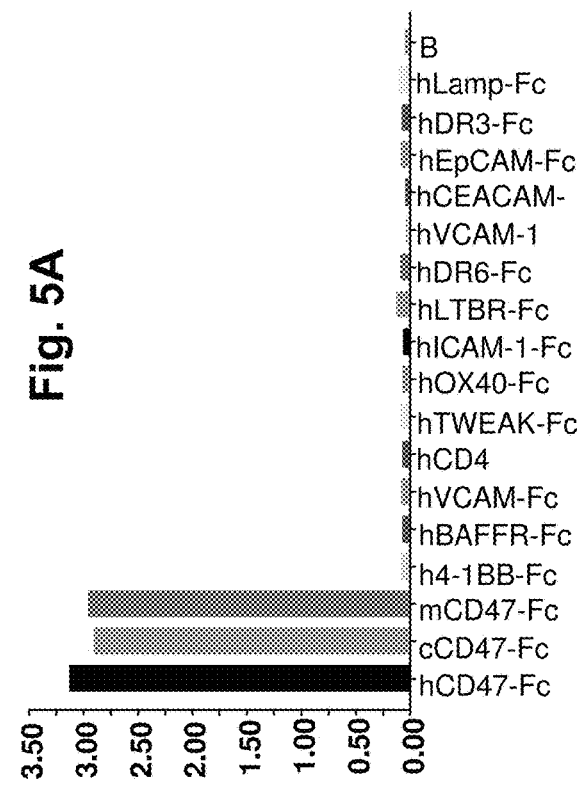
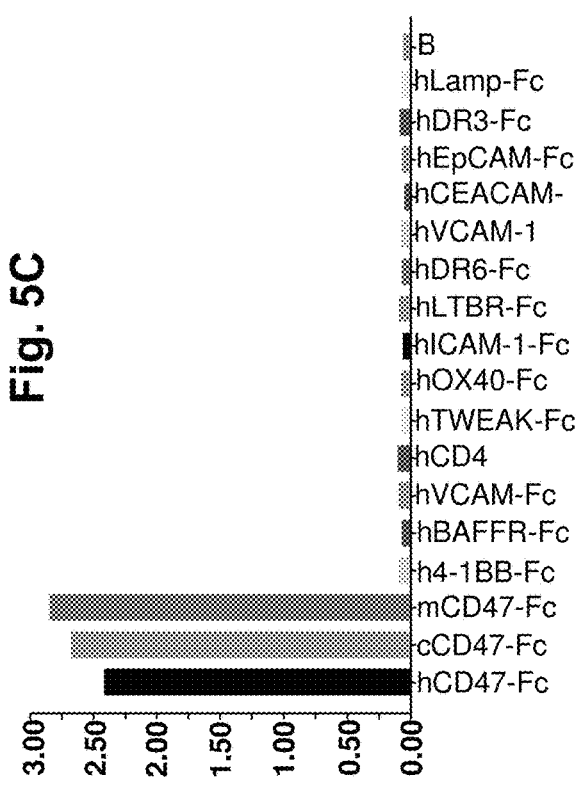

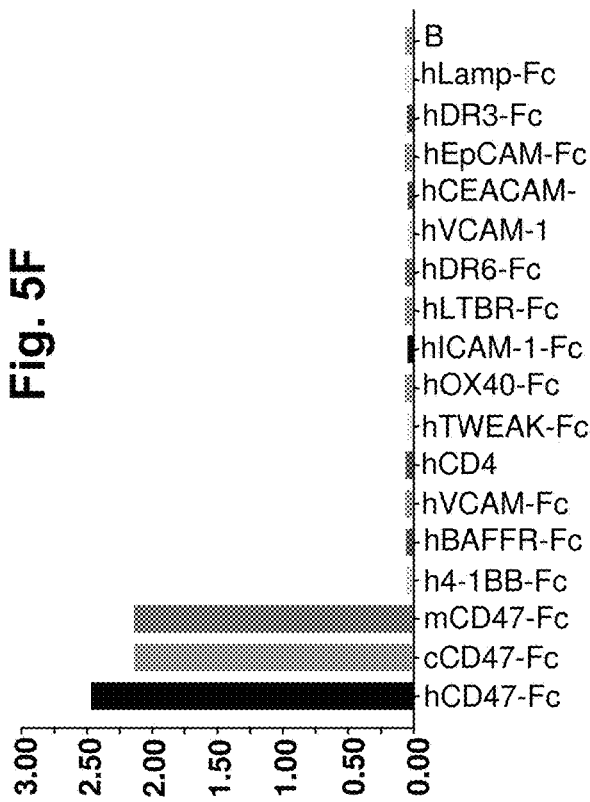
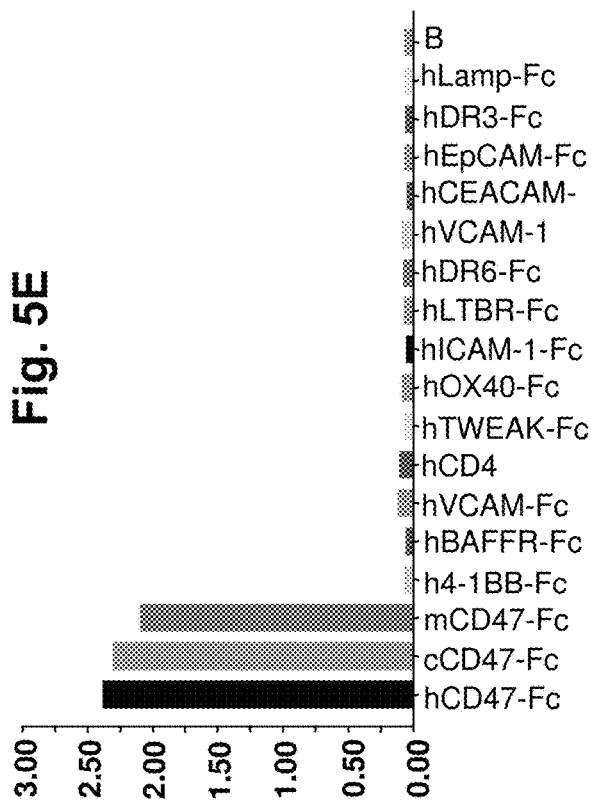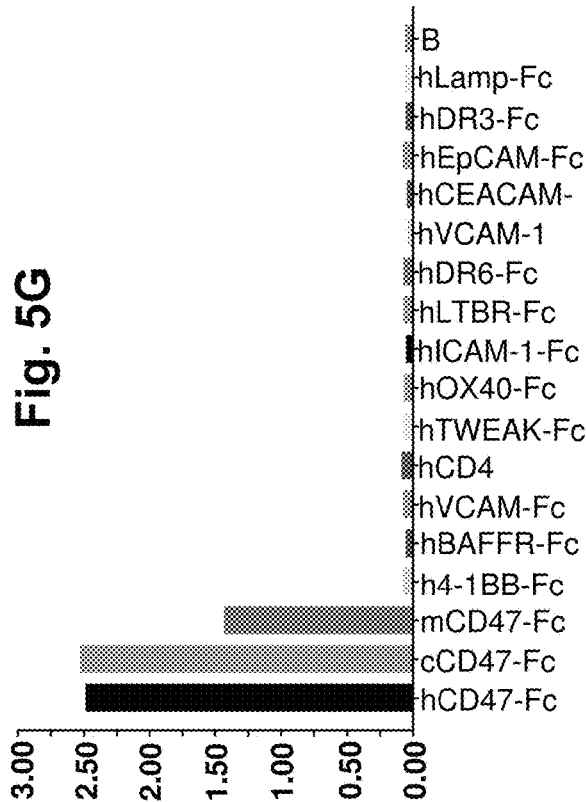

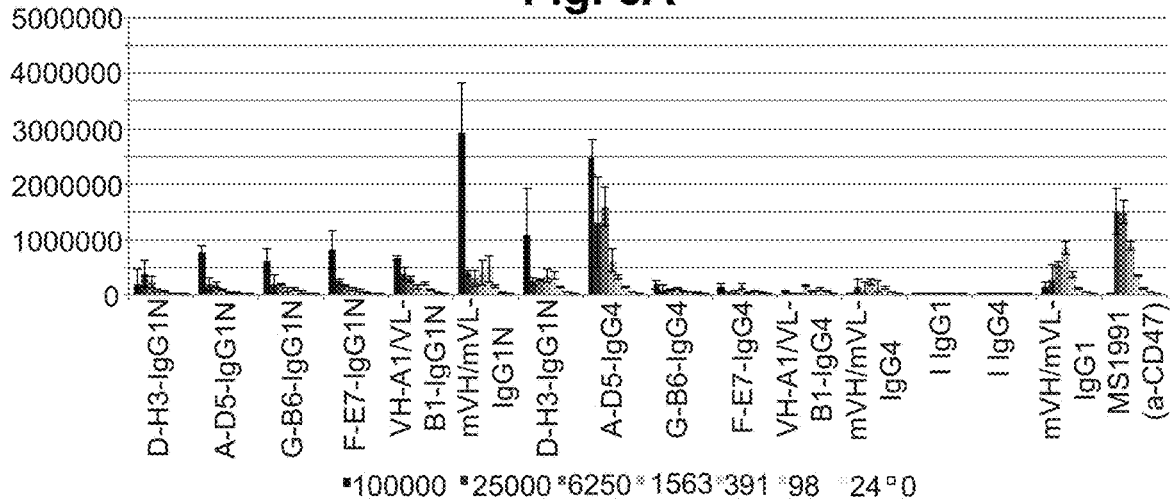
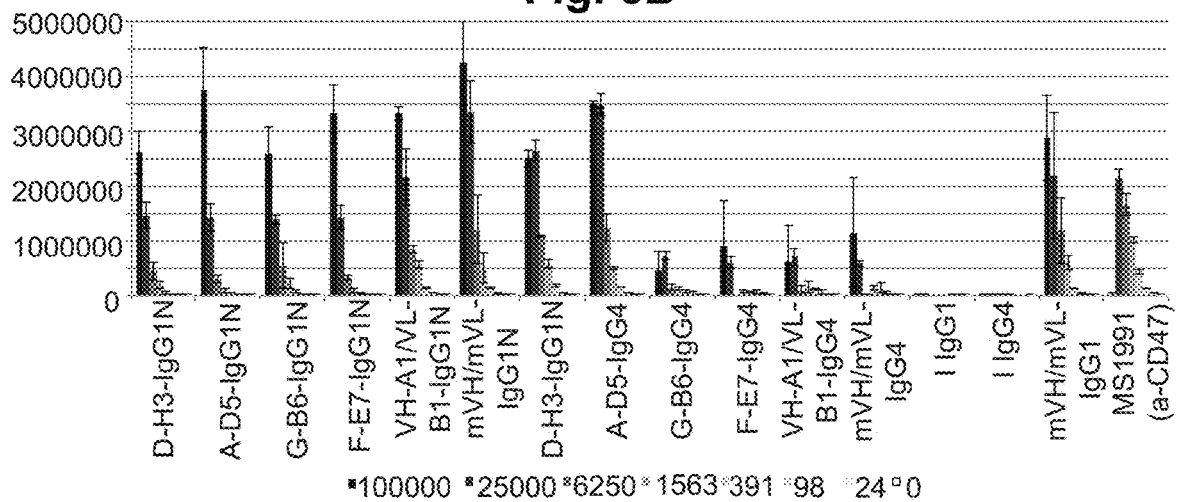
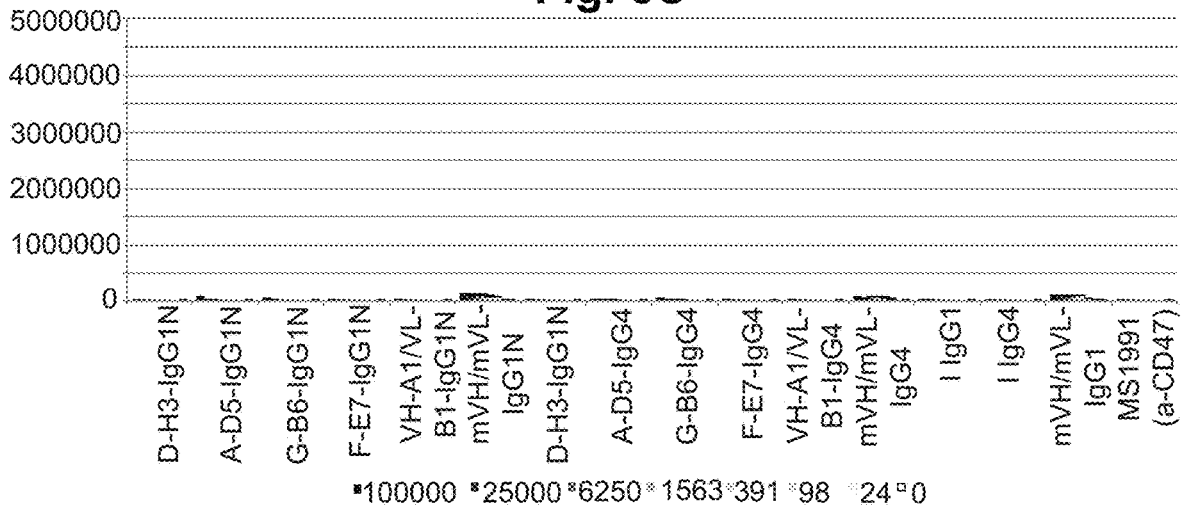

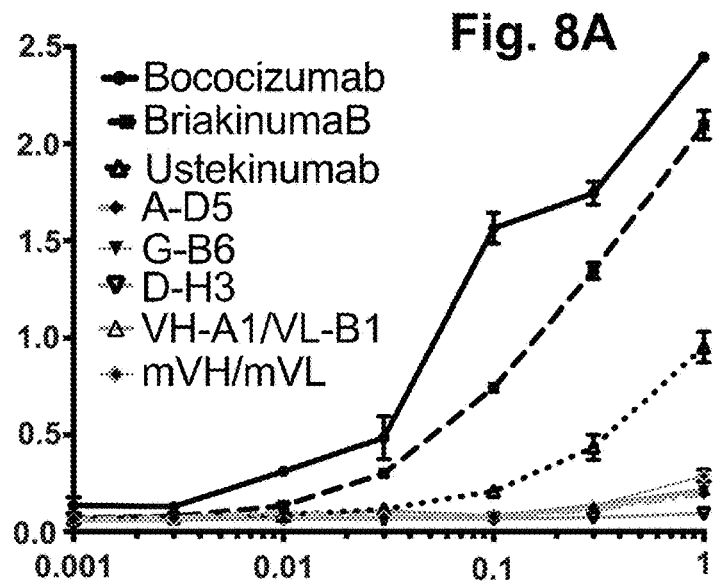
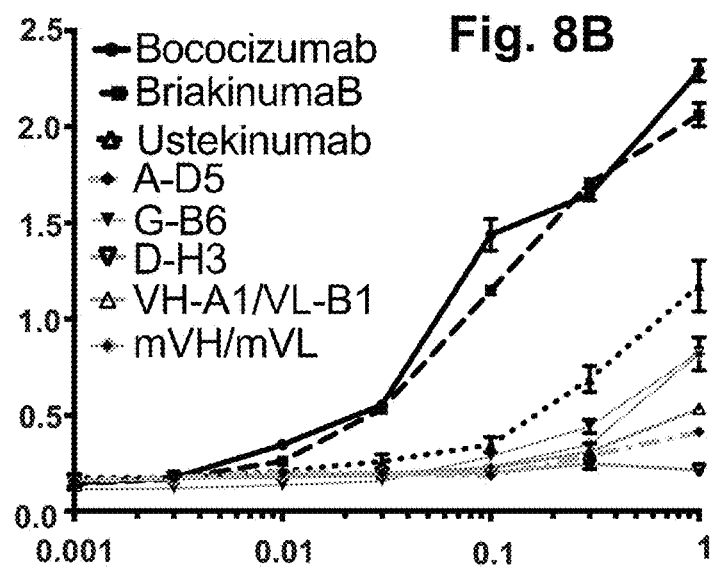
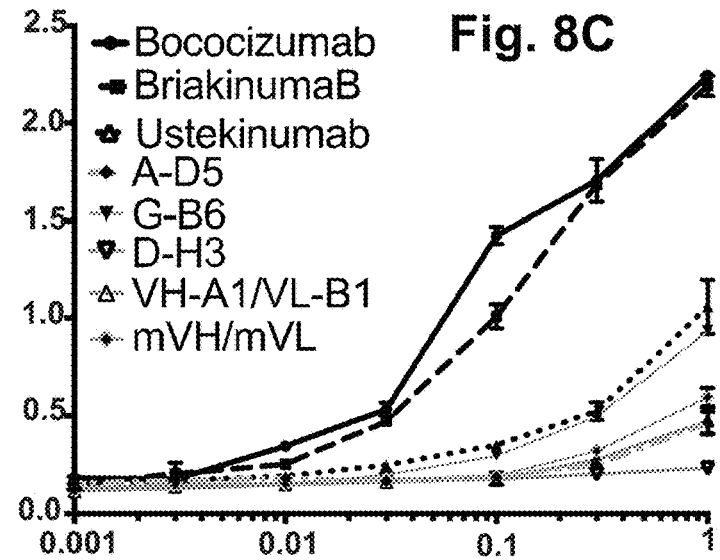

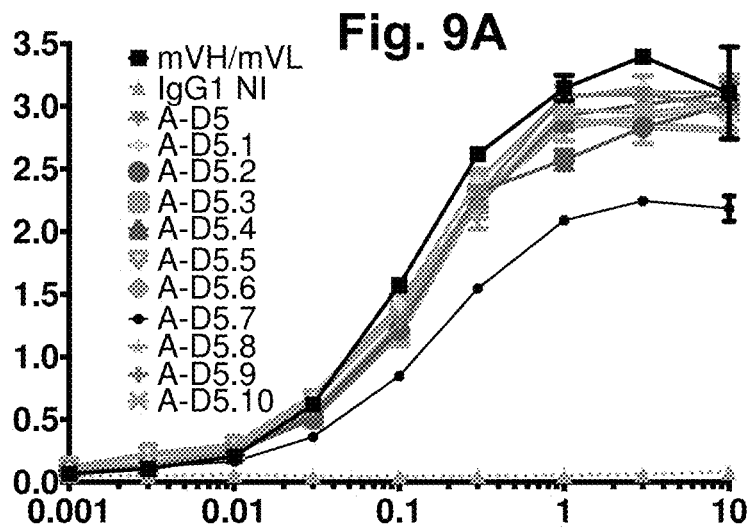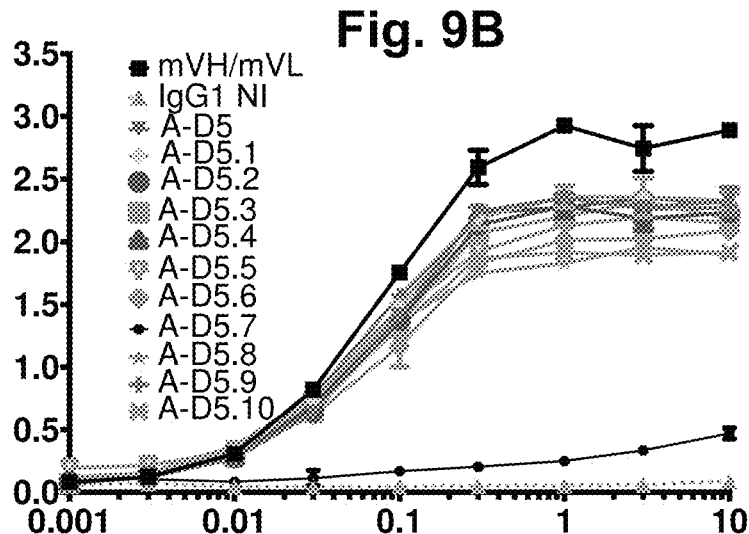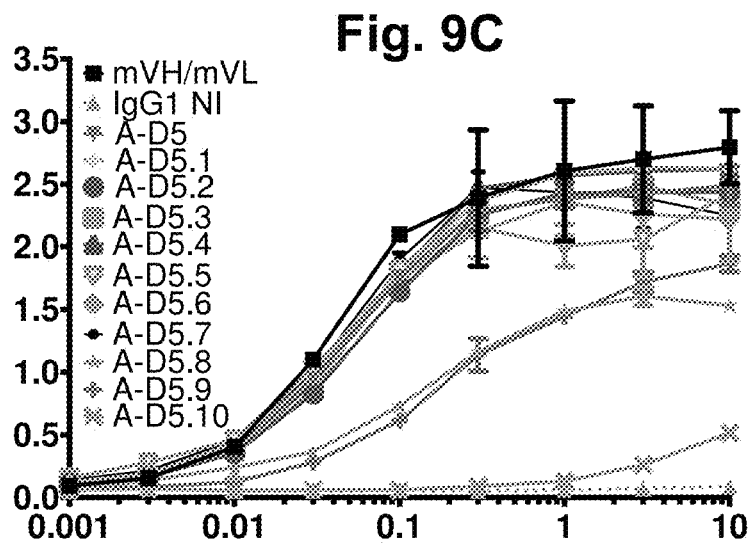

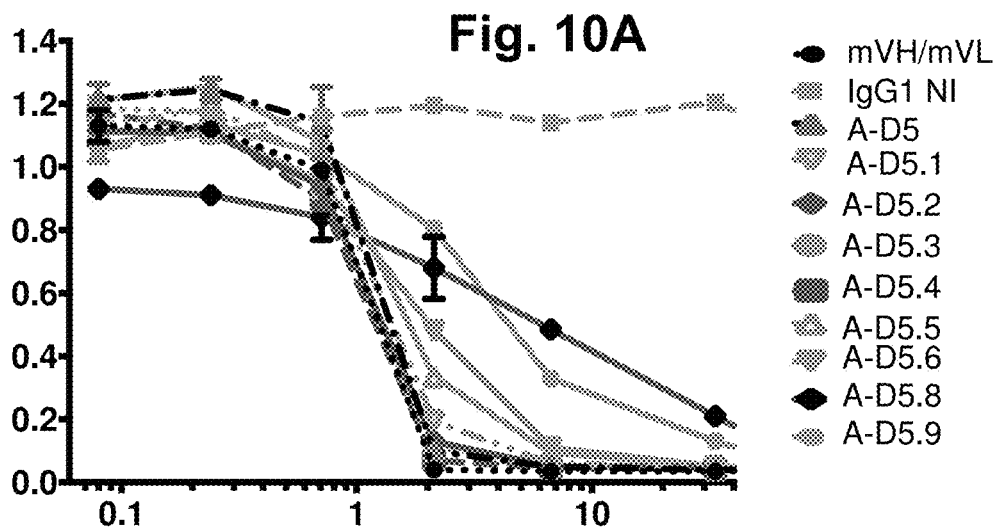
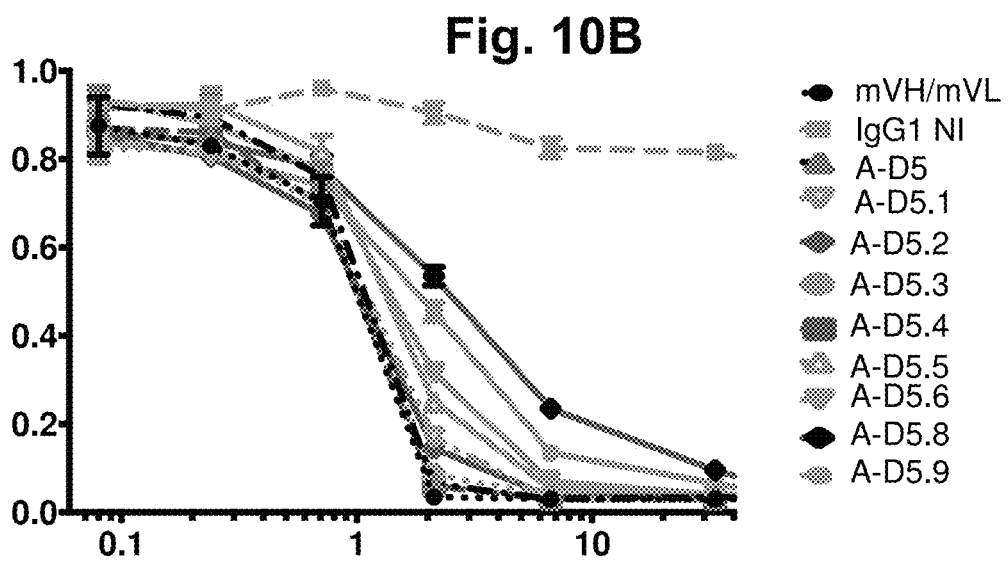
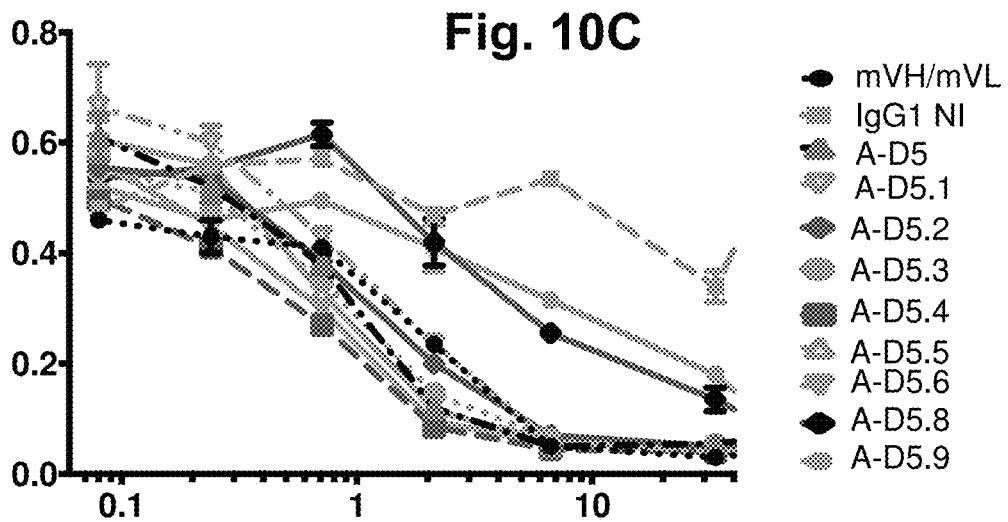

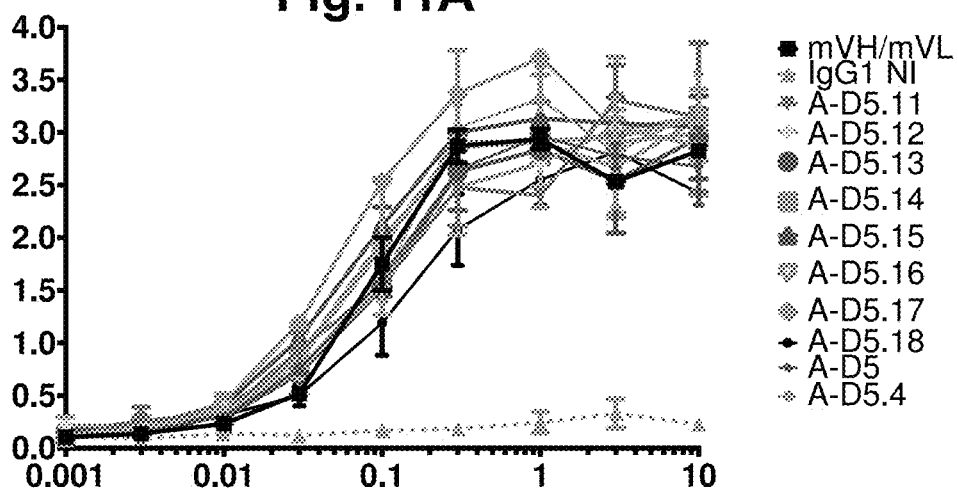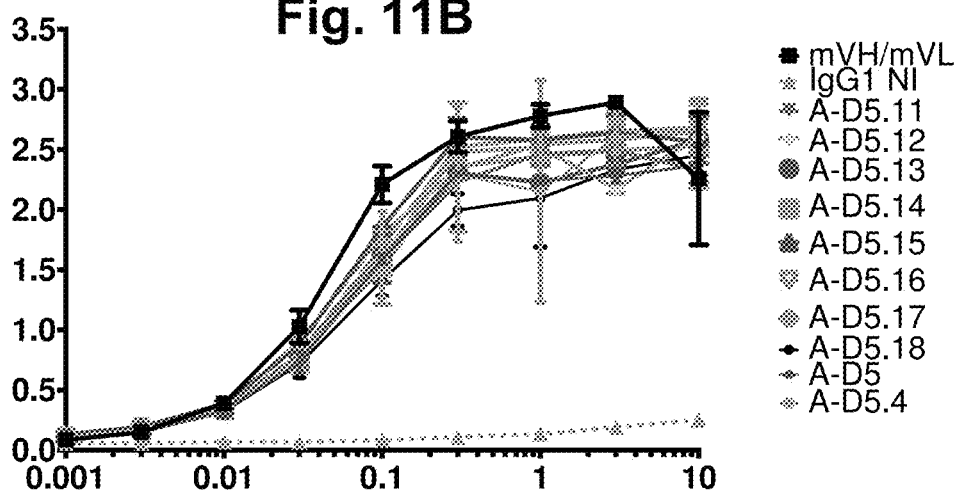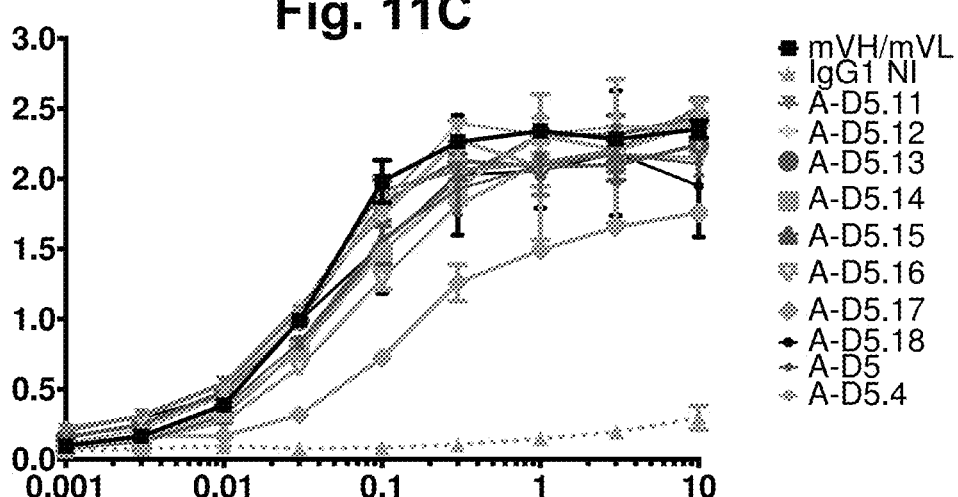

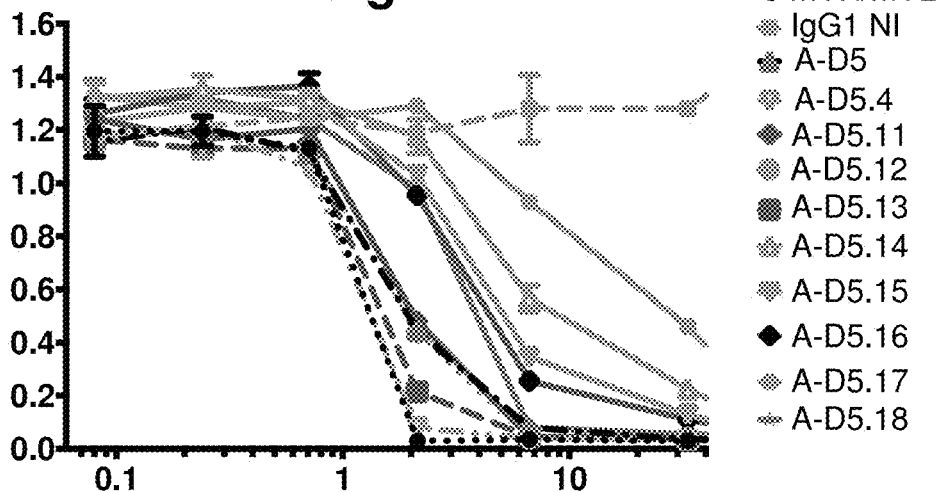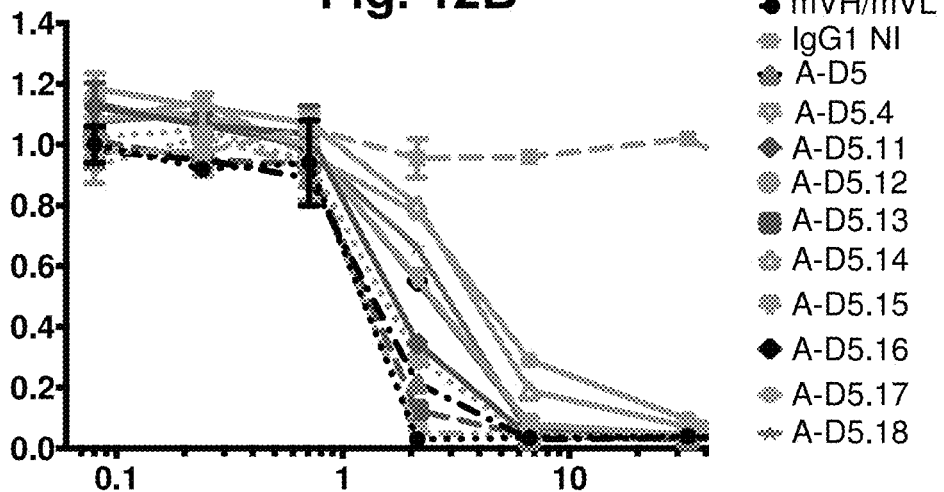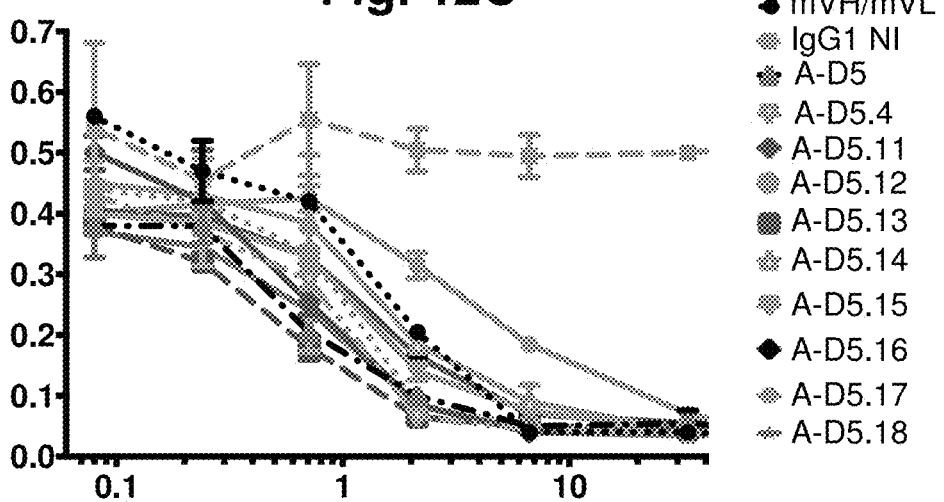

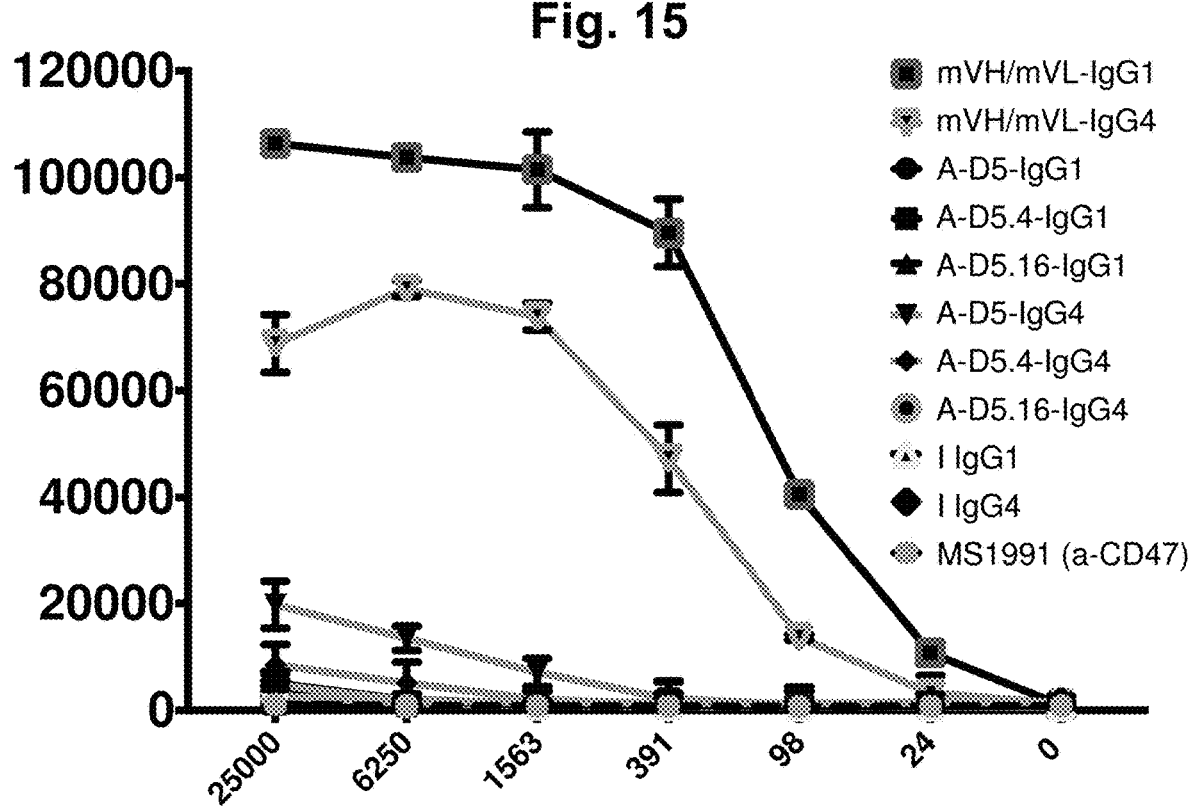

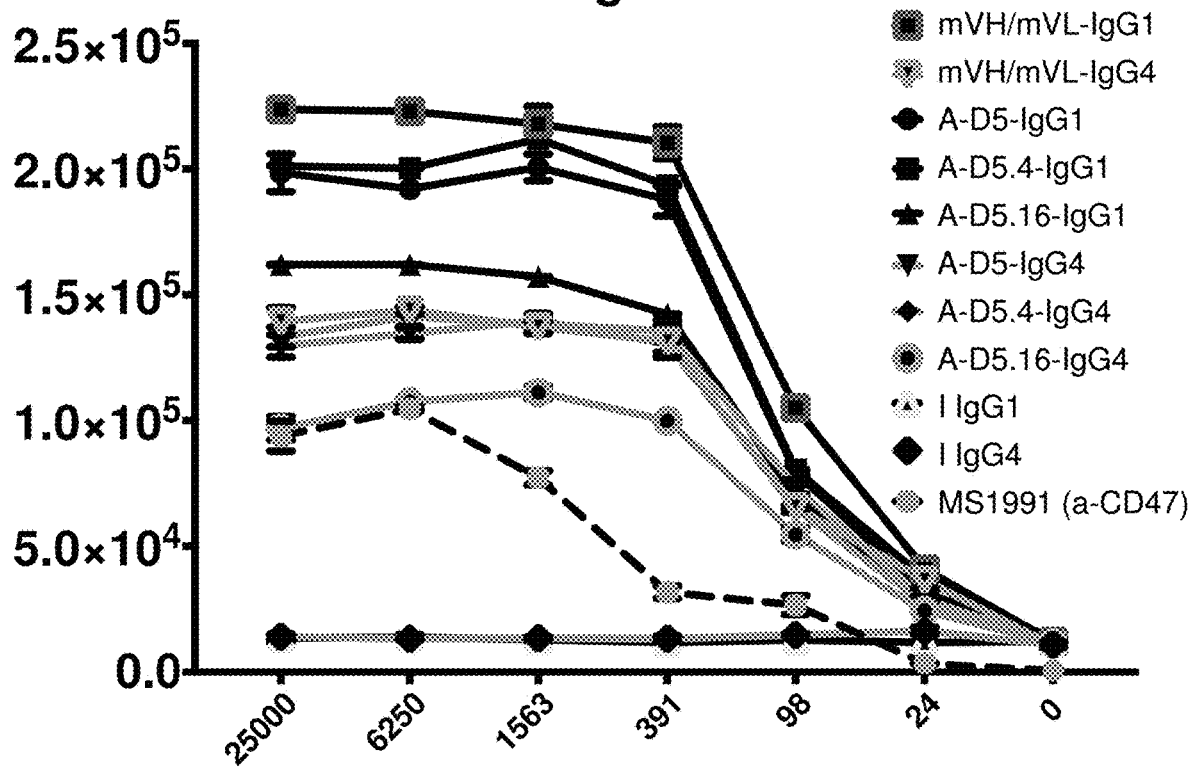

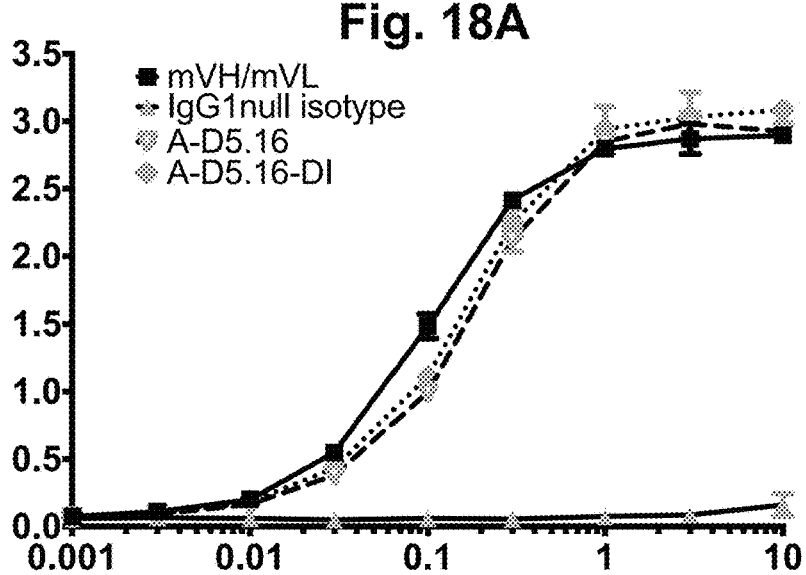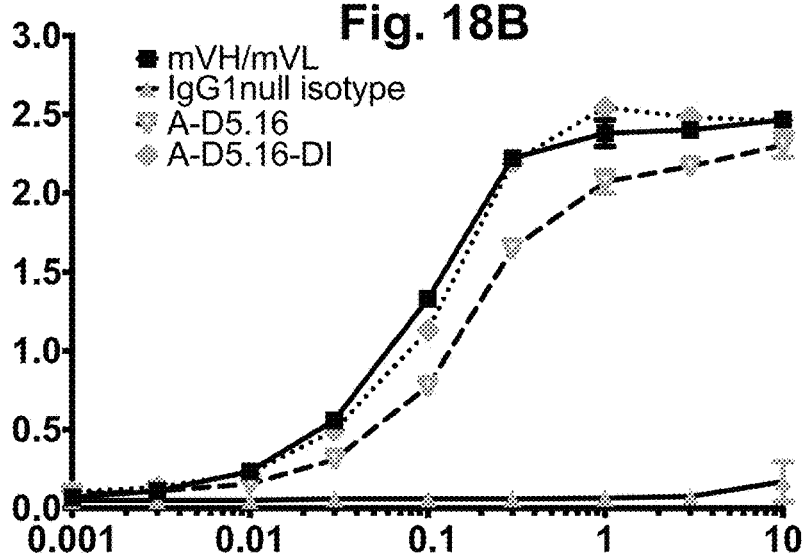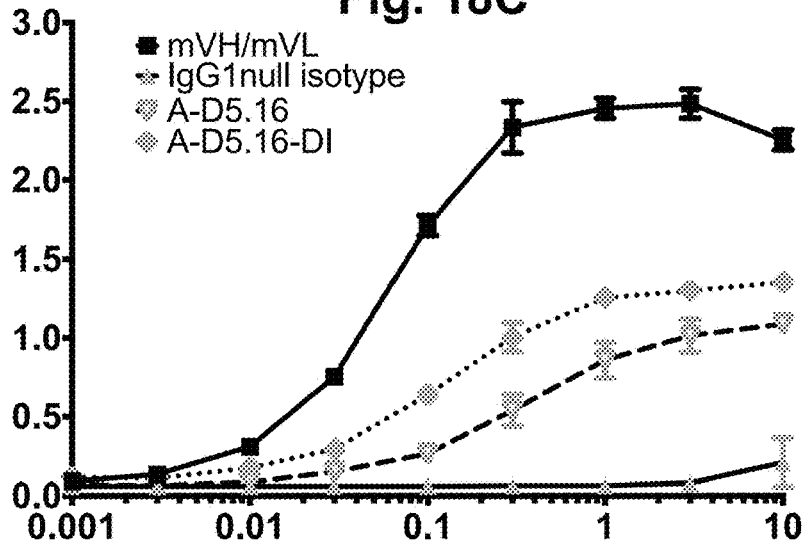

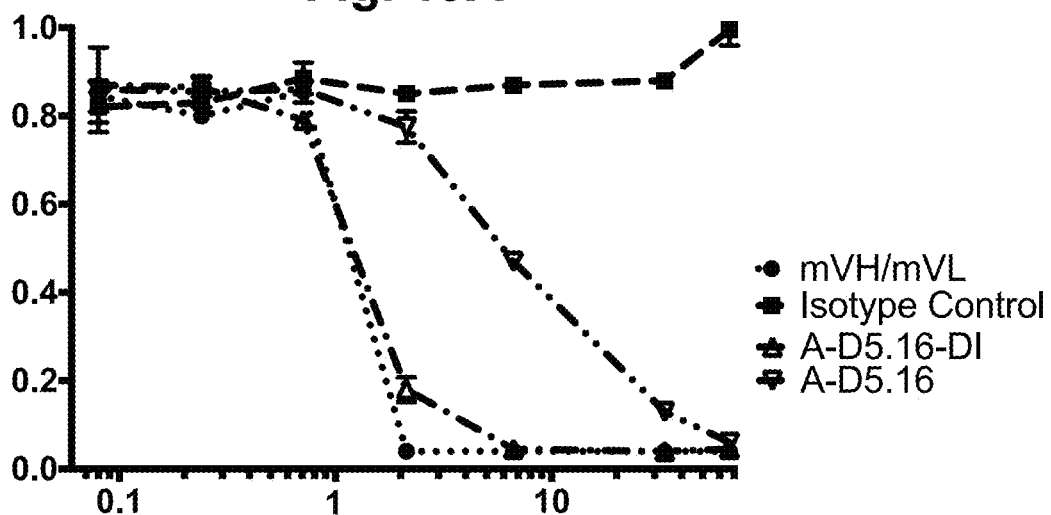
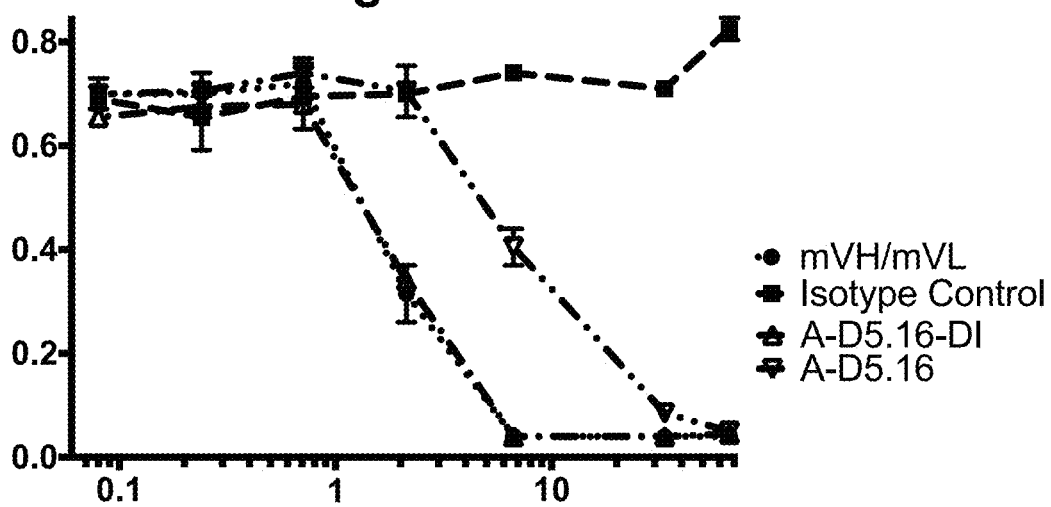
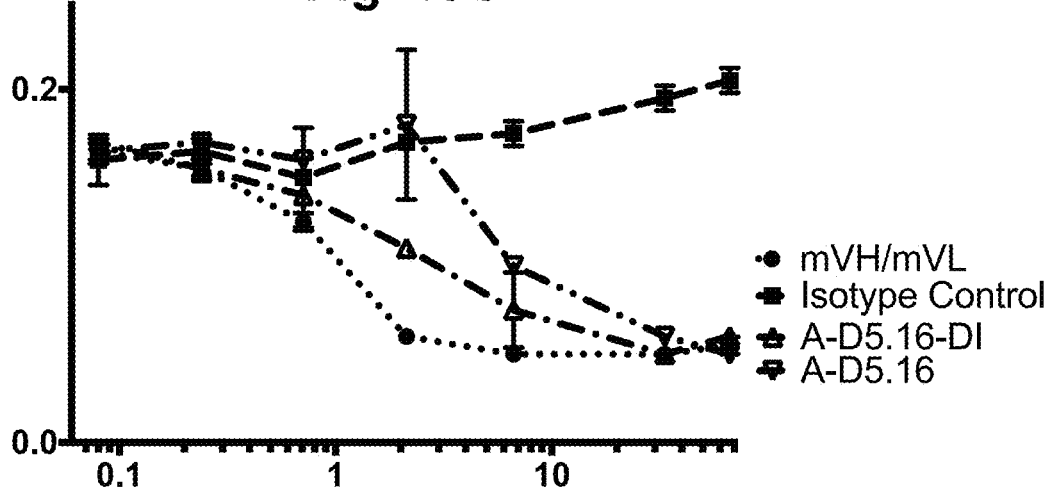

SEQUENCE LISTING

<160> NUMBER OF SEQ ID NOS: 302

<210> SEQ ID NO 1
<211> LENGTH: 10
<212> TYPE: PRT
<213> ORGANISM: Artificial Sequence
<220> FEATURE:
<223> OTHER INFORMATION: Modified CDR

```
<220> FEATURE:
<221> NAME/KEY: VARIANT
<222> LOCATION: (3)..(3)
<223> OTHER INFORMATION: T or any amino acid (for example, S, N or R)
<220> FEATURE:
<221> NAME/KEY: VARIANT
<222> LOCATION: (5)..(5)
<223> OTHER INFORMATION: T or a conservative substitution of T
<220> FEATURE:
<221> NAME/KEY: VARIANT
<222> LOCATION: (6)..(6)
<223> OTHER INFORMATION: N or a conservative substitution of N
<220> FEATURE:
<221> NAME/KEY: VARIANT
<222> LOCATION: (9)..(9)
<223> OTHER INFORMATION: I or a conservative substitution of I
<220> FEATURE:
<221> NAME/KEY: VARIANT
<222> LOCATION: (10)..(10)
<223> OTHER INFORMATION: F or any amino acid (for example, V or G)

<400> SEQUENCE: 1

Gly Tyr Xaa Phe Xaa Xaa Tyr Tyr Xaa Xaa
1               5                   10

<210> SEQ ID NO 2
<211> LENGTH: 19
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: M or a conservative substitution of M
<220> FEATURE:
<221> NAME/KEY: VARIANT
<222> LOCATION: (3)..(3)
<223> OTHER INFORMATION: I or any amino acid (for example, N, V or D)
<220> FEATURE:
<221> NAME/KEY: VARIANT
<222> LOCATION: (5)..(5)
<223> OTHER INFORMATION: N or any amino acid (for example, Y)
<220> FEATURE:
<221> NAME/KEY: VARIANT
<222> LOCATION: (7)..(7)
<223> OTHER INFORMATION: V or any amino acid (for example, G or F)
<220> FEATURE:
<221> NAME/KEY: VARIANT
<222> LOCATION: (8)..(8)
<223> OTHER INFORMATION: D or a conservative substitution of D
<220> FEATURE:
<221> NAME/KEY: VARIANT
<222> LOCATION: (9)..(9)
<223> OTHER INFORMATION: G or a conservative substitution of G
<220> FEATURE:
<221> NAME/KEY: VARIANT
<222> LOCATION: (12)..(12)
<223> OTHER INFORMATION: N or a conservative substitution of N (for
      example, R)
<220> FEATURE:
<221> NAME/KEY: VARIANT
<222> LOCATION: (13)..(13)
<223> OTHER INFORMATION: Y or a conservative substitution of Y
<220> FEATURE:
<221> NAME/KEY: VARIANT
<222> LOCATION: (14)..(14)
<223> OTHER INFORMATION: N or a conservative substitution of N (for
      example, S)

<400> SEQUENCE: 2

Xaa Gly Xaa Ile Xaa Pro Xaa Xaa Xaa Asp Thr Xaa Xaa Xaa Pro Ser
1               5                   10                  15

Phe Gln Gly
```

```
<210> SEQ ID NO 3
<211> LENGTH: 7
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: Y or any amino acid (for example, H, I, Q or F)
<220> FEATURE:
<221> NAME/KEY: VARIANT
<222> LOCATION: (4)..(4)
<223> OTHER INFORMATION: T or any amino acid (for example, V or I)
<220> FEATURE:
<221> NAME/KEY: VARIANT
<222> LOCATION: (5)..(5)
<223> OTHER INFORMATION: M or any amino acid (for example, T, R, P, A or
      L)
<220> FEATURE:
<221> NAME/KEY: VARIANT
<222> LOCATION: (6)..(6)
<223> OTHER INFORMATION: D or any amino acid (for example, G)
<220> FEATURE:
<221> NAME/KEY: VARIANT
<222> LOCATION: (7)..(7)
<223> OTHER INFORMATION: R or any amino acid (for example, Q, N, Y, S,
      W, K, A, E, F, H, I, L, M, T or V)

<400> SEQUENCE: 3

Gly Gly Xaa Xaa Xaa Xaa Xaa
1               5

<210> SEQ ID NO 4
<211> LENGTH: 10
<212> TYPE: PRT
<213> ORGANISM: Mus musculus

<400> SEQUENCE: 4

Gly Tyr Thr Phe Thr Asn Tyr Tyr Val Phe
1               5                   10

<210> SEQ ID NO 5
<211> LENGTH: 7
<212> TYPE: PRT
<213> ORGANISM: Mus musculus

<400> SEQUENCE: 5

Gly Gly Tyr Thr Met Asp Tyr
1               5

<210> SEQ ID NO 6
<211> LENGTH: 16
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (4)..(4)
<223> OTHER INFORMATION: Q or a conservative substitution of Q
<220> FEATURE:
<221> NAME/KEY: VARIANT
<222> LOCATION: (6)..(6)
<223> OTHER INFORMATION: L or a conservative substitution of L
<220> FEATURE:
<221> NAME/KEY: VARIANT
<222> LOCATION: (7)..(7)
<223> OTHER INFORMATION: L or a conservative substitution of L
<220> FEATURE:
<221> NAME/KEY: VARIANT
<222> LOCATION: (10)..(10)
```

```
<223> OTHER INFORMATION: N or any amino acid (for example, Q, S, T, A or
      G) or a conservative substitution of N (for example, Q, S, T or G)
<220> FEATURE:
<221> NAME/KEY: VARIANT
<222> LOCATION: (11)..(11)
<223> OTHER INFORMATION: G or a conservative substitution of G (for
      example, A)
<220> FEATURE:
<221> NAME/KEY: VARIANT
<222> LOCATION: (12)..(12)
<223> OTHER INFORMATION: Y or any amino acid (for example, N or S)
<220> FEATURE:
<221> NAME/KEY: VARIANT
<222> LOCATION: (13)..(13)
<223> OTHER INFORMATION: T or a conservative substitution of T (for
      example, N)
<220> FEATURE:
<221> NAME/KEY: VARIANT
<222> LOCATION: (16)..(16)
<223> OTHER INFORMATION: H or any amino acid (for example, D)

<400> SEQUENCE: 6

Arg Ser Ser Xaa Ser Xaa Xaa His Ser Xaa Xaa Xaa Xaa Tyr Leu Xaa
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: K or any amino acid (for example, L or M)
<220> FEATURE:
<221> NAME/KEY: VARIANT
<222> LOCATION: (2)..(2)
<223> OTHER INFORMATION: V or any amino acid (for example, G)
<220> FEATURE:
<221> NAME/KEY: VARIANT
<222> LOCATION: (4)..(4)
<223> OTHER INFORMATION: N or any amino acid (for example, Y)
<220> FEATURE:
<221> NAME/KEY: VARIANT
<222> LOCATION: (6)..(6)
<223> OTHER INFORMATION: L or any amino acid (for example, F, A or S)

<400> SEQUENCE: 7

Xaa Xaa Ser Xaa Arg Xaa Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: F or any amino acid (for example, L, M, S, T or
      V)
<220> FEATURE:
<221> NAME/KEY: VARIANT
<222> LOCATION: (3)..(3)
<223> OTHER INFORMATION: Q or any amino acid (for example, N, A, T or S)
<220> FEATURE:
<221> NAME/KEY: VARIANT
<222> LOCATION: (4)..(4)
<223> OTHER INFORMATION: T or any amino acid (for example, L, M or I)
<220> FEATURE:
<221> NAME/KEY: VARIANT
<222> LOCATION: (5)..(5)
<223> OTHER INFORMATION: H or a conservative substitution of H
```

```
<220> FEATURE:
<221> NAME/KEY: VARIANT
<222> LOCATION: (6)..(6)
<223> OTHER INFORMATION: T or any amino acid (for example, V, I, A or F)
<220> FEATURE:
<221> NAME/KEY: VARIANT
<222> LOCATION: (7)..(7)
<223> OTHER INFORMATION: P or any amino acid (for example, L)
<220> FEATURE:
<221> NAME/KEY: VARIANT
<222> LOCATION: (8)..(8)
<223> OTHER INFORMATION: R or any amino acid (for example, W)

<400> SEQUENCE: 8

Xaa Gln Xaa Xaa Xaa Xaa Xaa Xaa Thr
1               5

<210> SEQ ID NO 9
<211> LENGTH: 16
<212> TYPE: PRT
<213> ORGANISM: Mus musculus

<400> SEQUENCE: 9

Arg Ser Ser Gln Ser Leu Val His Ser Asn Gly Asn Thr Tyr Leu His
1               5                   10                  15

<210> SEQ ID NO 10
<211> LENGTH: 7
<212> TYPE: PRT
<213> ORGANISM: Mus musculus

<400> SEQUENCE: 10

Lys Val Ser Tyr Arg Phe Ser
1               5

<210> SEQ ID NO 11
<211> LENGTH: 9
<212> TYPE: PRT
<213> ORGANISM: Mus musculus

<400> SEQUENCE: 11

Ser Gln Asn Thr His Val Pro Arg Thr
1               5

<210> SEQ ID NO 12
<211> LENGTH: 10
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (5)..(5)
<223> OTHER INFORMATION: T or any amino acid (for example, S, N or R)
<220> FEATURE:
<221> NAME/KEY: VARIANT
<222> LOCATION: (7)..(7)
<223> OTHER INFORMATION: T or a conservative substitution of T
<220> FEATURE:
<221> NAME/KEY: VARIANT
<222> LOCATION: (8)..(8)
<223> OTHER INFORMATION: N or a conservative substitution of N

<400> SEQUENCE: 12

Gly Ser Gly Tyr Xaa Phe Xaa Xaa Tyr Tyr
1               5                   10

<210> SEQ ID NO 13
<211> LENGTH: 16
```

```
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (2)..(2)
<223> OTHER INFORMATION: N or any amino acid (for example, Y)
<220> FEATURE:
<221> NAME/KEY: VARIANT
<222> LOCATION: (4)..(4)
<223> OTHER INFORMATION: V or any amino acid (for example, G or F)
<220> FEATURE:
<221> NAME/KEY: VARIANT
<222> LOCATION: (5)..(5)
<223> OTHER INFORMATION: D or a conservative substitution of D
<220> FEATURE:
<221> NAME/KEY: VARIANT
<222> LOCATION: (6)..(6)
<223> OTHER INFORMATION: G or a conservative substitution of G
<220> FEATURE:
<221> NAME/KEY: VARIANT
<222> LOCATION: (9)..(9)
<223> OTHER INFORMATION: N or a conservative substitution of N (for
      example, R)
<220> FEATURE:
<221> NAME/KEY: VARIANT
<222> LOCATION: (10)..(10)
<223> OTHER INFORMATION: Y or a conservative substitution of Y
<220> FEATURE:
<221> NAME/KEY: VARIANT
<222> LOCATION: (11)..(11)
<223> OTHER INFORMATION: N or a conservative substitution of N (for
      example, S)

<400> SEQUENCE: 13

Ile Xaa Pro Xaa Xaa Xaa Asp Thr Xaa Xaa Xaa Pro Ser Phe Gln Gly
1               5                   10                  15

<210> SEQ ID NO 14
<211> LENGTH: 6
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: Y or any amino acid (for example, H, I, Q or F)
<220> FEATURE:
<221> NAME/KEY: VARIANT
<222> LOCATION: (4)..(4)
<223> OTHER INFORMATION: T or any amino acid (for example, V or I)
<220> FEATURE:
<221> NAME/KEY: VARIANT
<222> LOCATION: (5)..(5)
<223> OTHER INFORMATION: M or any amino acid (for example, T, R, P, A or
      L)
<220> FEATURE:
<221> NAME/KEY: VARIANT
<222> LOCATION: (6)..(6)
<223> OTHER INFORMATION: D or any amino acid (for example, G)

<400> SEQUENCE: 14

Gly Gly Xaa Xaa Xaa Xaa
1               5

<210> SEQ ID NO 15
<211> LENGTH: 10
<212> TYPE: PRT
<213> ORGANISM: Mus musculus

<400> SEQUENCE: 15

Gly Ser Gly Tyr Thr Phe Thr Asn Tyr Tyr
```

```
<210> SEQ ID NO 16
<211> LENGTH: 6
<212> TYPE: PRT
<213> ORGANISM: Mus musculus

<400> SEQUENCE: 16

Gly Gly Tyr Thr Met Asp
1               5

<210> SEQ ID NO 17
<211> LENGTH: 13
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: Q or a conservative substitution of Q
<220> FEATURE:
<221> NAME/KEY: VARIANT
<222> LOCATION: (5)..(5)
<223> OTHER INFORMATION: L or a conservative substitution of L
<220> FEATURE:
<221> NAME/KEY: VARIANT
<222> LOCATION: (6)..(6)
<223> OTHER INFORMATION: L or a conservative substitution of L
<220> FEATURE:
<221> NAME/KEY: VARIANT
<222> LOCATION: (9)..(9)
<223> OTHER INFORMATION: N or any amino acid (for example, Q, S, T, A or
      G) or a conservative substitution of N (for example, Q, S, T or G)
<220> FEATURE:
<221> NAME/KEY: VARIANT
<222> LOCATION: (10)..(10)
<223> OTHER INFORMATION: G or a conservative substitution of G (for
      example, A)
<220> FEATURE:
<221> NAME/KEY: VARIANT
<222> LOCATION: (11)..(11)
<223> OTHER INFORMATION: Y or any amino acid (for example, N or S)
<220> FEATURE:
<221> NAME/KEY: VARIANT
<222> LOCATION: (12)..(12)
<223> OTHER INFORMATION: T or a conservative substitution of T (for
      example, N)

<400> SEQUENCE: 17

Ser Ser Xaa Ser Xaa Xaa His Ser Xaa Xaa Xaa Xaa Tyr
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Q or any amino acid (for example, N, A, T or S)
<220> FEATURE:
<221> NAME/KEY: VARIANT
<222> LOCATION: (2)..(2)
<223> OTHER INFORMATION: T or any amino acid (for example, L, M or I)
<220> FEATURE:
<221> NAME/KEY: VARIANT
<222> LOCATION: (3)..(3)
<223> OTHER INFORMATION: H or a conservative substitution of H
<220> FEATURE:
<221> NAME/KEY: VARIANT
<222> LOCATION: (4)..(4)
```

```
<223> OTHER INFORMATION: T or any amino acid (for example, V, I, A or F)
<220> FEATURE:
<221> NAME/KEY: VARIANT
<222> LOCATION: (5)..(5)
<223> OTHER INFORMATION: P or any amino acid (for example, L)
<220> FEATURE:
<221> NAME/KEY: VARIANT
<222> LOCATION: (6)..(6)
<223> OTHER INFORMATION: R or any amino acid (for example, W)

<400> SEQUENCE: 18

Xaa Xaa Xaa Xaa Xaa Xaa
1               5

<210> SEQ ID NO 19
<211> LENGTH: 13
<212> TYPE: PRT
<213> ORGANISM: Mus musculus

<400> SEQUENCE: 19

Ser Ser Gln Ser Leu Val His Ser Asn Gly Asn Thr Tyr
1               5                   10

<210> SEQ ID NO 20
<211> LENGTH: 6
<212> TYPE: PRT
<213> ORGANISM: Mus musculus

<400> SEQUENCE: 20

Asn Thr His Val Pro Arg
1               5

<210> SEQ ID NO 21
<211> LENGTH: 10
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: T/S/N/R
<220> FEATURE:
<221> NAME/KEY: VARIANT
<222> LOCATION: (5)..(5)
<223> OTHER INFORMATION: T/N
<220> FEATURE:
<221> NAME/KEY: VARIANT
<222> LOCATION: (6)..(6)
<223> OTHER INFORMATION: N/S
<220> FEATURE:
<221> NAME/KEY: VARIANT
<222> LOCATION: (9)..(9)
<223> OTHER INFORMATION: I/V
<220> FEATURE:
<221> NAME/KEY: VARIANT
<222> LOCATION: (10)..(10)
<223> OTHER INFORMATION: F/V/G

<400> SEQUENCE: 21

Gly Tyr Xaa Phe Xaa Xaa Tyr Tyr Xaa Xaa
1               5                   10

<210> SEQ ID NO 22
<211> LENGTH: 19
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
```

```
<222> LOCATION: (1)..(1)
<223> OTHER INFORMATION: M/I
<220> FEATURE:
<221> NAME/KEY: VARIANT
<222> LOCATION: (3)..(3)
<223> OTHER INFORMATION: V/N/I/D
<220> FEATURE:
<221> NAME/KEY: VARIANT
<222> LOCATION: (5)..(5)
<223> OTHER INFORMATION: N/Y
<220> FEATURE:
<221> NAME/KEY: VARIANT
<222> LOCATION: (7)..(7)
<223> OTHER INFORMATION: V/G/F
<220> FEATURE:
<221> NAME/KEY: VARIANT
<222> LOCATION: (8)..(8)
<223> OTHER INFORMATION: N/D
<220> FEATURE:
<221> NAME/KEY: VARIANT
<222> LOCATION: (9)..(9)
<223> OTHER INFORMATION: G/S
<220> FEATURE:
<221> NAME/KEY: VARIANT
<222> LOCATION: (12)..(12)
<223> OTHER INFORMATION: N/R/K
<220> FEATURE:
<221> NAME/KEY: VARIANT
<222> LOCATION: (13)..(13)
<223> OTHER INFORMATION: F/Y
<220> FEATURE:
<221> NAME/KEY: VARIANT
<222> LOCATION: (14)..(14)
<223> OTHER INFORMATION: N/S

<400> SEQUENCE: 22

Xaa Gly Xaa Ile Xaa Pro Xaa Xaa Xaa Asp Thr Xaa Xaa Xaa Pro Ser
1               5                   10                  15

Phe Gln Gly

<210> SEQ ID NO 23
<211> LENGTH: 7
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: F/H/I/Q/Y
<220> FEATURE:
<221> NAME/KEY: VARIANT
<222> LOCATION: (4)..(4)
<223> OTHER INFORMATION: T/V/I
<220> FEATURE:
<221> NAME/KEY: VARIANT
<222> LOCATION: (5)..(5)
<223> OTHER INFORMATION: M/T/R/P/A/L
<220> FEATURE:
<221> NAME/KEY: VARIANT
<222> LOCATION: (6)..(6)
<223> OTHER INFORMATION: D/G
<220> FEATURE:
<221> NAME/KEY: VARIANT
<222> LOCATION: (7)..(7)
<223> OTHER INFORMATION: Y/Q/N/R/S/W/K/A/E/F/H/I/L/M/T/V

<400> SEQUENCE: 23

Gly Gly Xaa Xaa Xaa Xaa Xaa
1               5

<210> SEQ ID NO 24
<211> LENGTH: 10
<212> TYPE: PRT
```

```
<213> ORGANISM: Artificial Sequence
<220> FEATURE:
<223> OTHER INFORMATION: Modified CDR
<220> FEATURE:
<221> NAME/KEY: VARIANT
<222> LOCATION: (5)..(5)
<223> OTHER INFORMATION: T/S/N/R
<220> FEATURE:
<221> NAME/KEY: VARIANT
<222> LOCATION: (7)..(7)
<223> OTHER INFORMATION: T/N
<220> FEATURE:
<221> NAME/KEY: VARIANT
<222> LOCATION: (8)..(8)
<223> OTHER INFORMATION: N/S

<400> SEQUENCE: 24

Gly Ser Gly Tyr Xaa Phe Xaa Xaa Tyr Tyr
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (2)..(2)
<223> OTHER INFORMATION: N/Y
<220> FEATURE:
<221> NAME/KEY: VARIANT
<222> LOCATION: (4)..(4)
<223> OTHER INFORMATION: V/G/F
<220> FEATURE:
<221> NAME/KEY: VARIANT
<222> LOCATION: (5)..(5)
<223> OTHER INFORMATION: N/D
<220> FEATURE:
<221> NAME/KEY: VARIANT
<222> LOCATION: (6)..(6)
<223> OTHER INFORMATION: G/S
<220> FEATURE:
<221> NAME/KEY: VARIANT
<222> LOCATION: (9)..(9)
<223> OTHER INFORMATION: N/R/K
<220> FEATURE:
<221> NAME/KEY: VARIANT
<222> LOCATION: (10)..(10)
<223> OTHER INFORMATION: F/Y
<220> FEATURE:
<221> NAME/KEY: VARIANT
<222> LOCATION: (11)..(11)
<223> OTHER INFORMATION: N/S

<400> SEQUENCE: 25

Ile Xaa Pro Xaa Xaa Xaa Asp Thr Xaa Xaa Xaa Pro Ser Phe Gln Gly
1               5                   10                  15

<210> SEQ ID NO 26
<211> LENGTH: 6
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: F/H/I/Q/Y
<220> FEATURE:
<221> NAME/KEY: VARIANT
<222> LOCATION: (4)..(4)
<223> OTHER INFORMATION: T/V/I
<220> FEATURE:
<221> NAME/KEY: VARIANT
```

```
<222> LOCATION: (5)..(5)
<223> OTHER INFORMATION: M/T/R/P/A/L
<220> FEATURE:
<221> NAME/KEY: VARIANT
<222> LOCATION: (6)..(6)
<223> OTHER INFORMATION: D/G

<400> SEQUENCE: 26

Gly Gly Xaa Xaa Xaa Xaa
1               5

<210> SEQ ID NO 27
<211> LENGTH: 10
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: T/S

<400> SEQUENCE: 27

Gly Tyr Xaa Phe Thr Asn Tyr Tyr Ile Phe
1               5                   10

<210> SEQ ID NO 28
<211> LENGTH: 19
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: M/I
<220> FEATURE:
<221> NAME/KEY: VARIANT
<222> LOCATION: (3)..(3)
<223> OTHER INFORMATION: I/D
<220> FEATURE:
<221> NAME/KEY: VARIANT
<222> LOCATION: (8)..(8)
<223> OTHER INFORMATION: N/D
<220> FEATURE:
<221> NAME/KEY: VARIANT
<222> LOCATION: (12)..(12)
<223> OTHER INFORMATION: N/R
<220> FEATURE:
<221> NAME/KEY: VARIANT
<222> LOCATION: (13)..(13)
<223> OTHER INFORMATION: F/Y
<220> FEATURE:
<221> NAME/KEY: VARIANT
<222> LOCATION: (14)..(14)
<223> OTHER INFORMATION: N/S

<400> SEQUENCE: 28

Xaa Gly Xaa Ile Asn Pro Val Xaa Gly Asp Thr Xaa Xaa Xaa Pro Ser
1               5                   10                  15

Phe Gln Gly

<210> SEQ ID NO 29
<211> LENGTH: 7
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: F/Y
```

```
<220> FEATURE:
<221> NAME/KEY: VARIANT
<222> LOCATION: (5)..(5)
<223> OTHER INFORMATION: M/P
<220> FEATURE:
<221> NAME/KEY: VARIANT
<222> LOCATION: (7)..(7)
<223> OTHER INFORMATION: Y/R/K/I

<400> SEQUENCE: 29

Gly Gly Xaa Thr Xaa Asp Xaa
1               5

<210> SEQ ID NO 30
<211> LENGTH: 10
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (5)..(5)
<223> OTHER INFORMATION: T/S

<400> SEQUENCE: 30

Gly Ser Gly Tyr Xaa Phe Thr Asn Tyr Tyr
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (5)..(5)
<223> OTHER INFORMATION: N/D
<220> FEATURE:
<221> NAME/KEY: VARIANT
<222> LOCATION: (9)..(9)
<223> OTHER INFORMATION: N/R
<220> FEATURE:
<221> NAME/KEY: VARIANT
<222> LOCATION: (10)..(10)
<223> OTHER INFORMATION: F/Y
<220> FEATURE:
<221> NAME/KEY: VARIANT
<222> LOCATION: (11)..(11)
<223> OTHER INFORMATION: N/S

<400> SEQUENCE: 31

Ile Asn Pro Val Xaa Gly Asp Thr Xaa Xaa Xaa Pro Ser Phe Gln Gly
1               5                   10                  15

<210> SEQ ID NO 32
<211> LENGTH: 6
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: F/Y
<220> FEATURE:
<221> NAME/KEY: VARIANT
<222> LOCATION: (5)..(5)
<223> OTHER INFORMATION: M/P

<400> SEQUENCE: 32

Gly Gly Xaa Thr Xaa Asp
```

```
<210> SEQ ID NO 33
<211> LENGTH: 16
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (4)..(4)
<223> OTHER INFORMATION: Q/H
<220> FEATURE:
<221> NAME/KEY: VARIANT
<222> LOCATION: (6)..(6)
<223> OTHER INFORMATION: F/L
<220> FEATURE:
<221> NAME/KEY: VARIANT
<222> LOCATION: (7)..(7)
<223> OTHER INFORMATION: L/V
<220> FEATURE:
<221> NAME/KEY: VARIANT
<222> LOCATION: (10)..(10)
<223> OTHER INFORMATION: N/Q/A
<220> FEATURE:
<221> NAME/KEY: VARIANT
<222> LOCATION: (11)..(11)
<223> OTHER INFORMATION: G/A
<220> FEATURE:
<221> NAME/KEY: VARIANT
<222> LOCATION: (12)..(12)
<223> OTHER INFORMATION: Y/N/S
<220> FEATURE:
<221> NAME/KEY: VARIANT
<222> LOCATION: (13)..(13)
<223> OTHER INFORMATION: N/T
<220> FEATURE:
<221> NAME/KEY: VARIANT
<222> LOCATION: (16)..(16)
<223> OTHER INFORMATION: H/D

<400> SEQUENCE: 33

Arg Ser Ser Xaa Ser Xaa Xaa His Ser Xaa Xaa Xaa Xaa Tyr Leu Xaa
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: L/K/M
<220> FEATURE:
<221> NAME/KEY: VARIANT
<222> LOCATION: (2)..(2)
<223> OTHER INFORMATION: V/G
<220> FEATURE:
<221> NAME/KEY: VARIANT
<222> LOCATION: (4)..(4)
<223> OTHER INFORMATION: N/Y
<220> FEATURE:
<221> NAME/KEY: VARIANT
<222> LOCATION: (6)..(6)
<223> OTHER INFORMATION: A/F/L/S

<400> SEQUENCE: 34

Xaa Xaa Ser Xaa Arg Xaa Ser
1               5

<210> SEQ ID NO 35
<211> LENGTH: 9
```

```
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: F/L/M/S/T/V
<220> FEATURE:
<221> NAME/KEY: VARIANT
<222> LOCATION: (3)..(3)
<223> OTHER INFORMATION: Q/N/A/T/S
<220> FEATURE:
<221> NAME/KEY: VARIANT
<222> LOCATION: (4)..(4)
<223> OTHER INFORMATION: T/L/M/I
<220> FEATURE:
<221> NAME/KEY: VARIANT
<222> LOCATION: (5)..(5)
<223> OTHER INFORMATION: Q/H
<220> FEATURE:
<221> NAME/KEY: VARIANT
<222> LOCATION: (6)..(6)
<223> OTHER INFORMATION: T/V/I/A/F
<220> FEATURE:
<221> NAME/KEY: VARIANT
<222> LOCATION: (7)..(7)
<223> OTHER INFORMATION: P/L
<220> FEATURE:
<221> NAME/KEY: VARIANT
<222> LOCATION: (8)..(8)
<223> OTHER INFORMATION: R/W

<400> SEQUENCE: 35

Xaa Gln Xaa Xaa Xaa Xaa Xaa Xaa Thr
1               5

<210> SEQ ID NO 36
<211> LENGTH: 13
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: Q/H
<220> FEATURE:
<221> NAME/KEY: VARIANT
<222> LOCATION: (5)..(5)
<223> OTHER INFORMATION: F/L
<220> FEATURE:
<221> NAME/KEY: VARIANT
<222> LOCATION: (6)..(6)
<223> OTHER INFORMATION: L/V
<220> FEATURE:
<221> NAME/KEY: VARIANT
<222> LOCATION: (9)..(9)
<223> OTHER INFORMATION: N/Q/A
<220> FEATURE:
<221> NAME/KEY: VARIANT
<222> LOCATION: (10)..(10)
<223> OTHER INFORMATION: G/A
<220> FEATURE:
<221> NAME/KEY: VARIANT
<222> LOCATION: (11)..(11)
<223> OTHER INFORMATION: Y/N/S
<220> FEATURE:
<221> NAME/KEY: VARIANT
<222> LOCATION: (12)..(12)
<223> OTHER INFORMATION: N/T

<400> SEQUENCE: 36

Ser Ser Xaa Ser Xaa Xaa His Ser Xaa Xaa Xaa Xaa Tyr
1               5                   10
```

```
<210> SEQ ID NO 37
<211> LENGTH: 6
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Q/N/A/T/S
<220> FEATURE:
<221> NAME/KEY: VARIANT
<222> LOCATION: (2)..(2)
<223> OTHER INFORMATION: T/L/M/I
<220> FEATURE:
<221> NAME/KEY: VARIANT
<222> LOCATION: (3)..(3)
<223> OTHER INFORMATION: Q/H
<220> FEATURE:
<221> NAME/KEY: VARIANT
<222> LOCATION: (4)..(4)
<223> OTHER INFORMATION: T/V/I/A/F
<220> FEATURE:
<221> NAME/KEY: VARIANT
<222> LOCATION: (5)..(5)
<223> OTHER INFORMATION: P/L
<220> FEATURE:
<221> NAME/KEY: VARIANT
<222> LOCATION: (6)..(6)
<223> OTHER INFORMATION: R/W

<400> SEQUENCE: 37

Xaa Xaa Xaa Xaa Xaa Xaa
1               5

<210> SEQ ID NO 38
<211> LENGTH: 16
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (7)..(7)
<223> OTHER INFORMATION: L/V
<220> FEATURE:
<221> NAME/KEY: VARIANT
<222> LOCATION: (10)..(10)
<223> OTHER INFORMATION: N/Q/A
<220> FEATURE:
<221> NAME/KEY: VARIANT
<222> LOCATION: (12)..(12)
<223> OTHER INFORMATION: Y/N
<220> FEATURE:
<221> NAME/KEY: VARIANT
<222> LOCATION: (13)..(13)
<223> OTHER INFORMATION: N/T
<220> FEATURE:
<221> NAME/KEY: VARIANT
<222> LOCATION: (16)..(16)
<223> OTHER INFORMATION: H/D

<400> SEQUENCE: 38

Arg Ser Ser Gln Ser Leu Xaa His Ser Xaa Gly Xaa Xaa Tyr Leu Xaa
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
```

```
<222> LOCATION: (1)..(1)
<223> OTHER INFORMATION: L/K
<220> FEATURE:
<221> NAME/KEY: VARIANT
<222> LOCATION: (2)..(2)
<223> OTHER INFORMATION: V/G
<220> FEATURE:
<221> NAME/KEY: VARIANT
<222> LOCATION: (4)..(4)
<223> OTHER INFORMATION: N/Y
<220> FEATURE:
<221> NAME/KEY: VARIANT
<222> LOCATION: (6)..(6)
<223> OTHER INFORMATION: A/F/L

<400> SEQUENCE: 39

Xaa Xaa Ser Xaa Arg Xaa Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: F/S
<220> FEATURE:
<221> NAME/KEY: VARIANT
<222> LOCATION: (3)..(3)
<223> OTHER INFORMATION: Q/N/A
<220> FEATURE:
<221> NAME/KEY: VARIANT
<222> LOCATION: (4)..(4)
<223> OTHER INFORMATION: T/L
<220> FEATURE:
<221> NAME/KEY: VARIANT
<222> LOCATION: (5)..(5)
<223> OTHER INFORMATION: Q/H
<220> FEATURE:
<221> NAME/KEY: VARIANT
<222> LOCATION: (6)..(6)
<223> OTHER INFORMATION: T/V

<400> SEQUENCE: 40

Xaa Gln Xaa Xaa Xaa Xaa Pro Arg Thr
1               5

<210> SEQ ID NO 41
<211> LENGTH: 13
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (6)..(6)
<223> OTHER INFORMATION: L/V
<220> FEATURE:
<221> NAME/KEY: VARIANT
<222> LOCATION: (9)..(9)
<223> OTHER INFORMATION: N/Q/A
<220> FEATURE:
<221> NAME/KEY: VARIANT
<222> LOCATION: (11)..(11)
<223> OTHER INFORMATION: Y/N
<220> FEATURE:
<221> NAME/KEY: VARIANT
<222> LOCATION: (12)..(12)
<223> OTHER INFORMATION: N/T

<400> SEQUENCE: 41
```

```
Ser Ser Gln Ser Leu Xaa His Ser Xaa Gly Xaa Xaa Tyr
1               5                   10
```

<210> SEQ ID NO 42
<211> LENGTH: 6
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Q/N/A
<220> FEATURE:
<221> NAME/KEY: VARIANT
<222> LOCATION: (2)..(2)
<223> OTHER INFORMATION: T/L
<220> FEATURE:
<221> NAME/KEY: VARIANT
<222> LOCATION: (3)..(3)
<223> OTHER INFORMATION: Q/H
<220> FEATURE:
<221> NAME/KEY: VARIANT
<222> LOCATION: (4)..(4)
<223> OTHER INFORMATION: T/V

<400> SEQUENCE: 42

```
Xaa Xaa Xaa Xaa Pro Arg
1               5
```

<210> SEQ ID NO 43
<211> LENGTH: 10
<212> TYPE: PRT
<213> ORGANISM: Artificial Sequence
<220> FEATURE:
<223> OTHER INFORMATION: Modified CDR

<400> SEQUENCE: 43

```
Gly Tyr Ser Phe Thr Asn Tyr Tyr Ile Phe
1               5                   10
```

<210> SEQ ID NO 44
<211> LENGTH: 19
<212> TYPE: PRT
<213> ORGANISM: Artificial Sequence
<220> FEATURE:
<223> OTHER INFORMATION: Modified CDR

<400> SEQUENCE: 44

```
Met Gly Asp Ile Asn Pro Val Asn Gly Asp Thr Asn Tyr Ser Pro Ser
1               5                   10                  15

Phe Gln Gly
```

<210> SEQ ID NO 45
<211> LENGTH: 7
<212> TYPE: PRT
<213> ORGANISM: Artificial Sequence
<220> FEATURE:
<223> OTHER INFORMATION: Modified CDR

<400> SEQUENCE: 45

```
Gly Gly Tyr Thr Pro Asp Tyr
1               5
```

<210> SEQ ID NO 46
<211> LENGTH: 16
<212> TYPE: PRT
<213> ORGANISM: Artificial Sequence
<220> FEATURE:

<223> OTHER INFORMATION: Modified CDR

<400> SEQUENCE: 46

Arg Ser Ser Gln Ser Leu Leu His Ser Asn Gly Tyr Asn Tyr Leu His
1               5                   10                  15

<210> SEQ ID NO 47
<211> LENGTH: 7
<212> TYPE: PRT
<213> ORGANISM: Artificial Sequence
<220> FEATURE:
<223> OTHER INFORMATION: Modified CDR

<400> SEQUENCE: 47

Lys Gly Ser Asn Arg Phe Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Modified CDR

<400> SEQUENCE: 48

Ser Gln Asn Leu His Val Pro Arg Thr
1               5

<210> SEQ ID NO 49
<211> LENGTH: 10
<212> TYPE: PRT
<213> ORGANISM: Artificial Sequence
<220> FEATURE:
<223> OTHER INFORMATION: Modified CDR

<400> SEQUENCE: 49

Gly Tyr Thr Phe Thr Asn Tyr Tyr Ile Phe
1               5                   10

<210> SEQ ID NO 50
<211> LENGTH: 19
<212> TYPE: PRT
<213> ORGANISM: Artificial Sequence
<220> FEATURE:
<223> OTHER INFORMATION: Modified CDR

<400> SEQUENCE: 50

Met Gly Ile Ile Asn Pro Val Asp Gly Asp Thr Asn Tyr Asn Pro Ser
1               5                   10                  15

Phe Gln Gly

<210> SEQ ID NO 51
<211> LENGTH: 7
<212> TYPE: PRT
<213> ORGANISM: Artificial Sequence
<220> FEATURE:
<223> OTHER INFORMATION: Modified CDR

<400> SEQUENCE: 51

Gly Gly Tyr Thr Met Asp Arg
1               5

<210> SEQ ID NO 52
<211> LENGTH: 16
<212> TYPE: PRT
<213> ORGANISM: Artificial Sequence

```
<220> FEATURE:
<223> OTHER INFORMATION: Modified CDR

<400> SEQUENCE: 52

Arg Ser Ser Gln Ser Leu Leu His Ser Asn Gly Tyr Thr Tyr Leu His
1               5                   10                  15

<210> SEQ ID NO 53
<211> LENGTH: 7
<212> TYPE: PRT
<213> ORGANISM: Artificial Sequence
<220> FEATURE:
<223> OTHER INFORMATION: Modified CDR

<400> SEQUENCE: 53

Lys Val Ser Asn Arg Leu Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Modified CDR

<400> SEQUENCE: 54

Phe Gln Asn Thr His Thr Pro Arg Thr
1               5

<210> SEQ ID NO 55
<211> LENGTH: 19
<212> TYPE: PRT
<213> ORGANISM: Artificial Sequence
<220> FEATURE:
<223> OTHER INFORMATION: Modified CDR

<400> SEQUENCE: 55

Ile Gly Asp Ile Asn Pro Val Asn Gly Asp Thr Asn Phe Ser Pro Ser
1               5                   10                  15

Phe Gln Gly

<210> SEQ ID NO 56
<211> LENGTH: 7
<212> TYPE: PRT
<213> ORGANISM: Artificial Sequence
<220> FEATURE:
<223> OTHER INFORMATION: Modified CDR

<400> SEQUENCE: 56

Gly Gly Tyr Thr Met Asp Lys
1               5

<210> SEQ ID NO 57
<211> LENGTH: 16
<212> TYPE: PRT
<213> ORGANISM: Artificial Sequence
<220> FEATURE:
<223> OTHER INFORMATION: Modified CDR

<400> SEQUENCE: 57

Arg Ser Ser Gln Ser Leu Val His Ser Asn Gly Tyr Thr Tyr Leu His
1               5                   10                  15

<210> SEQ ID NO 58
<211> LENGTH: 7
<212> TYPE: PRT
```

```
<213> ORGANISM: Artificial Sequence
<220> FEATURE:
<223> OTHER INFORMATION: Modified CDR

<400> SEQUENCE: 58

Lys Gly Ser Tyr Arg Ala Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Modified CDR

<400> SEQUENCE: 59

Ser Gln Asn Thr Gln Thr Pro Arg Thr
1               5

<210> SEQ ID NO 60
<211> LENGTH: 19
<212> TYPE: PRT
<213> ORGANISM: Artificial Sequence
<220> FEATURE:
<223> OTHER INFORMATION: Modified CDR

<400> SEQUENCE: 60

Met Gly Ile Ile Asn Pro Val Asn Gly Asp Thr Asn Tyr Asn Pro Ser
1               5                   10                  15

Phe Gln Gly

<210> SEQ ID NO 61
<211> LENGTH: 7
<212> TYPE: PRT
<213> ORGANISM: Artificial Sequence
<220> FEATURE:
<223> OTHER INFORMATION: Modified CDR

<400> SEQUENCE: 61

Gly Gly Tyr Thr Met Gly Lys
1               5

<210> SEQ ID NO 62
<211> LENGTH: 16
<212> TYPE: PRT
<213> ORGANISM: Artificial Sequence
<220> FEATURE:
<223> OTHER INFORMATION: Modified CDR

<400> SEQUENCE: 62

Arg Ser Ser Gln Ser Leu Val His Ser Asn Gly Asn Thr Tyr Leu Asp
1               5                   10                  15

<210> SEQ ID NO 63
<211> LENGTH: 7
<212> TYPE: PRT
<213> ORGANISM: Artificial Sequence
<220> FEATURE:
<223> OTHER INFORMATION: Modified CDR

<400> SEQUENCE: 63

Lys Gly Ser Tyr Arg Phe Ser
1               5

<210> SEQ ID NO 64
<211> LENGTH: 9
```

```
<212> TYPE: PRT
<213> ORGANISM: Artificial Sequence
<220> FEATURE:
<223> OTHER INFORMATION: Modified CDR

<400> SEQUENCE: 64

Ser Gln Ala Thr His Thr Pro Arg Thr
1               5

<210> SEQ ID NO 65
<211> LENGTH: 19
<212> TYPE: PRT
<213> ORGANISM: Artificial Sequence
<220> FEATURE:
<223> OTHER INFORMATION: Modified CDR

<400> SEQUENCE: 65

Met Gly Ile Ile Asn Pro Val Asp Gly Asp Thr Arg Tyr Ser Pro Ser
1               5                   10                  15

Phe Gln Gly

<210> SEQ ID NO 66
<211> LENGTH: 7
<212> TYPE: PRT
<213> ORGANISM: Artificial Sequence
<220> FEATURE:
<223> OTHER INFORMATION: Modified CDR

<400> SEQUENCE: 66

Gly Gly Phe Thr Met Asp Tyr
1               5

<210> SEQ ID NO 67
<211> LENGTH: 7
<212> TYPE: PRT
<213> ORGANISM: Artificial Sequence
<220> FEATURE:
<223> OTHER INFORMATION: Modified CDR

<400> SEQUENCE: 67

Lys Gly Ser Asn Arg Ala Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Modified CDR

<400> SEQUENCE: 68

Ser Gln Asn Thr His Thr Pro Arg Thr
1               5

<210> SEQ ID NO 69
<211> LENGTH: 19
<212> TYPE: PRT
<213> ORGANISM: Artificial Sequence
<220> FEATURE:
<223> OTHER INFORMATION: Modified CDR

<400> SEQUENCE: 69

Ile Gly Ile Ile Asn Pro Val Asp Gly Asp Thr Arg Tyr Ser Pro Ser
1               5                   10                  15

Phe Gln Gly
```

```
<210> SEQ ID NO 70
<211> LENGTH: 7
<212> TYPE: PRT
<213> ORGANISM: Artificial Sequence
<220> FEATURE:
<223> OTHER INFORMATION: Modified CDR

<400> SEQUENCE: 70

Gly Gly Tyr Thr Met Asp Ile
1               5

<210> SEQ ID NO 71
<211> LENGTH: 7
<212> TYPE: PRT
<213> ORGANISM: Artificial Sequence
<220> FEATURE:
<223> OTHER INFORMATION: Modified CDR

<400> SEQUENCE: 71

Leu Gly Ser Asn Arg Phe Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Modified CDR

<400> SEQUENCE: 72

Leu Gly Ser Asn Arg Ala Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Modified CDR

<400> SEQUENCE: 73

Ser Gln Ala Thr Gln Thr Pro Arg Thr
1               5

<210> SEQ ID NO 74
<211> LENGTH: 19
<212> TYPE: PRT
<213> ORGANISM: Artificial Sequence
<220> FEATURE:
<223> OTHER INFORMATION: Modified CDR

<400> SEQUENCE: 74

Met Gly Ile Ile Asn Pro Val Asp Gly Asp Thr Arg Tyr Asn Pro Ser
1               5                   10                  15

Phe Gln Gly

<210> SEQ ID NO 75
<211> LENGTH: 7
<212> TYPE: PRT
<213> ORGANISM: Artificial Sequence
<220> FEATURE:
<223> OTHER INFORMATION: Modified CDR

<400> SEQUENCE: 75

Lys Gly Ser Asn Arg Leu Ser
1               5
```

<210> SEQ ID NO 76
<211> LENGTH: 9
<212> TYPE: PRT
<213> ORGANISM: Artificial Sequence
<220> FEATURE:
<223> OTHER INFORMATION: Modified CDR

<400> SEQUENCE: 76

Phe Gln Asn Thr Gln Thr Pro Arg Thr
1               5

<210> SEQ ID NO 77
<211> LENGTH: 7
<212> TYPE: PRT
<213> ORGANISM: Artificial Sequence
<220> FEATURE:
<223> OTHER INFORMATION: Modified CDR

<400> SEQUENCE: 77

Leu Gly Ser Asn Arg Leu Ser
1               5

<210> SEQ ID NO 78
<211> LENGTH: 16
<212> TYPE: PRT
<213> ORGANISM: Artificial Sequence
<220> FEATURE:
<223> OTHER INFORMATION: Modified CDR

<400> SEQUENCE: 78

Arg Ser Ser Gln Ser Leu Leu His Ser Gln Gly Tyr Thr Tyr Leu His
1               5                   10                  15

<210> SEQ ID NO 79
<211> LENGTH: 9
<212> TYPE: PRT
<213> ORGANISM: Artificial Sequence
<220> FEATURE:
<223> OTHER INFORMATION: Modified CDR

<400> SEQUENCE: 79

Phe Gln Gln Thr His Thr Pro Arg Thr
1               5

<210> SEQ ID NO 80
<211> LENGTH: 16
<212> TYPE: PRT
<213> ORGANISM: Artificial Sequence
<220> FEATURE:
<223> OTHER INFORMATION: Modified CDR

<400> SEQUENCE: 80

Arg Ser Ser Gln Ser Leu Leu His Ser Ser Gly Tyr Asn Tyr Leu His
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Modified CDR

<400> SEQUENCE: 81

Arg Ser Ser Gln Ser Leu Leu His Ser Gly Gly Tyr Asn Tyr Leu His
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Modified CDR

<400> SEQUENCE: 82

Arg Ser Ser Gln Ser Leu Leu His Ser Ala Gly Tyr Asn Tyr Leu His
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Modified CDR

<400> SEQUENCE: 83

Arg Ser Ser Gln Ser Leu Leu His Ser Thr Gly Tyr Asn Tyr Leu His
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Modified CDR

<400> SEQUENCE: 84

Arg Ser Ser Gln Ser Leu Leu His Ser Asn Ala Tyr Asn Tyr Leu His
1               5                   10                  15

<210> SEQ ID NO 85
<211> LENGTH: 7
<212> TYPE: PRT
<213> ORGANISM: Artificial Sequence
<220> FEATURE:
<223> OTHER INFORMATION: Modified CDR

<400> SEQUENCE: 85

Lys Val Ser Asn Arg Phe Ser
1               5

<210> SEQ ID NO 86
<211> LENGTH: 10
<212> TYPE: PRT
<213> ORGANISM: Artificial Sequence
<220> FEATURE:
<223> OTHER INFORMATION: Modified CDR

<400> SEQUENCE: 86

Gly Ser Gly Tyr Ser Phe Thr Asn Tyr Tyr
1               5                   10

<210> SEQ ID NO 87
<211> LENGTH: 16
<212> TYPE: PRT
<213> ORGANISM: Artificial Sequence
<220> FEATURE:
<223> OTHER INFORMATION: Modified CDR

<400> SEQUENCE: 87

Ile Asn Pro Val Asn Gly Asp Thr Asn Tyr Ser Pro Ser Phe Gln Gly
1               5                   10                  15

```
<210> SEQ ID NO 88
<211> LENGTH: 6
<212> TYPE: PRT
<213> ORGANISM: Artificial Sequence
<220> FEATURE:
<223> OTHER INFORMATION: Modified CDR

<400> SEQUENCE: 88

Gly Gly Tyr Thr Pro Asp
1               5

<210> SEQ ID NO 89
<211> LENGTH: 13
<212> TYPE: PRT
<213> ORGANISM: Artificial Sequence
<220> FEATURE:
<223> OTHER INFORMATION: Modified CDR

<400> SEQUENCE: 89

Ser Ser Gln Ser Leu Leu His Ser Asn Gly Tyr Asn Tyr
1               5                   10

<210> SEQ ID NO 90
<211> LENGTH: 6
<212> TYPE: PRT
<213> ORGANISM: Artificial Sequence
<220> FEATURE:
<223> OTHER INFORMATION: Modified CDR

<400> SEQUENCE: 90

Asn Leu His Val Pro Arg
1               5

<210> SEQ ID NO 91
<211> LENGTH: 16
<212> TYPE: PRT
<213> ORGANISM: Artificial Sequence
<220> FEATURE:
<223> OTHER INFORMATION: Modified CDR

<400> SEQUENCE: 91

Ile Asn Pro Val Asp Gly Asp Thr Asn Tyr Asn Pro Ser Phe Gln Gly
1               5                   10                  15

<210> SEQ ID NO 92
<211> LENGTH: 13
<212> TYPE: PRT
<213> ORGANISM: Artificial Sequence
<220> FEATURE:
<223> OTHER INFORMATION: Modified CDR

<400> SEQUENCE: 92

Ser Ser Gln Ser Leu Leu His Ser Asn Gly Tyr Thr Tyr
1               5                   10

<210> SEQ ID NO 93
<211> LENGTH: 6
<212> TYPE: PRT
<213> ORGANISM: Artificial Sequence
<220> FEATURE:
<223> OTHER INFORMATION: Modified CDR

<400> SEQUENCE: 93

Asn Thr His Thr Pro Arg
1               5

<210> SEQ ID NO 94
```

```
<211> LENGTH: 16
<212> TYPE: PRT
<213> ORGANISM: Artificial Sequence
<220> FEATURE:
<223> OTHER INFORMATION: Modified CDR

<400> SEQUENCE: 94

Ile Asn Pro Val Asn Gly Asp Thr Asn Phe Ser Pro Ser Phe Gln Gly
1               5                   10                  15

<210> SEQ ID NO 95
<211> LENGTH: 13
<212> TYPE: PRT
<213> ORGANISM: Artificial Sequence
<220> FEATURE:
<223> OTHER INFORMATION: Modified CDR

<400> SEQUENCE: 95

Ser Ser Gln Ser Leu Val His Ser Asn Gly Tyr Thr Tyr
1               5                   10

<210> SEQ ID NO 96
<211> LENGTH: 6
<212> TYPE: PRT
<213> ORGANISM: Artificial Sequence
<220> FEATURE:
<223> OTHER INFORMATION: Modified CDR

<400> SEQUENCE: 96

Asn Thr Gln Thr Pro Arg
1               5

<210> SEQ ID NO 97
<211> LENGTH: 16
<212> TYPE: PRT
<213> ORGANISM: Artificial Sequence
<220> FEATURE:
<223> OTHER INFORMATION: Modified CDR

<400> SEQUENCE: 97

Ile Asn Pro Val Asn Gly Asp Thr Asn Tyr Asn Pro Ser Phe Gln Gly
1               5                   10                  15

<210> SEQ ID NO 98
<211> LENGTH: 6
<212> TYPE: PRT
<213> ORGANISM: Artificial Sequence
<220> FEATURE:
<223> OTHER INFORMATION: Modified CDR

<400> SEQUENCE: 98

Gly Gly Tyr Thr Met Gly
1               5

<210> SEQ ID NO 99
<211> LENGTH: 6
<212> TYPE: PRT
<213> ORGANISM: Artificial Sequence
<220> FEATURE:
<223> OTHER INFORMATION: Modified CDR

<400> SEQUENCE: 99

Ala Thr His Thr Pro Arg
1               5

<210> SEQ ID NO 100
<211> LENGTH: 16
```

```
<212> TYPE: PRT
<213> ORGANISM: Artificial Sequence
<220> FEATURE:
<223> OTHER INFORMATION: Modified CDR

<400> SEQUENCE: 100

Ile Asn Pro Val Asp Gly Asp Thr Arg Tyr Ser Pro Ser Phe Gln Gly
1               5                   10                  15

<210> SEQ ID NO 101
<211> LENGTH: 6
<212> TYPE: PRT
<213> ORGANISM: Artificial Sequence
<220> FEATURE:
<223> OTHER INFORMATION: Modified CDR

<400> SEQUENCE: 101

Gly Gly Phe Thr Met Asp
1               5

<210> SEQ ID NO 102
<211> LENGTH: 6
<212> TYPE: PRT
<213> ORGANISM: Artificial Sequence
<220> FEATURE:
<223> OTHER INFORMATION: Modified CDR

<400> SEQUENCE: 102

Ala Thr Gln Thr Pro Arg
1               5

<210> SEQ ID NO 103
<211> LENGTH: 16
<212> TYPE: PRT
<213> ORGANISM: Artificial Sequence
<220> FEATURE:
<223> OTHER INFORMATION: Modified CDR

<400> SEQUENCE: 103

Ile Asn Pro Val Asp Gly Asp Thr Arg Tyr Asn Pro Ser Phe Gln Gly
1               5                   10                  15

<210> SEQ ID NO 104
<211> LENGTH: 13
<212> TYPE: PRT
<213> ORGANISM: Artificial Sequence
<220> FEATURE:
<223> OTHER INFORMATION: Modified CDR

<400> SEQUENCE: 104

Ser Ser Gln Ser Leu Leu His Ser Gln Gly Tyr Thr Tyr
1               5                   10

<210> SEQ ID NO 105
<211> LENGTH: 6
<212> TYPE: PRT
<213> ORGANISM: Artificial Sequence
<220> FEATURE:
<223> OTHER INFORMATION: Modified CDR

<400> SEQUENCE: 105

Gln Thr His Thr Pro Arg
1               5

<210> SEQ ID NO 106
<211> LENGTH: 13
<212> TYPE: PRT
```

```
<213> ORGANISM: Artificial Sequence
<220> FEATURE:
<223> OTHER INFORMATION: Modified CDR

<400> SEQUENCE: 106

Ser Ser Gln Ser Leu Leu His Ser Ser Gly Tyr Asn Tyr
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Modified CDR

<400> SEQUENCE: 107

Ser Ser Gln Ser Leu Leu His Ser Gly Gly Tyr Asn Tyr
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Modified CDR

<400> SEQUENCE: 108

Ser Ser Gln Ser Leu Leu His Ser Ala Gly Tyr Asn Tyr
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Modified CDR

<400> SEQUENCE: 109

Ser Ser Gln Ser Leu Leu His Ser Thr Gly Tyr Asn Tyr
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Modified CDR

<400> SEQUENCE: 110

Ser Ser Gln Ser Leu Leu His Ser Asn Ala Tyr Asn Tyr
1               5                   10

<210> SEQ ID NO 111
<211> LENGTH: 19
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (12)..(12)
<223> OTHER INFORMATION: N/R
<220> FEATURE:
<221> NAME/KEY: VARIANT
<222> LOCATION: (14)..(14)
<223> OTHER INFORMATION: N/S

<400> SEQUENCE: 111
```

```
Met Gly Ile Ile Asn Pro Val Asp Gly Asp Thr Xaa Tyr Xaa Pro Ser
1               5                   10                  15

Phe Gln Gly

<210> SEQ ID NO 112
<211> LENGTH: 16
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (10)..(10)
<223> OTHER INFORMATION: N/A
<220> FEATURE:
<221> NAME/KEY: VARIANT
<222> LOCATION: (13)..(13)
<223> OTHER INFORMATION: N/T

<400> SEQUENCE: 112

Arg Ser Ser Gln Ser Leu Leu His Ser Xaa Gly Tyr Xaa Tyr Leu His
1               5                   10                  15

<210> SEQ ID NO 113
<211> LENGTH: 7
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (6)..(6)
<223> OTHER INFORMATION: L/F

<400> SEQUENCE: 113

Lys Val Ser Asn Arg Xaa Ser
1               5

<210> SEQ ID NO 114
<211> LENGTH: 16
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (9)..(9)
<223> OTHER INFORMATION: N/R
<220> FEATURE:
<221> NAME/KEY: VARIANT
<222> LOCATION: (11)..(11)
<223> OTHER INFORMATION: N/S

<400> SEQUENCE: 114

Ile Asn Pro Val Asp Gly Asp Thr Xaa Tyr Xaa Pro Ser Phe Gln Gly
1               5                   10                  15

<210> SEQ ID NO 115
<211> LENGTH: 13
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (9)..(9)
<223> OTHER INFORMATION: N/A
<220> FEATURE:
<221> NAME/KEY: VARIANT
<222> LOCATION: (12)..(12)
<223> OTHER INFORMATION: N/T
```

<400> SEQUENCE: 115

Ser Ser Gln Ser Leu Leu His Ser Xaa Gly Tyr Xaa Tyr
1               5                   10

<210> SEQ ID NO 116
<211> LENGTH: 9
<212> TYPE: PRT
<213> ORGANISM: Mus musculus

<400> SEQUENCE: 116

Leu Val His Ser Asn Gly Asn Thr Tyr
1               5

<210> SEQ ID NO 117
<211> LENGTH: 9
<212> TYPE: PRT
<213> ORGANISM: Mus musculus

<400> SEQUENCE: 117

Leu Leu Ile Tyr Lys Val Ser Tyr Arg
1               5

<210> SEQ ID NO 118
<211> LENGTH: 9
<212> TYPE: PRT
<213> ORGANISM: Mus musculus

<400> SEQUENCE: 118

Tyr Arg Phe Ser Gly Val Pro Asp Arg
1               5

<210> SEQ ID NO 119
<211> LENGTH: 9
<212> TYPE: PRT
<213> ORGANISM: Mus musculus

<400> SEQUENCE: 119

Leu Ile Tyr Lys Val Ser Tyr Arg Phe
1               5

<210> SEQ ID NO 120
<211> LENGTH: 16
<212> TYPE: PRT
<213> ORGANISM: Mus musculus

<400> SEQUENCE: 120

Leu Leu Ile Tyr Lys Val Ser Tyr Arg Phe Ser Gly Val Pro Asp Arg
1               5                   10                  15

<210> SEQ ID NO 121
<211> LENGTH: 9
<212> TYPE: PRT
<213> ORGANISM: Mus musculus

<400> SEQUENCE: 121

Val Gly Val Tyr Tyr Cys Phe Gln Asn
1               5

<210> SEQ ID NO 122
<211> LENGTH: 15
<212> TYPE: PRT
<213> ORGANISM: Artificial Sequence
<220> FEATURE:
<223> OTHER INFORMATION: Modified CDR

<400> SEQUENCE: 122

Ala Gly Val Tyr Tyr Cys Phe Gln Asn Thr His Thr Pro Arg Thr
1               5                   10                  15

<210> SEQ ID NO 123
<211> LENGTH: 19
<212> TYPE: PRT
<213> ORGANISM: Mus musculus

<400> SEQUENCE: 123

Ile Gly Asp Ile Asn Pro Val Asn Gly Asp Thr Asn Phe Asn Glu Lys
1               5                   10                  15

Phe Lys Asn

<210> SEQ ID NO 124
<211> LENGTH: 5
<212> TYPE: PRT
<213> ORGANISM: Mus musculus

<400> SEQUENCE: 124

Asn Tyr Tyr Val Phe
1               5

<210> SEQ ID NO 125
<211> LENGTH: 17
<212> TYPE: PRT
<213> ORGANISM: Mus musculus

<400> SEQUENCE: 125

Asp Ile Asn Pro Val Asn Gly Asp Thr Asn Phe Asn Glu Lys Phe Lys
1               5                   10                  15

Asn

<210> SEQ ID NO 126
<211> LENGTH: 7
<212> TYPE: PRT
<213> ORGANISM: Mus musculus

<400> SEQUENCE: 126

Gly Tyr Thr Phe Thr Asn Tyr
1               5

<210> SEQ ID NO 127
<211> LENGTH: 6
<212> TYPE: PRT
<213> ORGANISM: Mus musculus

<400> SEQUENCE: 127

Asn Pro Val Asn Gly Asp
1               5

<210> SEQ ID NO 128
<211> LENGTH: 8
<212> TYPE: PRT
<213> ORGANISM: Mus musculus

<400> SEQUENCE: 128

Gly Tyr Thr Phe Thr Asn Tyr Tyr
1               5

<210> SEQ ID NO 129
<211> LENGTH: 8

```
<212> TYPE: PRT
<213> ORGANISM: Mus musculus

<400> SEQUENCE: 129

Ile Asn Pro Val Asn Gly Asp Thr
1               5

<210> SEQ ID NO 130
<211> LENGTH: 9
<212> TYPE: PRT
<213> ORGANISM: Mus musculus

<400> SEQUENCE: 130

Thr Arg Gly Gly Tyr Thr Met Asp Tyr
1               5

<210> SEQ ID NO 131
<211> LENGTH: 11
<212> TYPE: PRT
<213> ORGANISM: Mus musculus

<400> SEQUENCE: 131

Gln Ser Leu Val His Ser Asn Gly Asn Thr Tyr
1               5                   10

<210> SEQ ID NO 132
<211> LENGTH: 16
<212> TYPE: PRT
<213> ORGANISM: Mus musculus

<400> SEQUENCE: 132

Ile Asn Pro Val Asn Gly Asp Thr Asn Phe Asn Glu Lys Phe Lys Asn
1               5                   10                  15

<210> SEQ ID NO 133
<211> LENGTH: 10
<212> TYPE: PRT
<213> ORGANISM: Mus musculus

<400> SEQUENCE: 133

Asp Ile Asn Pro Val Asn Gly Asp Thr Asn
1               5                   10

<210> SEQ ID NO 134
<211> LENGTH: 6
<212> TYPE: PRT
<213> ORGANISM: Mus musculus

<400> SEQUENCE: 134

Thr Asn Tyr Tyr Val Phe
1               5

<210> SEQ ID NO 135
<211> LENGTH: 12
<212> TYPE: PRT
<213> ORGANISM: Mus musculus

<400> SEQUENCE: 135

Ile Gly Asp Ile Asn Pro Val Asn Gly Asp Thr Asn
1               5                   10

<210> SEQ ID NO 136
<211> LENGTH: 8
<212> TYPE: PRT
<213> ORGANISM: Mus musculus
```

<400> SEQUENCE: 136

Thr Arg Gly Gly Tyr Thr Met Asp
1               5

<210> SEQ ID NO 137
<211> LENGTH: 11
<212> TYPE: PRT
<213> ORGANISM: Mus musculus

<400> SEQUENCE: 137

His Ser Asn Gly Asn Thr Tyr Leu His Trp Tyr
1               5                   10

<210> SEQ ID NO 138
<211> LENGTH: 10
<212> TYPE: PRT
<213> ORGANISM: Mus musculus

<400> SEQUENCE: 138

Leu Leu Ile Tyr Lys Val Ser Tyr Arg Phe
1               5                   10

<210> SEQ ID NO 139
<211> LENGTH: 8
<212> TYPE: PRT
<213> ORGANISM: Mus musculus

<400> SEQUENCE: 139

Ser Gln Asn Thr His Val Pro Arg
1               5

<210> SEQ ID NO 140
<211> LENGTH: 116
<212> TYPE: PRT
<213> ORGANISM: Mus musculus
<220> FEATURE:
<221> NAME/KEY: DOMAIN
<222> LOCATION: (1)..(116)
<223> OTHER INFORMATION: VH DOMAIN

<400> SEQUENCE: 140

Glu Val Gln Leu Gln Gln Phe Gly Ala Glu Leu Val Lys Pro Gly Ala
1               5                   10                  15

Ser Met Lys Leu Ser Cys Lys Ala Ser Gly Tyr Thr Phe Thr Asn Tyr
                20                  25                  30

Tyr Val Phe Trp Val Lys Gln Arg Pro Gly Gln Gly Leu Glu Trp Ile
            35                  40                  45

Gly Asp Ile Asn Pro Val Asn Gly Asp Thr Asn Phe Asn Glu Lys Phe
    50                  55                  60

Lys Asn Lys Ala Thr Leu Thr Val Asp Lys Ser Ser Thr Thr Thr Tyr
65                  70                  75                  80

Leu Gln Leu Ser Ser Leu Thr Ser Glu Asp Ser Ala Val Tyr Tyr Cys
                85                  90                  95

Thr Arg Gly Gly Tyr Thr Met Asp Tyr Trp Gly Gln Gly Thr Leu Val
            100                 105                 110

Thr Val Ser Ser
        115

<210> SEQ ID NO 141
<211> LENGTH: 116
<212> TYPE: PRT

<213> ORGANISM: Artificial Sequence
<220> FEATURE:
<223> OTHER INFORMATION: VH DOMAIN

<400> SEQUENCE: 141

```
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Thr Phe Thr Asn Tyr
            20                  25                  30
Tyr Val Phe Trp Val Arg Gln Met Pro Gly Lys Gly Leu Glu Trp Ile
        35                  40                  45
Gly Asp Ile Asn Pro Val Asn Gly Asp Thr Asn Phe Asn Glu Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Gly Gly Tyr Thr Met Asp Tyr Trp Gly Gln Gly Thr Leu Val
            100                 105                 110
Thr Val Ser Ser
        115
```

<210> SEQ ID NO 142
<211> LENGTH: 112
<212> TYPE: PRT
<213> ORGANISM: Mus musculus
<220> FEATURE:
<221> NAME/KEY: DOMAIN
<222> LOCATION: (1)..(112)
<223> OTHER INFORMATION: VL DOMAIN

<400> SEQUENCE: 142

```
Asp Val Val Met Thr Gln Thr Pro Leu Ser Leu Ser Val Ser Leu Gly
1               5                   10                  15
Asp Gln Ala Ser Ile Ser Cys Arg Ser Ser Gln Ser Leu Val His Ser
            20                  25                  30
Asn Gly Asn Thr Tyr Leu His Trp Tyr Leu Gln Lys Pro Gly Gln Ser
        35                  40                  45
Pro Lys Leu Leu Ile Tyr Lys Val Ser Tyr Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Asn
                85                  90                  95
Thr His Val Pro Arg Thr Phe Gly Gln Gly Thr Lys Val Glu Ile Lys
            100                 105                 110
```

<210> SEQ ID NO 143
<211> LENGTH: 112
<212> TYPE: PRT
<213> ORGANISM: Artificial Sequence
<220> FEATURE:
<223> OTHER INFORMATION: VL DOMAIN

<400> SEQUENCE: 143

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val His Ser
            20                  25                  30
```

-continued

Asn Gly Asn Thr Tyr Leu His Trp Tyr Leu Gln Lys Pro Gly Gln Ser
            35                  40                  45

Pro Gln Leu Leu Ile Tyr Lys Val Ser Tyr Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly Thr Lys Val Glu Ile Lys
            100                 105                 110

<210> SEQ ID NO 144
<211> LENGTH: 16
<212> TYPE: PRT
<213> ORGANISM: Artificial Sequence
<220> FEATURE:
<223> OTHER INFORMATION: Modified CDR

<400> SEQUENCE: 144

Arg Ser Ser His Ser Leu Val His Ser Asn Gly Asn Thr Tyr Leu His
1               5                   10                  15

<210> SEQ ID NO 145
<211> LENGTH: 10
<212> TYPE: PRT
<213> ORGANISM: Artificial Sequence
<220> FEATURE:
<223> OTHER INFORMATION: Modified CDR

<400> SEQUENCE: 145

Gly Tyr Asn Phe Thr Asn Tyr Tyr Ile Phe
1               5                   10

<210> SEQ ID NO 146
<211> LENGTH: 19
<212> TYPE: PRT
<213> ORGANISM: Artificial Sequence
<220> FEATURE:
<223> OTHER INFORMATION: Modified CDR

<400> SEQUENCE: 146

Met Gly Asp Ile Asn Pro Phe Asn Gly Asp Thr Asn Phe Asn Pro Ser
1               5                   10                  15

Phe Gln Gly

<210> SEQ ID NO 147
<211> LENGTH: 16
<212> TYPE: PRT
<213> ORGANISM: Artificial Sequence
<220> FEATURE:
<223> OTHER INFORMATION: Modified CDR

<400> SEQUENCE: 147

Arg Ser Ser Gln Ser Phe Leu His Ser Asn Gly Asn Asn Tyr Leu His
1               5                   10                  15

<210> SEQ ID NO 148
<211> LENGTH: 9
<212> TYPE: PRT
<213> ORGANISM: Artificial Sequence
<220> FEATURE:
<223> OTHER INFORMATION: Modified CDR

<400> SEQUENCE: 148

Leu Gln Asn Thr His Thr Pro Arg Thr
1               5

<210> SEQ ID NO 149
<211> LENGTH: 10
<212> TYPE: PRT
<213> ORGANISM: Artificial Sequence
<220> FEATURE:
<223> OTHER INFORMATION: Modified CDR

<400> SEQUENCE: 149

Gly Tyr Arg Phe Thr Asn Tyr Tyr Ile Phe
1               5                   10

<210> SEQ ID NO 150
<211> LENGTH: 19
<212> TYPE: PRT
<213> ORGANISM: Artificial Sequence
<220> FEATURE:
<223> OTHER INFORMATION: Modified CDR

<400> SEQUENCE: 150

Met Gly Asp Ile Asn Pro Gly Asp Gly Asp Thr Asn Phe Asn Pro Ser
1               5                   10                  15

Phe Gln Gly

<210> SEQ ID NO 151
<211> LENGTH: 7
<212> TYPE: PRT
<213> ORGANISM: Artificial Sequence
<220> FEATURE:
<223> OTHER INFORMATION: Modified CDR

<400> SEQUENCE: 151

Gly Gly His Thr Met Asp Tyr
1               5

<210> SEQ ID NO 152
<211> LENGTH: 16
<212> TYPE: PRT
<213> ORGANISM: Artificial Sequence
<220> FEATURE:
<223> OTHER INFORMATION: Modified CDR

<400> SEQUENCE: 152

Arg Ser Ser Gln Ser Leu Leu His Ser Asn Gly Asn Asn Tyr Leu Asp
1               5                   10                  15

<210> SEQ ID NO 153
<211> LENGTH: 7
<212> TYPE: PRT
<213> ORGANISM: Artificial Sequence
<220> FEATURE:
<223> OTHER INFORMATION: Modified CDR

<400> SEQUENCE: 153

Lys Gly Ser Asn Arg Ser Ser
1               5

<210> SEQ ID NO 154
<211> LENGTH: 9
<212> TYPE: PRT
<213> ORGANISM: Artificial Sequence
<220> FEATURE:
<223> OTHER INFORMATION: Modified CDR

<400> SEQUENCE: 154

```
Met Gln Ala Leu His Thr Pro Trp Thr
1               5

<210> SEQ ID NO 155
<211> LENGTH: 10
<212> TYPE: PRT
<213> ORGANISM: Artificial Sequence
<220> FEATURE:
<223> OTHER INFORMATION: Modified CDR

<400> SEQUENCE: 155

Gly Tyr Arg Phe Thr Asn Tyr Tyr Val Phe
1               5                   10

<210> SEQ ID NO 156
<211> LENGTH: 19
<212> TYPE: PRT
<213> ORGANISM: Artificial Sequence
<220> FEATURE:
<223> OTHER INFORMATION: Modified CDR

<400> SEQUENCE: 156

Met Gly Asp Ile Asn Pro Gly Asn Gly Asp Thr Asn Phe Asn Pro Ser
1               5                   10                  15

Phe Gln Gly

<210> SEQ ID NO 157
<211> LENGTH: 7
<212> TYPE: PRT
<213> ORGANISM: Artificial Sequence
<220> FEATURE:
<223> OTHER INFORMATION: Modified CDR

<400> SEQUENCE: 157

Gly Gly Ile Thr Met Asp Tyr
1               5

<210> SEQ ID NO 158
<211> LENGTH: 16
<212> TYPE: PRT
<213> ORGANISM: Artificial Sequence
<220> FEATURE:
<223> OTHER INFORMATION: Modified CDR

<400> SEQUENCE: 158

Arg Ser Ser Gln Ser Leu Leu His Ser Asn Gly Asn Asn Tyr Leu His
1               5                   10                  15

<210> SEQ ID NO 159
<211> LENGTH: 9
<212> TYPE: PRT
<213> ORGANISM: Artificial Sequence
<220> FEATURE:
<223> OTHER INFORMATION: Modified CDR

<400> SEQUENCE: 159

Met Gln Ala Leu His Val Pro Arg Thr
1               5

<210> SEQ ID NO 160
<211> LENGTH: 10
<212> TYPE: PRT
<213> ORGANISM: Artificial Sequence
<220> FEATURE:
<223> OTHER INFORMATION: Modified CDR
```

```
<400> SEQUENCE: 160

Gly Tyr Ser Phe Asn Asn Tyr Tyr Ile Phe
1               5                   10

<210> SEQ ID NO 161
<211> LENGTH: 19
<212> TYPE: PRT
<213> ORGANISM: Artificial Sequence
<220> FEATURE:
<223> OTHER INFORMATION: Modified CDR

<400> SEQUENCE: 161

Met Gly Asp Ile Asn Pro Gly Asn Gly Asp Thr Asn Tyr Asn Pro Ser
1               5                   10                  15

Phe Gln Gly

<210> SEQ ID NO 162
<211> LENGTH: 7
<212> TYPE: PRT
<213> ORGANISM: Artificial Sequence
<220> FEATURE:
<223> OTHER INFORMATION: Modified CDR

<400> SEQUENCE: 162

Gly Gly Gln Thr Met Asp Gln
1               5

<210> SEQ ID NO 163
<211> LENGTH: 16
<212> TYPE: PRT
<213> ORGANISM: Artificial Sequence
<220> FEATURE:
<223> OTHER INFORMATION: Modified CDR

<400> SEQUENCE: 163

Arg Ser Ser Gln Ser Leu Leu His Ser Asn Gly Asn Thr Tyr Leu Asp
1               5                   10                  15

<210> SEQ ID NO 164
<211> LENGTH: 9
<212> TYPE: PRT
<213> ORGANISM: Artificial Sequence
<220> FEATURE:
<223> OTHER INFORMATION: Modified CDR

<400> SEQUENCE: 164

Met Gln Ala Leu Gln Val Pro Trp Thr
1               5

<210> SEQ ID NO 165
<211> LENGTH: 19
<212> TYPE: PRT
<213> ORGANISM: Artificial Sequence
<220> FEATURE:
<223> OTHER INFORMATION: Modified CDR

<400> SEQUENCE: 165

Met Gly Asp Ile Asn Pro Gly Asn Gly Asp Thr Asn Tyr Ser Pro Ser
1               5                   10                  15

Phe Gln Gly

<210> SEQ ID NO 166
<211> LENGTH: 7
<212> TYPE: PRT
<213> ORGANISM: Artificial Sequence
```

```
<220> FEATURE:
<223> OTHER INFORMATION: Modified CDR

<400> SEQUENCE: 166

Gly Gly Tyr Ile Met Asp Tyr
1               5

<210> SEQ ID NO 167
<211> LENGTH: 16
<212> TYPE: PRT
<213> ORGANISM: Artificial Sequence
<220> FEATURE:
<223> OTHER INFORMATION: Modified CDR

<400> SEQUENCE: 167

Arg Ser Ser Gln Ser Leu Leu His Ser Asn Gly Asn Thr Tyr Leu His
1               5                   10                  15

<210> SEQ ID NO 168
<211> LENGTH: 7
<212> TYPE: PRT
<213> ORGANISM: Artificial Sequence
<220> FEATURE:
<223> OTHER INFORMATION: Modified CDR

<400> SEQUENCE: 168

Lys Gly Ser Tyr Arg Leu Ser
1               5

<210> SEQ ID NO 169
<211> LENGTH: 9
<212> TYPE: PRT
<213> ORGANISM: Artificial Sequence
<220> FEATURE:
<223> OTHER INFORMATION: Modified CDR

<400> SEQUENCE: 169

Met Gln Ala Thr His Val Pro Trp Thr
1               5

<210> SEQ ID NO 170
<211> LENGTH: 10
<212> TYPE: PRT
<213> ORGANISM: Artificial Sequence
<220> FEATURE:
<223> OTHER INFORMATION: Modified CDR

<400> SEQUENCE: 170

Gly Tyr Ser Phe Thr Ser Tyr Tyr Ile Phe
1               5                   10

<210> SEQ ID NO 171
<211> LENGTH: 19
<212> TYPE: PRT
<213> ORGANISM: Artificial Sequence
<220> FEATURE:
<223> OTHER INFORMATION: Modified CDR

<400> SEQUENCE: 171

Met Gly Asp Ile Asn Pro Gly Asn Gly Asp Thr Arg Phe Asn Pro Ser
1               5                   10                  15

Phe Gln Gly

<210> SEQ ID NO 172
<211> LENGTH: 7
<212> TYPE: PRT
```

<213> ORGANISM: Artificial Sequence
<220> FEATURE:
<223> OTHER INFORMATION: Modified CDR

<400> SEQUENCE: 172

Gly Gly Tyr Thr Ala Asp Tyr
1               5

<210> SEQ ID NO 173
<211> LENGTH: 16
<212> TYPE: PRT
<213> ORGANISM: Artificial Sequence
<220> FEATURE:
<223> OTHER INFORMATION: Modified CDR

<400> SEQUENCE: 173

Arg Ser Ser Gln Ser Leu Leu His Ser Asn Gly Ser Asn Tyr Leu His
1               5                   10                  15

<210> SEQ ID NO 174
<211> LENGTH: 7
<212> TYPE: PRT
<213> ORGANISM: Artificial Sequence
<220> FEATURE:
<223> OTHER INFORMATION: Modified CDR

<400> SEQUENCE: 174

Lys Val Ser Asn Arg Ala Ser
1               5

<210> SEQ ID NO 175
<211> LENGTH: 9
<212> TYPE: PRT
<213> ORGANISM: Artificial Sequence
<220> FEATURE:
<223> OTHER INFORMATION: Modified CDR

<400> SEQUENCE: 175

Met Gln Ala Thr Gln Val Pro Trp Thr
1               5

<210> SEQ ID NO 176
<211> LENGTH: 10
<212> TYPE: PRT
<213> ORGANISM: Artificial Sequence
<220> FEATURE:
<223> OTHER INFORMATION: Modified CDR

<400> SEQUENCE: 176

Gly Tyr Ser Phe Thr Ser Tyr Tyr Ile Val
1               5                   10

<210> SEQ ID NO 177
<211> LENGTH: 19
<212> TYPE: PRT
<213> ORGANISM: Artificial Sequence
<220> FEATURE:
<223> OTHER INFORMATION: Modified CDR

<400> SEQUENCE: 177

Met Gly Asp Ile Asn Pro Gly Asn Gly Asp Thr Arg Phe Ser Pro Ser
1               5                   10                  15

Phe Gln Gly

<210> SEQ ID NO 178
<211> LENGTH: 7

```
<212> TYPE: PRT
<213> ORGANISM: Artificial Sequence
<220> FEATURE:
<223> OTHER INFORMATION: Modified CDR

<400> SEQUENCE: 178

Gly Gly Tyr Thr Leu Asp Tyr
1               5

<210> SEQ ID NO 179
<211> LENGTH: 9
<212> TYPE: PRT
<213> ORGANISM: Artificial Sequence
<220> FEATURE:
<223> OTHER INFORMATION: Modified CDR

<400> SEQUENCE: 179

Met Gln Asn Leu Gln Thr Pro Arg Thr
1               5

<210> SEQ ID NO 180
<211> LENGTH: 10
<212> TYPE: PRT
<213> ORGANISM: Artificial Sequence
<220> FEATURE:
<223> OTHER INFORMATION: Modified CDR

<400> SEQUENCE: 180

Gly Tyr Ser Phe Thr Ser Tyr Tyr Val Phe
1               5                   10

<210> SEQ ID NO 181
<211> LENGTH: 19
<212> TYPE: PRT
<213> ORGANISM: Artificial Sequence
<220> FEATURE:
<223> OTHER INFORMATION: Modified CDR

<400> SEQUENCE: 181

Met Gly Asp Ile Asn Pro Gly Asn Gly Asp Thr Arg Tyr Asn Pro Ser
1               5                   10                  15

Phe Gln Gly

<210> SEQ ID NO 182
<211> LENGTH: 7
<212> TYPE: PRT
<213> ORGANISM: Artificial Sequence
<220> FEATURE:
<223> OTHER INFORMATION: Modified CDR

<400> SEQUENCE: 182

Gly Gly Tyr Thr Met Asp Ala
1               5

<210> SEQ ID NO 183
<211> LENGTH: 16
<212> TYPE: PRT
<213> ORGANISM: Artificial Sequence
<220> FEATURE:
<223> OTHER INFORMATION: Modified CDR

<400> SEQUENCE: 183

Arg Ser Ser Gln Ser Leu Leu His Ser Asn Gly Tyr Thr Tyr Leu Asp
1               5                   10                  15

<210> SEQ ID NO 184
```

```
<211> LENGTH: 9
<212> TYPE: PRT
<213> ORGANISM: Artificial Sequence
<220> FEATURE:
<223> OTHER INFORMATION: Modified CDR

<400> SEQUENCE: 184

Met Gln Asn Thr His Ile Pro Arg Thr
1               5

<210> SEQ ID NO 185
<211> LENGTH: 10
<212> TYPE: PRT
<213> ORGANISM: Artificial Sequence
<220> FEATURE:
<223> OTHER INFORMATION: Modified CDR

<400> SEQUENCE: 185

Gly Tyr Ser Phe Thr Ser Tyr Tyr Val Gly
1               5                   10

<210> SEQ ID NO 186
<211> LENGTH: 19
<212> TYPE: PRT
<213> ORGANISM: Artificial Sequence
<220> FEATURE:
<223> OTHER INFORMATION: Modified CDR

<400> SEQUENCE: 186

Met Gly Asp Ile Asn Pro Gly Asn Gly Asp Thr Arg Tyr Ser Pro Ser
1               5                   10                  15

Phe Gln Gly

<210> SEQ ID NO 187
<211> LENGTH: 7
<212> TYPE: PRT
<213> ORGANISM: Artificial Sequence
<220> FEATURE:
<223> OTHER INFORMATION: Modified CDR

<400> SEQUENCE: 187

Gly Gly Tyr Thr Met Asp Glu
1               5

<210> SEQ ID NO 188
<211> LENGTH: 7
<212> TYPE: PRT
<213> ORGANISM: Artificial Sequence
<220> FEATURE:
<223> OTHER INFORMATION: Modified CDR

<400> SEQUENCE: 188

Lys Val Ser Tyr Arg Ala Ser
1               5

<210> SEQ ID NO 189
<211> LENGTH: 9
<212> TYPE: PRT
<213> ORGANISM: Artificial Sequence
<220> FEATURE:
<223> OTHER INFORMATION: Modified CDR

<400> SEQUENCE: 189

Met Gln Asn Thr His Thr Leu Arg Thr
1               5
```

```
<210> SEQ ID NO 190
<211> LENGTH: 19
<212> TYPE: PRT
<213> ORGANISM: Artificial Sequence
<220> FEATURE:
<223> OTHER INFORMATION: Modified CDR

<400> SEQUENCE: 190

Met Gly Asp Ile Asn Pro Gly Asn Ser Asp Thr Asn Phe Asn Pro Ser
1               5                   10                  15
Phe Gln Gly

<210> SEQ ID NO 191
<211> LENGTH: 7
<212> TYPE: PRT
<213> ORGANISM: Artificial Sequence
<220> FEATURE:
<223> OTHER INFORMATION: Modified CDR

<400> SEQUENCE: 191

Gly Gly Tyr Thr Met Asp Phe
1               5

<210> SEQ ID NO 192
<211> LENGTH: 16
<212> TYPE: PRT
<213> ORGANISM: Artificial Sequence
<220> FEATURE:
<223> OTHER INFORMATION: Modified CDR

<400> SEQUENCE: 192

Arg Ser Ser Gln Ser Leu Val His Ser Asn Gly Asn Asn Tyr Leu Asp
1               5                   10                  15

<210> SEQ ID NO 193
<211> LENGTH: 7
<212> TYPE: PRT
<213> ORGANISM: Artificial Sequence
<220> FEATURE:
<223> OTHER INFORMATION: Modified CDR

<400> SEQUENCE: 193

Lys Val Ser Tyr Arg Leu Ser
1               5

<210> SEQ ID NO 194
<211> LENGTH: 9
<212> TYPE: PRT
<213> ORGANISM: Artificial Sequence
<220> FEATURE:
<223> OTHER INFORMATION: Modified CDR

<400> SEQUENCE: 194

Met Gln Asn Thr His Thr Pro Arg Thr
1               5

<210> SEQ ID NO 195
<211> LENGTH: 10
<212> TYPE: PRT
<213> ORGANISM: Artificial Sequence
<220> FEATURE:
<223> OTHER INFORMATION: Modified CDR

<400> SEQUENCE: 195

Gly Tyr Thr Phe Thr Ser Tyr Tyr Ile Phe
1               5                   10
```

<210> SEQ ID NO 196
<211> LENGTH: 19
<212> TYPE: PRT
<213> ORGANISM: Artificial Sequence
<220> FEATURE:
<223> OTHER INFORMATION: Modified CDR

<400> SEQUENCE: 196

Met Gly Asp Ile Asn Pro Gly Asn Ser Asp Thr Asn Tyr Asn Pro Ser
1               5                   10                  15

Phe Gln Gly

<210> SEQ ID NO 197
<211> LENGTH: 7
<212> TYPE: PRT
<213> ORGANISM: Artificial Sequence
<220> FEATURE:
<223> OTHER INFORMATION: Modified CDR

<400> SEQUENCE: 197

Gly Gly Tyr Thr Met Asp His
1               5

<210> SEQ ID NO 198
<211> LENGTH: 9
<212> TYPE: PRT
<213> ORGANISM: Artificial Sequence
<220> FEATURE:
<223> OTHER INFORMATION: Modified CDR

<400> SEQUENCE: 198

Met Gln Asn Thr His Val Pro Arg Thr
1               5

<210> SEQ ID NO 199
<211> LENGTH: 10
<212> TYPE: PRT
<213> ORGANISM: Artificial Sequence
<220> FEATURE:
<223> OTHER INFORMATION: Modified CDR

<400> SEQUENCE: 199

Gly Tyr Thr Phe Thr Ser Tyr Val Phe
1               5                   10

<210> SEQ ID NO 200
<211> LENGTH: 19
<212> TYPE: PRT
<213> ORGANISM: Artificial Sequence
<220> FEATURE:
<223> OTHER INFORMATION: Modified CDR

<400> SEQUENCE: 200

Met Gly Asp Ile Asn Pro Val Asp Gly Asp Thr Lys Tyr Asn Pro Ser
1               5                   10                  15

Phe Gln Gly

<210> SEQ ID NO 201
<211> LENGTH: 16
<212> TYPE: PRT
<213> ORGANISM: Artificial Sequence
<220> FEATURE:
<223> OTHER INFORMATION: Modified CDR

<400> SEQUENCE: 201

```
Arg Ser Ser Gln Ser Leu Val His Ser Asn Gly Asn Asn Tyr Leu His
1               5                   10                  15
```

<210> SEQ ID NO 202
<211> LENGTH: 9
<212> TYPE: PRT
<213> ORGANISM: Artificial Sequence
<220> FEATURE:
<223> OTHER INFORMATION: Modified CDR

<400> SEQUENCE: 202

```
Met Gln Asn Thr Gln Thr Pro Arg Thr
1               5
```

<210> SEQ ID NO 203
<211> LENGTH: 19
<212> TYPE: PRT
<213> ORGANISM: Artificial Sequence
<220> FEATURE:
<223> OTHER INFORMATION: Modified CDR

<400> SEQUENCE: 203

```
Met Gly Asp Ile Asn Pro Val Asp Gly Asp Thr Asn Phe Asn Pro Ser
1               5                   10                  15

Phe Gln Gly
```

<210> SEQ ID NO 204
<211> LENGTH: 9
<212> TYPE: PRT
<213> ORGANISM: Artificial Sequence
<220> FEATURE:
<223> OTHER INFORMATION: Modified CDR

<400> SEQUENCE: 204

```
Met Gln Thr Thr His Thr Pro Arg Thr
1               5
```

<210> SEQ ID NO 205
<211> LENGTH: 19
<212> TYPE: PRT
<213> ORGANISM: Artificial Sequence
<220> FEATURE:
<223> OTHER INFORMATION: Modified CDR

<400> SEQUENCE: 205

```
Met Gly Asp Ile Asn Pro Val Asp Gly Asp Thr Asn Phe Ser Pro Ser
1               5                   10                  15

Phe Gln Gly
```

<210> SEQ ID NO 206
<211> LENGTH: 7
<212> TYPE: PRT
<213> ORGANISM: Artificial Sequence
<220> FEATURE:
<223> OTHER INFORMATION: Modified CDR

<400> SEQUENCE: 206

```
Gly Gly Tyr Thr Met Asp Leu
1               5
```

<210> SEQ ID NO 207
<211> LENGTH: 16
<212> TYPE: PRT
<213> ORGANISM: Artificial Sequence
<220> FEATURE:
<223> OTHER INFORMATION: Modified CDR

```
<400> SEQUENCE: 207

Arg Ser Ser Gln Ser Leu Val His Ser Asn Gly Tyr Asn Tyr Leu His
1               5                   10                  15

<210> SEQ ID NO 208
<211> LENGTH: 7
<212> TYPE: PRT
<213> ORGANISM: Artificial Sequence
<220> FEATURE:
<223> OTHER INFORMATION: Modified CDR

<400> SEQUENCE: 208

Leu Gly Ser Tyr Arg Ala Ser
1               5

<210> SEQ ID NO 209
<211> LENGTH: 9
<212> TYPE: PRT
<213> ORGANISM: Artificial Sequence
<220> FEATURE:
<223> OTHER INFORMATION: Modified CDR

<400> SEQUENCE: 209

Met Gln Thr Thr Gln Ile Pro Arg Thr
1               5

<210> SEQ ID NO 210
<211> LENGTH: 19
<212> TYPE: PRT
<213> ORGANISM: Artificial Sequence
<220> FEATURE:
<223> OTHER INFORMATION: Modified CDR

<400> SEQUENCE: 210

Met Gly Asp Ile Asn Pro Val Asp Gly Asp Thr Asn Tyr Asn Pro Ser
1               5                   10                  15

Phe Gln Gly

<210> SEQ ID NO 211
<211> LENGTH: 7
<212> TYPE: PRT
<213> ORGANISM: Artificial Sequence
<220> FEATURE:
<223> OTHER INFORMATION: Modified CDR

<400> SEQUENCE: 211

Gly Gly Tyr Thr Met Asp Met
1               5

<210> SEQ ID NO 212
<211> LENGTH: 16
<212> TYPE: PRT
<213> ORGANISM: Artificial Sequence
<220> FEATURE:
<223> OTHER INFORMATION: Modified CDR

<400> SEQUENCE: 212

Arg Ser Ser Gln Ser Leu Val His Ser Asn Gly Tyr Thr Tyr Leu Asp
1               5                   10                  15

<210> SEQ ID NO 213
<211> LENGTH: 7
<212> TYPE: PRT
<213> ORGANISM: Artificial Sequence
<220> FEATURE:
```

<223> OTHER INFORMATION: Modified CDR

<400> SEQUENCE: 213

Leu Gly Ser Tyr Arg Phe Ser
1               5

<210> SEQ ID NO 214
<211> LENGTH: 9
<212> TYPE: PRT
<213> ORGANISM: Artificial Sequence
<220> FEATURE:
<223> OTHER INFORMATION: Modified CDR

<400> SEQUENCE: 214

Ser Gln Ala Thr His Phe Pro Arg Thr
1               5

<210> SEQ ID NO 215
<211> LENGTH: 19
<212> TYPE: PRT
<213> ORGANISM: Artificial Sequence
<220> FEATURE:
<223> OTHER INFORMATION: Modified CDR

<400> SEQUENCE: 215

Met Gly Asp Ile Asn Pro Val Asp Gly Asp Thr Asn Tyr Ser Pro Ser
1               5                   10                  15

Phe Gln Gly

<210> SEQ ID NO 216
<211> LENGTH: 7
<212> TYPE: PRT
<213> ORGANISM: Artificial Sequence
<220> FEATURE:
<223> OTHER INFORMATION: Modified CDR

<400> SEQUENCE: 216

Gly Gly Tyr Thr Met Asp Asn
1               5

<210> SEQ ID NO 217
<211> LENGTH: 7
<212> TYPE: PRT
<213> ORGANISM: Artificial Sequence
<220> FEATURE:
<223> OTHER INFORMATION: Modified CDR

<400> SEQUENCE: 217

Leu Gly Ser Tyr Arg Leu Ser
1               5

<210> SEQ ID NO 218
<211> LENGTH: 19
<212> TYPE: PRT
<213> ORGANISM: Artificial Sequence
<220> FEATURE:
<223> OTHER INFORMATION: Modified CDR

<400> SEQUENCE: 218

Met Gly Asp Ile Asn Pro Val Asp Gly Asp Thr Arg Phe Asn Pro Ser
1               5                   10                  15

Phe Gln Gly

<210> SEQ ID NO 219
<211> LENGTH: 7

```
<212> TYPE: PRT
<213> ORGANISM: Artificial Sequence
<220> FEATURE:
<223> OTHER INFORMATION: Modified CDR

<400> SEQUENCE: 219

Gly Gly Tyr Thr Met Asp Gln
1               5

<210> SEQ ID NO 220
<211> LENGTH: 7
<212> TYPE: PRT
<213> ORGANISM: Artificial Sequence
<220> FEATURE:
<223> OTHER INFORMATION: Modified CDR

<400> SEQUENCE: 220

Leu Val Ser Asn Arg Ala Ser
1               5

<210> SEQ ID NO 221
<211> LENGTH: 9
<212> TYPE: PRT
<213> ORGANISM: Artificial Sequence
<220> FEATURE:
<223> OTHER INFORMATION: Modified CDR

<400> SEQUENCE: 221

Ser Gln Asn Ile Gln Thr Pro Arg Thr
1               5

<210> SEQ ID NO 222
<211> LENGTH: 19
<212> TYPE: PRT
<213> ORGANISM: Artificial Sequence
<220> FEATURE:
<223> OTHER INFORMATION: Modified CDR

<400> SEQUENCE: 222

Met Gly Asp Ile Asn Pro Val Asp Gly Asp Thr Arg Tyr Asn Pro Ser
1               5                   10                  15
Phe Gln Gly

<210> SEQ ID NO 223
<211> LENGTH: 7
<212> TYPE: PRT
<213> ORGANISM: Artificial Sequence
<220> FEATURE:
<223> OTHER INFORMATION: Modified CDR

<400> SEQUENCE: 223

Leu Val Ser Asn Arg Phe Ser
1               5

<210> SEQ ID NO 224
<211> LENGTH: 9
<212> TYPE: PRT
<213> ORGANISM: Artificial Sequence
<220> FEATURE:
<223> OTHER INFORMATION: Modified CDR

<400> SEQUENCE: 224

Ser Gln Asn Leu His Thr Pro Arg Thr
1               5

<210> SEQ ID NO 225
```

```
<211> LENGTH: 19
<212> TYPE: PRT
<213> ORGANISM: Artificial Sequence
<220> FEATURE:
<223> OTHER INFORMATION: Modified CDR

<400> SEQUENCE: 225

Met Gly Asp Ile Asn Pro Val Asp Gly Asp Thr Arg Tyr Ser Pro Ser
1               5                   10                  15
Phe Gln Gly

<210> SEQ ID NO 226
<211> LENGTH: 7
<212> TYPE: PRT
<213> ORGANISM: Artificial Sequence
<220> FEATURE:
<223> OTHER INFORMATION: Modified CDR

<400> SEQUENCE: 226

Gly Gly Tyr Thr Met Asp Thr
1               5

<210> SEQ ID NO 227
<211> LENGTH: 7
<212> TYPE: PRT
<213> ORGANISM: Artificial Sequence
<220> FEATURE:
<223> OTHER INFORMATION: Modified CDR

<400> SEQUENCE: 227

Leu Val Ser Asn Arg Leu Ser
1               5

<210> SEQ ID NO 228
<211> LENGTH: 9
<212> TYPE: PRT
<213> ORGANISM: Artificial Sequence
<220> FEATURE:
<223> OTHER INFORMATION: Modified CDR

<400> SEQUENCE: 228

Ser Gln Asn Leu Gln Thr Pro Arg Thr
1               5

<210> SEQ ID NO 229
<211> LENGTH: 19
<212> TYPE: PRT
<213> ORGANISM: Artificial Sequence
<220> FEATURE:
<223> OTHER INFORMATION: Modified CDR

<400> SEQUENCE: 229

Met Gly Asp Ile Asn Pro Val Asp Ser Asp Thr Lys Phe Asn Pro Ser
1               5                   10                  15
Phe Gln Gly

<210> SEQ ID NO 230
<211> LENGTH: 7
<212> TYPE: PRT
<213> ORGANISM: Artificial Sequence
<220> FEATURE:
<223> OTHER INFORMATION: Modified CDR

<400> SEQUENCE: 230

Gly Gly Tyr Thr Met Asp Val
1               5
```

<210> SEQ ID NO 231
<211> LENGTH: 7
<212> TYPE: PRT
<213> ORGANISM: Artificial Sequence
<220> FEATURE:
<223> OTHER INFORMATION: Modified CDR

<400> SEQUENCE: 231

Leu Val Ser Tyr Arg Ala Ser
1               5

<210> SEQ ID NO 232
<211> LENGTH: 9
<212> TYPE: PRT
<213> ORGANISM: Artificial Sequence
<220> FEATURE:
<223> OTHER INFORMATION: Modified CDR

<400> SEQUENCE: 232

Ser Gln Asn Met His Thr Pro Arg Thr
1               5

<210> SEQ ID NO 233
<211> LENGTH: 19
<212> TYPE: PRT
<213> ORGANISM: Artificial Sequence
<220> FEATURE:
<223> OTHER INFORMATION: Modified CDR

<400> SEQUENCE: 233

Met Gly Asp Ile Asn Pro Val Asp Ser Asp Thr Asn Phe Asn Pro Ser
1               5                   10                  15

Phe Gln Gly

<210> SEQ ID NO 234
<211> LENGTH: 7
<212> TYPE: PRT
<213> ORGANISM: Artificial Sequence
<220> FEATURE:
<223> OTHER INFORMATION: Modified CDR

<400> SEQUENCE: 234

Gly Gly Tyr Thr Met Asp Trp
1               5

<210> SEQ ID NO 235
<211> LENGTH: 7
<212> TYPE: PRT
<213> ORGANISM: Artificial Sequence
<220> FEATURE:
<223> OTHER INFORMATION: Modified CDR

<400> SEQUENCE: 235

Met Gly Ser Asn Arg Phe Ser
1               5

<210> SEQ ID NO 236
<211> LENGTH: 9
<212> TYPE: PRT
<213> ORGANISM: Artificial Sequence
<220> FEATURE:
<223> OTHER INFORMATION: Modified CDR

<400> SEQUENCE: 236

Ser Gln Asn Thr His Phe Pro Arg Thr

```
1               5
```

<210> SEQ ID NO 237
<211> LENGTH: 19
<212> TYPE: PRT
<213> ORGANISM: Artificial Sequence
<220> FEATURE:
<223> OTHER INFORMATION: Modified CDR

<400> SEQUENCE: 237

```
Met Gly Asp Ile Asn Pro Val Asp Ser Asp Thr Asn Tyr Asn Pro Ser
1               5                   10                  15

Phe Gln Gly
```

<210> SEQ ID NO 238
<211> LENGTH: 7
<212> TYPE: PRT
<213> ORGANISM: Artificial Sequence
<220> FEATURE:
<223> OTHER INFORMATION: Modified CDR

<400> SEQUENCE: 238

```
Met Gly Ser Tyr Arg Leu Ser
1               5
```

<210> SEQ ID NO 239
<211> LENGTH: 9
<212> TYPE: PRT
<213> ORGANISM: Artificial Sequence
<220> FEATURE:
<223> OTHER INFORMATION: Modified CDR

<400> SEQUENCE: 239

```
Ser Gln Asn Thr His Val Pro Trp Thr
1               5
```

<210> SEQ ID NO 240
<211> LENGTH: 19
<212> TYPE: PRT
<213> ORGANISM: Artificial Sequence
<220> FEATURE:
<223> OTHER INFORMATION: Modified CDR

<400> SEQUENCE: 240

```
Met Gly Asp Ile Asn Pro Val Asp Ser Asp Thr Asn Tyr Ser Pro Ser
1               5                   10                  15

Phe Gln Gly
```

<210> SEQ ID NO 241
<211> LENGTH: 7
<212> TYPE: PRT
<213> ORGANISM: Artificial Sequence
<220> FEATURE:
<223> OTHER INFORMATION: Modified CDR

<400> SEQUENCE: 241

```
Met Val Ser Asn Arg Phe Ser
1               5
```

<210> SEQ ID NO 242
<211> LENGTH: 9
<212> TYPE: PRT
<213> ORGANISM: Artificial Sequence
<220> FEATURE:
<223> OTHER INFORMATION: Modified CDR

```
<400> SEQUENCE: 242

Ser Gln Asn Thr Gln Ala Pro Arg Thr
1               5

<210> SEQ ID NO 243
<211> LENGTH: 19
<212> TYPE: PRT
<213> ORGANISM: Artificial Sequence
<220> FEATURE:
<223> OTHER INFORMATION: Modified CDR

<400> SEQUENCE: 243

Met Gly Asp Ile Asn Pro Val Asp Ser Asp Thr Arg Phe Asn Pro Ser
1               5                   10                  15

Phe Gln Gly

<210> SEQ ID NO 244
<211> LENGTH: 7
<212> TYPE: PRT
<213> ORGANISM: Artificial Sequence
<220> FEATURE:
<223> OTHER INFORMATION: Modified CDR

<400> SEQUENCE: 244

Gly Gly Tyr Thr Arg Asp Tyr
1               5

<210> SEQ ID NO 245
<211> LENGTH: 19
<212> TYPE: PRT
<213> ORGANISM: Artificial Sequence
<220> FEATURE:
<223> OTHER INFORMATION: Modified CDR

<400> SEQUENCE: 245

Met Gly Asp Ile Asn Pro Val Asp Ser Asp Thr Arg Tyr Asn Pro Ser
1               5                   10                  15

Phe Gln Gly

<210> SEQ ID NO 246
<211> LENGTH: 7
<212> TYPE: PRT
<213> ORGANISM: Artificial Sequence
<220> FEATURE:
<223> OTHER INFORMATION: Modified CDR

<400> SEQUENCE: 246

Gly Gly Tyr Thr Thr Asp Ser
1               5

<210> SEQ ID NO 247
<211> LENGTH: 9
<212> TYPE: PRT
<213> ORGANISM: Artificial Sequence
<220> FEATURE:
<223> OTHER INFORMATION: Modified CDR

<400> SEQUENCE: 247

Ser Gln Asn Thr Gln Thr Pro Trp Thr
1               5

<210> SEQ ID NO 248
<211> LENGTH: 19
<212> TYPE: PRT
<213> ORGANISM: Artificial Sequence
```

```
<220> FEATURE:
<223> OTHER INFORMATION: Modified CDR

<400> SEQUENCE: 248

Met Gly Asp Ile Asn Pro Val Asp Ser Asp Thr Arg Tyr Ser Pro Ser
1               5                   10                  15

Phe Gln Gly

<210> SEQ ID NO 249
<211> LENGTH: 7
<212> TYPE: PRT
<213> ORGANISM: Artificial Sequence
<220> FEATURE:
<223> OTHER INFORMATION: Modified CDR

<400> SEQUENCE: 249

Gly Gly Tyr Thr Thr Asp Trp
1               5

<210> SEQ ID NO 250
<211> LENGTH: 9
<212> TYPE: PRT
<213> ORGANISM: Artificial Sequence
<220> FEATURE:
<223> OTHER INFORMATION: Modified CDR

<400> SEQUENCE: 250

Ser Gln Asn Thr Gln Val Pro Arg Thr
1               5

<210> SEQ ID NO 251
<211> LENGTH: 19
<212> TYPE: PRT
<213> ORGANISM: Artificial Sequence
<220> FEATURE:
<223> OTHER INFORMATION: Modified CDR

<400> SEQUENCE: 251

Met Gly Asp Ile Asn Pro Val Asn Gly Asp Thr Lys Tyr Asn Pro Ser
1               5                   10                  15

Phe Gln Gly

<210> SEQ ID NO 252
<211> LENGTH: 7
<212> TYPE: PRT
<213> ORGANISM: Artificial Sequence
<220> FEATURE:
<223> OTHER INFORMATION: Modified CDR

<400> SEQUENCE: 252

Gly Gly Tyr Thr Thr Asp Tyr
1               5

<210> SEQ ID NO 253
<211> LENGTH: 9
<212> TYPE: PRT
<213> ORGANISM: Artificial Sequence
<220> FEATURE:
<223> OTHER INFORMATION: Modified CDR

<400> SEQUENCE: 253

Ser Gln Ser Thr His Val Pro Arg Thr
1               5

<210> SEQ ID NO 254
```

```
<211> LENGTH: 19
<212> TYPE: PRT
<213> ORGANISM: Artificial Sequence
<220> FEATURE:
<223> OTHER INFORMATION: Modified CDR

<400> SEQUENCE: 254

Met Gly Asp Ile Asn Pro Val Asn Gly Asp Thr Asn Phe Ser Pro Ser
1               5                   10                  15

Phe Gln Gly

<210> SEQ ID NO 255
<211> LENGTH: 7
<212> TYPE: PRT
<213> ORGANISM: Artificial Sequence
<220> FEATURE:
<223> OTHER INFORMATION: Modified CDR

<400> SEQUENCE: 255

Gly Gly Tyr Val Met Asp Tyr
1               5

<210> SEQ ID NO 256
<211> LENGTH: 9
<212> TYPE: PRT
<213> ORGANISM: Artificial Sequence
<220> FEATURE:
<223> OTHER INFORMATION: Modified CDR

<400> SEQUENCE: 256

Ser Gln Thr Thr His Ile Pro Arg Thr
1               5

<210> SEQ ID NO 257
<211> LENGTH: 19
<212> TYPE: PRT
<213> ORGANISM: Artificial Sequence
<220> FEATURE:
<223> OTHER INFORMATION: Modified CDR

<400> SEQUENCE: 257

Met Gly Asp Ile Asn Pro Val Asn Gly Asp Thr Asn Tyr Asn Pro Ser
1               5                   10                  15

Phe Gln Gly

<210> SEQ ID NO 258
<211> LENGTH: 9
<212> TYPE: PRT
<213> ORGANISM: Artificial Sequence
<220> FEATURE:
<223> OTHER INFORMATION: Modified CDR

<400> SEQUENCE: 258

Ser Gln Thr Thr His Val Pro Arg Thr
1               5

<210> SEQ ID NO 259
<211> LENGTH: 9
<212> TYPE: PRT
<213> ORGANISM: Artificial Sequence
<220> FEATURE:
<223> OTHER INFORMATION: Modified CDR

<400> SEQUENCE: 259

Ser Gln Thr Thr Gln Thr Pro Arg Thr
1               5
```

```
<210> SEQ ID NO 260
<211> LENGTH: 19
<212> TYPE: PRT
<213> ORGANISM: Artificial Sequence
<220> FEATURE:
<223> OTHER INFORMATION: Modified CDR

<400> SEQUENCE: 260

Met Gly Asp Ile Asn Pro Val Asn Gly Asp Thr Arg Phe Asn Pro Ser
1               5                   10                  15

Phe Gln Gly

<210> SEQ ID NO 261
<211> LENGTH: 9
<212> TYPE: PRT
<213> ORGANISM: Artificial Sequence
<220> FEATURE:
<223> OTHER INFORMATION: Modified CDR

<400> SEQUENCE: 261

Thr Gln Asn Thr His Thr Pro Arg Thr
1               5

<210> SEQ ID NO 262
<211> LENGTH: 19
<212> TYPE: PRT
<213> ORGANISM: Artificial Sequence
<220> FEATURE:
<223> OTHER INFORMATION: Modified CDR

<400> SEQUENCE: 262

Met Gly Asp Ile Asn Pro Val Asn Gly Asp Thr Arg Phe Ser Pro Ser
1               5                   10                  15

Phe Gln Gly

<210> SEQ ID NO 263
<211> LENGTH: 9
<212> TYPE: PRT
<213> ORGANISM: Artificial Sequence
<220> FEATURE:
<223> OTHER INFORMATION: Modified CDR

<400> SEQUENCE: 263

Val Gln Asn Thr Gln Val Pro Arg Thr
1               5

<210> SEQ ID NO 264
<211> LENGTH: 19
<212> TYPE: PRT
<213> ORGANISM: Artificial Sequence
<220> FEATURE:
<223> OTHER INFORMATION: Modified CDR

<400> SEQUENCE: 264

Met Gly Asp Ile Asn Pro Val Asn Gly Asp Thr Arg Tyr Asn Pro Ser
1               5                   10                  15

Phe Gln Gly

<210> SEQ ID NO 265
<211> LENGTH: 19
<212> TYPE: PRT
<213> ORGANISM: Artificial Sequence
<220> FEATURE:
<223> OTHER INFORMATION: Modified CDR
```

<400> SEQUENCE: 265

Met Gly Asp Ile Asn Pro Val Asn Gly Asp Thr Arg Tyr Ser Pro Ser
1               5                   10                  15

Phe Gln Gly

<210> SEQ ID NO 266
<211> LENGTH: 19
<212> TYPE: PRT
<213> ORGANISM: Artificial Sequence
<220> FEATURE:
<223> OTHER INFORMATION: Modified CDR

<400> SEQUENCE: 266

Met Gly Asp Ile Asn Pro Val Asn Ser Asp Thr Lys Tyr Asn Pro Ser
1               5                   10                  15

Phe Gln Gly

<210> SEQ ID NO 267
<211> LENGTH: 19
<212> TYPE: PRT
<213> ORGANISM: Artificial Sequence
<220> FEATURE:
<223> OTHER INFORMATION: Modified CDR

<400> SEQUENCE: 267

Met Gly Asp Ile Asn Pro Val Asn Ser Asp Thr Asn Phe Asn Pro Ser
1               5                   10                  15

Phe Gln Gly

<210> SEQ ID NO 268
<211> LENGTH: 19
<212> TYPE: PRT
<213> ORGANISM: Artificial Sequence
<220> FEATURE:
<223> OTHER INFORMATION: Modified CDR

<400> SEQUENCE: 268

Met Gly Asp Ile Asn Pro Val Asn Ser Asp Thr Asn Tyr Ser Pro Ser
1               5                   10                  15

Phe Gln Gly

<210> SEQ ID NO 269
<211> LENGTH: 19
<212> TYPE: PRT
<213> ORGANISM: Artificial Sequence
<220> FEATURE:
<223> OTHER INFORMATION: Modified CDR

<400> SEQUENCE: 269

Met Gly Asp Ile Asn Pro Val Asn Ser Asp Thr Arg Phe Asn Pro Ser
1               5                   10                  15

Phe Gln Gly

<210> SEQ ID NO 270
<211> LENGTH: 19
<212> TYPE: PRT
<213> ORGANISM: Artificial Sequence
<220> FEATURE:
<223> OTHER INFORMATION: Modified CDR

<400> SEQUENCE: 270

Met Gly Asp Ile Asn Pro Val Asn Ser Asp Thr Arg Phe Ser Pro Ser

```
1               5                   10                  15

Phe Gln Gly

<210> SEQ ID NO 271
<211> LENGTH: 19
<212> TYPE: PRT
<213> ORGANISM: Artificial Sequence
<220> FEATURE:
<223> OTHER INFORMATION: Modified CDR

<400> SEQUENCE: 271

Met Gly Asp Ile Asn Pro Val Asn Ser Asp Thr Arg Tyr Asn Pro Ser
1               5                   10                  15

Phe Gln Gly

<210> SEQ ID NO 272
<211> LENGTH: 19
<212> TYPE: PRT
<213> ORGANISM: Artificial Sequence
<220> FEATURE:
<223> OTHER INFORMATION: Modified CDR

<400> SEQUENCE: 272

Met Gly Asp Ile Asn Pro Val Asn Ser Asp Thr Arg Tyr Ser Pro Ser
1               5                   10                  15

Phe Gln Gly

<210> SEQ ID NO 273
<211> LENGTH: 19
<212> TYPE: PRT
<213> ORGANISM: Artificial Sequence
<220> FEATURE:
<223> OTHER INFORMATION: Modified CDR

<400> SEQUENCE: 273

Met Gly Asp Ile Tyr Pro Gly Asn Ser Asp Thr Lys Tyr Asn Pro Ser
1               5                   10                  15

Phe Gln Gly

<210> SEQ ID NO 274
<211> LENGTH: 19
<212> TYPE: PRT
<213> ORGANISM: Artificial Sequence
<220> FEATURE:
<223> OTHER INFORMATION: Modified CDR

<400> SEQUENCE: 274

Met Gly Asp Ile Tyr Pro Val Asn Gly Asp Thr Arg Tyr Asn Pro Ser
1               5                   10                  15

Phe Gln Gly

<210> SEQ ID NO 275
<211> LENGTH: 19
<212> TYPE: PRT
<213> ORGANISM: Artificial Sequence
<220> FEATURE:
<223> OTHER INFORMATION: Modified CDR

<400> SEQUENCE: 275

Met Gly Ile Ile Asn Pro Gly Asn Gly Asp Thr Arg Tyr Asn Pro Ser
1               5                   10                  15

Phe Gln Gly
```

```
<210> SEQ ID NO 276
<211> LENGTH: 19
<212> TYPE: PRT
<213> ORGANISM: Artificial Sequence
<220> FEATURE:
<223> OTHER INFORMATION: Modified CDR

<400> SEQUENCE: 276

Met Gly Ile Ile Asn Pro Val Asp Gly Asp Thr Lys Tyr Asn Pro Ser
1               5                   10                  15

Phe Gln Gly

<210> SEQ ID NO 277
<211> LENGTH: 19
<212> TYPE: PRT
<213> ORGANISM: Artificial Sequence
<220> FEATURE:
<223> OTHER INFORMATION: Modified CDR

<400> SEQUENCE: 277

Met Gly Ile Ile Asn Pro Val Asp Gly Asp Thr Asn Tyr Ser Pro Ser
1               5                   10                  15

Phe Gln Gly

<210> SEQ ID NO 278
<211> LENGTH: 19
<212> TYPE: PRT
<213> ORGANISM: Artificial Sequence
<220> FEATURE:
<223> OTHER INFORMATION: Modified CDR

<400> SEQUENCE: 278

Met Gly Ile Ile Asn Pro Val Asp Gly Asp Thr Arg Phe Asn Pro Ser
1               5                   10                  15

Phe Gln Gly

<210> SEQ ID NO 279
<211> LENGTH: 19
<212> TYPE: PRT
<213> ORGANISM: Artificial Sequence
<220> FEATURE:
<223> OTHER INFORMATION: Modified CDR

<400> SEQUENCE: 279

Met Gly Ile Ile Asn Pro Val Asp Gly Asp Thr Arg Phe Ser Pro Ser
1               5                   10                  15

Phe Gln Gly

<210> SEQ ID NO 280
<211> LENGTH: 19
<212> TYPE: PRT
<213> ORGANISM: Artificial Sequence
<220> FEATURE:
<223> OTHER INFORMATION: Modified CDR

<400> SEQUENCE: 280

Met Gly Ile Ile Asn Pro Val Asp Ser Asp Thr Asn Tyr Asn Pro Ser
1               5                   10                  15

Phe Gln Gly

<210> SEQ ID NO 281
<211> LENGTH: 19
<212> TYPE: PRT
```

<213> ORGANISM: Artificial Sequence
<220> FEATURE:
<223> OTHER INFORMATION: Modified CDR

<400> SEQUENCE: 281

Met Gly Ile Ile Asn Pro Val Asp Ser Asp Thr Arg Phe Asn Pro Ser
1               5                   10                  15

Phe Gln Gly

<210> SEQ ID NO 282
<211> LENGTH: 19
<212> TYPE: PRT
<213> ORGANISM: Artificial Sequence
<220> FEATURE:
<223> OTHER INFORMATION: Modified CDR

<400> SEQUENCE: 282

Met Gly Ile Ile Asn Pro Val Asp Ser Asp Thr Arg Tyr Asn Pro Ser
1               5                   10                  15

Phe Gln Gly

<210> SEQ ID NO 283
<211> LENGTH: 19
<212> TYPE: PRT
<213> ORGANISM: Artificial Sequence
<220> FEATURE:
<223> OTHER INFORMATION: Modified CDR

<400> SEQUENCE: 283

Met Gly Ile Ile Asn Pro Val Asp Ser Asp Thr Arg Tyr Ser Pro Ser
1               5                   10                  15

Phe Gln Gly

<210> SEQ ID NO 284
<211> LENGTH: 19
<212> TYPE: PRT
<213> ORGANISM: Artificial Sequence
<220> FEATURE:
<223> OTHER INFORMATION: Modified CDR

<400> SEQUENCE: 284

Met Gly Ile Ile Asn Pro Val Asn Gly Asp Thr Lys Phe Asn Pro Ser
1               5                   10                  15

Phe Gln Gly

<210> SEQ ID NO 285
<211> LENGTH: 19
<212> TYPE: PRT
<213> ORGANISM: Artificial Sequence
<220> FEATURE:
<223> OTHER INFORMATION: Modified CDR

<400> SEQUENCE: 285

Met Gly Ile Ile Asn Pro Val Asn Gly Asp Thr Lys Tyr Asn Pro Ser
1               5                   10                  15

Phe Gln Gly

<210> SEQ ID NO 286
<211> LENGTH: 19
<212> TYPE: PRT
<213> ORGANISM: Artificial Sequence
<220> FEATURE:
<223> OTHER INFORMATION: Modified CDR

```
<400> SEQUENCE: 286

Met Gly Ile Ile Asn Pro Val Asn Gly Asp Thr Lys Tyr Ser Pro Ser
1               5                   10                  15

Phe Gln Gly

<210> SEQ ID NO 287
<211> LENGTH: 19
<212> TYPE: PRT
<213> ORGANISM: Artificial Sequence
<220> FEATURE:
<223> OTHER INFORMATION: Modified CDR

<400> SEQUENCE: 287

Met Gly Ile Ile Asn Pro Val Asn Gly Asp Thr Asn Phe Asn Pro Ser
1               5                   10                  15

Phe Gln Gly

<210> SEQ ID NO 288
<211> LENGTH: 19
<212> TYPE: PRT
<213> ORGANISM: Artificial Sequence
<220> FEATURE:
<223> OTHER INFORMATION: Modified CDR

<400> SEQUENCE: 288

Met Gly Ile Ile Asn Pro Val Asn Gly Asp Thr Asn Phe Ser Pro Ser
1               5                   10                  15

Phe Gln Gly

<210> SEQ ID NO 289
<211> LENGTH: 19
<212> TYPE: PRT
<213> ORGANISM: Artificial Sequence
<220> FEATURE:
<223> OTHER INFORMATION: Modified CDR

<400> SEQUENCE: 289

Met Gly Ile Ile Asn Pro Val Asn Gly Asp Thr Asn Tyr Ser Pro Ser
1               5                   10                  15

Phe Gln Gly

<210> SEQ ID NO 290
<211> LENGTH: 19
<212> TYPE: PRT
<213> ORGANISM: Artificial Sequence
<220> FEATURE:
<223> OTHER INFORMATION: Modified CDR

<400> SEQUENCE: 290

Met Gly Ile Ile Asn Pro Val Asn Gly Asp Thr Arg Phe Asn Pro Ser
1               5                   10                  15

Phe Gln Gly

<210> SEQ ID NO 291
<211> LENGTH: 19
<212> TYPE: PRT
<213> ORGANISM: Artificial Sequence
<220> FEATURE:
<223> OTHER INFORMATION: Modified CDR

<400> SEQUENCE: 291

Met Gly Ile Ile Asn Pro Val Asn Gly Asp Thr Arg Phe Ser Pro Ser
1               5                   10                  15
```

<210> SEQ ID NO 292
<211> LENGTH: 19
<212> TYPE: PRT
<213> ORGANISM: Artificial Sequence
<220> FEATURE:
<223> OTHER INFORMATION: Modified CDR

<400> SEQUENCE: 292

Met Gly Ile Ile Asn Pro Val Asn Gly Asp Thr Arg Tyr Asn Pro Ser
1               5                   10                  15

Phe Gln Gly

<210> SEQ ID NO 293
<211> LENGTH: 19
<212> TYPE: PRT
<213> ORGANISM: Artificial Sequence
<220> FEATURE:
<223> OTHER INFORMATION: Modified CDR

<400> SEQUENCE: 293

Met Gly Ile Ile Asn Pro Val Asn Gly Asp Thr Arg Tyr Ser Pro Ser
1               5                   10                  15

Phe Gln Gly

<210> SEQ ID NO 294
<211> LENGTH: 19
<212> TYPE: PRT
<213> ORGANISM: Artificial Sequence
<220> FEATURE:
<223> OTHER INFORMATION: Modified CDR

<400> SEQUENCE: 294

Met Gly Ile Ile Asn Pro Val Asn Ser Asp Thr Lys Tyr Asn Pro Ser
1               5                   10                  15

Phe Gln Gly

<210> SEQ ID NO 295
<211> LENGTH: 19
<212> TYPE: PRT
<213> ORGANISM: Artificial Sequence
<220> FEATURE:
<223> OTHER INFORMATION: Modified CDR

<400> SEQUENCE: 295

Met Gly Ile Ile Asn Pro Val Asn Ser Asp Thr Asn Phe Asn Pro Ser
1               5                   10                  15

Phe Gln Gly

<210> SEQ ID NO 296
<211> LENGTH: 19
<212> TYPE: PRT
<213> ORGANISM: Artificial Sequence
<220> FEATURE:
<223> OTHER INFORMATION: Modified CDR

<400> SEQUENCE: 296

Met Gly Ile Ile Asn Pro Val Asn Ser Asp Thr Asn Tyr Ser Pro Ser
1               5                   10                  15

Phe Gln Gly

```
<210> SEQ ID NO 297
<211> LENGTH: 19
<212> TYPE: PRT
<213> ORGANISM: Artificial Sequence
<220> FEATURE:
<223> OTHER INFORMATION: Modified CDR

<400> SEQUENCE: 297

Met Gly Ile Ile Asn Pro Val Asn Ser Asp Thr Arg Phe Ser Pro Ser
1               5                   10                  15

Phe Gln Gly

<210> SEQ ID NO 298
<211> LENGTH: 19
<212> TYPE: PRT
<213> ORGANISM: Artificial Sequence
<220> FEATURE:
<223> OTHER INFORMATION: Modified CDR

<400> SEQUENCE: 298

Met Gly Ile Ile Asn Pro Val Asn Ser Asp Thr Arg Tyr Asn Pro Ser
1               5                   10                  15

Phe Gln Gly

<210> SEQ ID NO 299
<211> LENGTH: 19
<212> TYPE: PRT
<213> ORGANISM: Artificial Sequence
<220> FEATURE:
<223> OTHER INFORMATION: Modified CDR

<400> SEQUENCE: 299

Met Gly Ile Ile Asn Pro Val Asn Ser Asp Thr Arg Tyr Ser Pro Ser
1               5                   10                  15

Phe Gln Gly

<210> SEQ ID NO 300
<211> LENGTH: 19
<212> TYPE: PRT
<213> ORGANISM: Artificial Sequence
<220> FEATURE:
<223> OTHER INFORMATION: Modified CDR

<400> SEQUENCE: 300

Met Gly Asn Ile Asn Pro Val Asp Gly Asp Thr Arg Tyr Asn Pro Ser
1               5                   10                  15

Phe Gln Gly

<210> SEQ ID NO 301
<211> LENGTH: 19
<212> TYPE: PRT
<213> ORGANISM: Artificial Sequence
<220> FEATURE:
<223> OTHER INFORMATION: Modified CDR

<400> SEQUENCE: 301

Met Gly Val Ile Asn Pro Val Asn Ser Asp Thr Asn Tyr Asn Pro Ser
1               5                   10                  15

Phe Gln Gly

<210> SEQ ID NO 302
<211> LENGTH: 19
<212> TYPE: PRT
<213> ORGANISM: Mus musculus
```

```
<400> SEQUENCE: 302

Ile Gly Asp Ile Asn Pro Val Asn Gly Asp Thr Asn Phe Asn Glu Ser
1               5                   10                  15

Phe Gln Gly
```

ANTI-CD47 ANTIBODY MOLECULES

This application is a continuation of International Patent Application No. PCT/GB2018/052347, filed on Aug. 17, 2018, which claims the benefit of GB Patent Application No. 1808570.4, filed on May 24, 2018, GB Patent Application No. 1802595.7, filed on Feb. 16, 2018 and GB Patent Application No. 1713298.6, filed on Aug. 18, 2017, the disclosure of each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: UH4L_001_01US SeqListST25.txt, date recorded: Aug. 19, 2019, file size 80,808 bytes).

FIELD OF THE INVENTION

The invention relates to antibody molecules binding specifically to CD47 (Cluster of Differentiation 47, also known as integrin associated protein [IAP]) and medical uses thereof.

BACKGROUND OF THE INVENTION

CD47 (also known as integrin associated protein [IAP]) is a transmembrane protein that belongs to the immunoglobulin superfamily and binds to several known partners, including: membrane integrins, thrombospondin-1 (TSP-1) and signal-regulatory protein alpha (SIRPα). CD47 is associated with a range of cellular processes, including apoptosis, proliferation, adhesion, and migration of cells and, importantly, it plays a key role in immune and angiogenic responses. CD47-SIRPα signalling is a critical molecular interaction that inhibits the activation of phagocytosis by macrophages and other myeloid cells. This promotes the survival of tumour cells and therefore acts as a myeloid lineage-specific immune checkpoint.

Preclinical evidence suggests that blocking CD47-SIRPα signalling can enhance the phagocytic activity of macrophages and inhibit the growth of xenografts in numerous experimental models of both haematological and solid malignancies. As macrophage activity is also a recognised factor in the biology of inflammation-associated tissue remodelling such as tissue fibrosis and the formation of atherosclerotic plaques, the CD47-SIRPα signalling axis is also of considerable therapeutic potential in non-cancerous diseases. Hence, anti-CD47 mAbs have the potential to act as immunotherapeutic agents in cancer and other settings, and to amplify the effectiveness of currently established therapies.

The majority of currently approved antibody therapeutics are derived from immunized rodents. Many of those antibodies have undergone a process known as "humanization", via the "grafting" of murine CDRs into human v-gene framework sequences (see Nelson et al., 2010, Nat Rev Drug Discov 9: 767-774). This process is often inaccurate and leads to a reduction in target binding affinity of the resulting antibody. To return the binding affinity of the original antibody, murine residues are usually introduced at key positions in the variable domain frameworks of the grafted v-domains (also known as "back-mutations").

While antibodies humanized via CDR grafting and back mutations have been shown to induce lower immune response rates in the clinic in comparison to those with fully murine v-domains, antibodies humanized using this basic grafting method still carry significant clinical development risks due to the potential physical instability and immunogenicity motifs still housed in the grafted CDR loops. Antibodies such as CD47 inhibitors that target receptors on immune cells, and whose pharmacological function is to stimulate immune responses via antigen presentation, are at heightened risk of provoking anti-drug antibody responses. These anti-drug antibody responses in the patient can reduce drug half-life, potency and safety during clinical use. As animal testing of protein immunogenicity is often non-predictive of immune responses in man, antibody engineering for therapeutic use focuses on minimizing predicted human T-cell epitope content, non-human germline amino acid content and aggregation potential in the purified protein.

The ideal humanized antagonistic anti-CD47 antibody would therefore have as many identical residues as possible in the v-domains to those found in both the frameworks and CDRs of well-characterized human germline sequences. Townsend et al. (2015; PNAS 112: 15354-15359) describe a method for generating antibodies in which CDRs derived from rat, rabbit and mouse antibodies were grafted into preferred human frameworks and then subject to a human germ-lining approach termed "Augmented Binary Substitution". Although the approach demonstrated a fundamental plasticity in the original antibody paratopes, in the absence of highly accurate antibody-antigen co-crystal structural data, it is still not possible to reliably predict which individual residues in the CDR loops of any given antibody can be converted to human germline, and in what combination. CDR germ-lining is thus a complex, multifactorial problem, as multiple functional properties of the molecule should preferably be maintained, including in this instance: target binding specificity, affinity to CD47 from both human and animal test species (e.g. cynomolgus monkey, also known as the crab-eating macaque, i.e. *Macaca fascicularis*), v-domain biophysical stability and/or IgG expression yield. Antibody engineering studies have shown that mutation of even single residue positions in key CDRs can have dramatic effects on all of these desired molecular properties.

WO2014/093678A2 describes an antagonistic murine anti-CD47 IgG molecule termed "VxP037", and also the preparation of humanized forms of VxP037. Those humanized forms of VxP037 were produced using classical humanization techniques, i.e. by grafting of Kabat-defined murine CDRs into human heavy and light chain framework sequences, with some of the human framework residues being potentially back-mutated to the correspondingly positioned VxP037 murine residues. For reasons noted above, such humanized forms of VxP037 described in WO2014/093678A2 are not ideal.

The present invention provides a number of optimized anti-CD47 antibodies and medical uses thereof.

SUMMARY OF THE INVENTION

According to one aspect of the invention, there is provided an antibody molecule which specifically binds to human CD47, and optionally also to cynomolgus monkey CD47 and/or to mouse CD47, or an antigen-binding portion thereof, wherein the antibody molecule or antigen-binding portion comprises a heavy chain variable region with:

an HCDR1 having amino acids in sequence in the following order: G-Y-T or any amino acid (for example, S, N or R)-F-T or a conservative substitution of T-N or a conservative substitution of N-Y-Y-I or a conservative substitution of I-F or any amino acid (for example, V or G) (SEQ ID NO: 1);

an HCDR2 having amino acids in sequence in the following order: M or a conservative substitution of M-G-I or any amino acid (for example, N, V or D)-I-N or any amino acid (for example, Y)-P-V or any amino acid (for example, G or F)-D or a conservative substitution of D-G or a conservative substitution of G-D-T-N or a conservative substitution of N (for example, R)-Y or a conservative substitution of Y-N or a conservative substitution of N (for example, S)-P-S-F-Q-G (SEQ ID NO: 2); and an HCDR3 having amino acids in sequence in the following order: G-G-Y or any amino acid (for example, H, I, Q or F)-T or any amino acid (for example, V or I)-M or any amino acid (for example, T, R, P, A or L)-D or any amino acid (for example, G)-R or any amino acid (for example, Q, N, Y, S, W, K, A, E, F, H, I, L, M, T or V) (SEQ ID NO: 3).

In aspects of the invention, the HCDR1 of the antibody molecule or antigen-binding portion may exclude the sequence GYTFTNYYVF (SEQ ID NO: 4) (VxP037 murine/humanized antibody HCDR1 disclosed in WO2014/093678A2) and/or the HCDR3 of the antibody molecule or antigen-binding portion may exclude the sequence GGYTMDY (SEQ ID NO: 5) (VxP037 murine/humanized antibody HCDR3 disclosed in WO2014/093678A2).

The antibody molecule or antigen-binding portion may further comprise a light chain variable region with:

an LCDR1 having amino acids in sequence in the following order: R-S-S-Q or a conservative substitution of Q-S-L or a conservative substitution of L-L or a conservative substitution of L-H-S-N or any amino acid (for example, Q, S, T, A or G) or a conservative substitution of N (for example, Q, S, T or G)-G or a conservative substitution of G (for example, A)-Y or any amino acid (for example, N or S)-T or a conservative substitution of T (for example, N)-Y-L-H or any amino acid (for example, D) (SEQ ID NO: 6);

an LCDR2 having amino acids in sequence in the following order: K or any amino acid (for example, L or M)-V or any amino acid (for example, G)-S-N or any amino acid (for example, Y)-R-L or any amino acid (for example, F, A or S)-S (SEQ ID NO: 7); and an LCDR3 having amino acids in sequence in the following order: F or any amino acid (for example, L, M, S, T or V)-Q-Q or any amino acid (for example, N, A, T or S)-T or any amino acid (for example, L, M or I)-H or a conservative substitution of H-T or any amino acid (for example, V, I, A or F)-P or any amino acid (for example, L)-R or any amino acid (for example, W)-T (SEQ ID NO: 8).

In aspects of the invention, the LCDR1 of the antibody molecule or antigen-binding portion may exclude the sequence RSSQSLVHSNGNTYLH (SEQ ID NO: 9) (VxP037 murine/humanized antibody LCDR1 disclosed in WO2014/093678A2), and/or the LCDR2 of the antibody molecule or antigen-binding portion may exclude the sequence KVSYRFS (SEQ ID NO: 10) (VxP037 murine/humanized antibody LCDR2 disclosed in WO2014/093678A2) and/or the LCDR3 of the antibody molecule or antigen-binding portion may exclude the sequence SQNTHVPRT (SEQ ID NO: 11) (VxP037 murine/humanized antibody LCDR3 disclosed in WO2014/093678A2).

The CDR sequences above are defined using the "Unified" definition, as set out in Table 1 and described below. As an alternative, the CDR sequences in the present invention may be defined using the shorter "AHo" definition (see Table 1), which is based on structural biology and aims to unify nomenclature for all immunoglobulin v-domains.

Using the shorter "AHo" CDR definition, the invention in one aspect provides an antibody molecule which specifically binds to human CD47, and optionally also to cynomolgus monkey CD47 and/or to mouse CD47, or an antigen-binding portion thereof, wherein the antibody molecule or antigen-binding portion comprises a heavy chain variable region with:

an HCDR1 having amino acids in sequence in the following order: G-S-G-Y-T or any amino acid (for example, S, N or R)-F-T or a conservative substitution of T-N or a conservative substitution of N-Y-Y (SEQ ID NO: 12);

an HCDR2 having amino acids in sequence in the following order: I-N or any amino acid (for example, Y)-P-V or any amino acid (for example, G or F)-D or a conservative substitution of D-G or a conservative substitution of G-D-T-N or a conservative substitution of N (for example, R)-Y or a conservative substitution of Y-N or a conservative substitution of N (for example, S)-P-S-F-Q-G (SEQ ID NO: 13); and an HCDR3 having amino acids in sequence in the following order: G-G-Y or any amino acid (for example, H, I, Q or F)-T or any amino acid (for example, V or I)-M or any amino acid (for example, T, R, P, A or L)-D or any amino acid (for example, G) (SEQ ID NO: 14).

Using the AHo definition, the HCDR1 of the antibody molecule or antigen-binding portion may exclude the sequence GSGYTFTNYY (SEQ ID NO: 15) (VxP037 murine/humanized antibody HCDR1 disclosed in WO2014/093678A2) and/or the HCDR3 of the antibody molecule or antigen-binding portion may exclude the sequence GGYTMD (SEQ ID NO: 16) (VxP037 murine/humanized antibody HCDR3 disclosed in WO2014/093678A2).

The antibody molecule or antigen-binding portion may further comprise a light chain variable region with CDRs defined using the AHo definition as follows:

an LCDR1 having amino acids in sequence in the following order: S-S-Q or a conservative substitution of Q-S-L or a conservative substitution of L-L or a conservative substitution of L-H-S-N or any amino acid (for example, Q, S, T, A or G) or a conservative substitution of N (for example, Q, S, T or G)-G or a conservative substitution of G (for example, A)-Y or any amino acid (for example, N or S)-T or a conservative substitution of T (for example, N)-Y (SEQ ID NO: 17);

an LCDR2 having amino acids in sequence in the following order: K or any amino acid (for example, L or M)-V or any amino acid (for example, G)-S-N or any amino acid (for example, Y)-R-L or any amino acid (for example, F, A or S)-S (SEQ ID NO: 7); and an LCDR3 having amino acids in sequence in the following order: Q or any amino acid (for example, N, A, T or S)-T or any amino acid (for example, L, M or I)-H or a conservative substitution of H-T or any amino acid (for example, V, I, A or F)-P or any amino acid (for example, L)-R or any amino acid (for example, W) (SEQ ID NO: 18).

Using the AHo definition, in aspects of the invention the LCDR1 of the antibody molecule or antigen-binding portion may exclude the sequence SSQSLVHSNGNTY (SEQ ID NO: 19) (VxP037 murine/humanized antibody LCDR1 disclosed in WO2014/093678A2), and/or the LCDR2 of the antibody molecule or antigen-binding portion may exclude the sequence KVSYRFS (SEQ ID NO: 10) (VxP037 murine/humanized antibody LCDR2 disclosed in WO2014/

093678A2) and/or the LCDR3 of the antibody molecule or antigen-binding portion may exclude the sequence NTHVPR (SEQ ID NO: 20) (VxP037 murine/humanized antibody LCDR3 disclosed in WO2014/093678A2).

Also provided according to the invention is an immunoconjugate comprising the antibody molecule or antigen-binding portion thereof as defined herein linked a therapeutic agent.

In another aspect the invention provides nucleic acid molecule encoding the antibody molecule or antigen-binding portion thereof as defined herein.

Further provided is a vector comprising the nucleic acid molecule of the invention.

Also provided is a host cell comprising the nucleic acid molecule or the vector of the invention as defined herein.

In a further aspect there is provided a method of producing an anti-CD47 antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the immunoconjugate of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an ischemia-reperfusion injury, an autoimmune disease or an inflammatory disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The autoimmune disease or inflammatory disease may be selected in all aspects from the group consisting of: arthritis, multiple sclerosis, psoriasis, Crohn's disease, inflammatory bowel disease, lupus, Grave's disease and Hashimoto's thyroiditis, and ankylosing spondylitis.

The ischemia-reperfusion injury in all aspect may occur in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting or trauma.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an ischemia-reperfusion injury, an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an ischemia-reperfusion injury, an autoimmune disease or an inflammatory disease.

The invention also provides a method for treating or preventing a cardiovascular disease or a fibrotic disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an ischemia-reperfusion injury, an autoimmune disease, an inflammatory disease or a fibrotic disease.

The cardiovascular disease in any aspect of the invention may for example be coronary heart disease or atherosclerosis.

The fibrotic disease in any aspect of the invention may be selected from the group consisting of myocardial infarction, angina, osteoarthritis, pulmonary fibrosis, cystic fibrosis, bronchitis and asthma.

The invention also provides a method of producing an antibody molecule which specifically binds to human CD47 and optionally also to cynomolgus monkey CD47 and/or to mouse CD47, or an antigen-binding portion thereof, comprising the steps of:

(1) grafting anti-CD47 CDRs from a non-human source into a human v-domain framework to produce a humanized anti-CD47 antibody molecule or antigen-binding portion thereof;

(2) generating a phage library of clones of the humanized anti-CD47 antibody molecule or antigen-binding portion thereof comprising one or more mutations in the CDRs;

(3) screening the phage library for binding to human CD47 and optionally also to cynomolgus monkey CD47 and/or to mouse CD47;

(4) selecting clones from the screening step (3) having binding specificity to human CD47 and optionally also to cynomolgus monkey CD47 and/or to mouse CD47; and (5) producing an antibody molecule which specifically binds to human CD47 and optionally also to cynomolgus monkey CD47 and/or to mouse CD47, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

The method may comprise a further step of assessing immunogenicity of one or more v-domains in the clones selected in step (4) or the antibody molecule produced in step (5), and optionally generating one or more further mutations, for example in a CDR and framework region, to reduce immunogenicity. Immunogenicity may be assessed by identifying the location of T cell epitopes, for example using in silico technologies as described herein.

BRIEF DESCRIPTION OF THE FIGURES

FIG. 1A-FIG. 1C. Direct binding ELISA of library-derived anti-CD47 scFvs against human and mouse CD47-Fc proteins. Clones were derived from 3 separate phage selection branches (FIG. 1A shows Branch A periprep ELISA; FIG. 1B shows Branch B periprep ELISA; and FIG. 1C shows Branch C periprep ELISA) where phage populations were selected on biotinylated human, mouse and/or cynomolgus monkey CD47-Fc proteins in each round. After each round of selection, library-derived clones (black circles) were screened against both human and mouse CD47-Fc. Mean±SD values in each round are represented in grey bars. In each graph, the X-axis shows selection round ("R"), with "H" denoting human and "M" denoting mouse, and the Y-axis shows binding signal (OD 450 nm).

In FIG. 2A, the sequences on the x-axis in order from left to right are SEQ ID NO: 4, SEQ ID NO: 302 and SEQ ID NO: 5. In FIG. 2B, the sequences on the x-axis in order from left to right are SEQ ID NO: 9, SEQ ID NO: 10 and SEQ ID NO: 11.

FIG. 3A-FIG. 3H. Direct titration ELISA for IgG binding to human, mouse and cyno CD47-Fc proteins. Chimeric anti-CD47 (mVH/mVL), library-derived clones in human IgG1null format were titrated (in µg/ml) in a direct binding ELISA against human, mouse and cyno CD47-Fc proteins (FIG. 3A-FIG. 3H). The mVH/mVL, library-derived clones and designer clone MH demonstrated binding activity against all 3 orthologs of CD47. Clone VH-A1/VL-B1 binds human and cyno CD47 but does not bind to mouse. Clone TTP lost almost all binding function. In each graph, the X-axis shows IgG concentration in µg/ml and the Y-axis shows binding signal (OD 450 nm).

FIG. 4A-FIG. 4C. ELISA-based CD47-Fc-SIRPa competition assay. ELISA binding signal for human (FIG. 4A), cyno (FIG. 4B) and mouse (FIG. 4C) CD47-Fc proteins to plate-bound human SIRPα was examined in the presence of titrated competitor library-derived leads: A-D5, G-B6, D-H3 and VH-A1/VL-B1 in IgG1null format, Isotype IgG1 as a negative control, plus mVH/mVL in IgG1null format as a positive control. All library-derived IgGs and mVH/mVL demonstrated concentration-dependent reduction in binding of the human, murine and cyno CD47-Fc proteins, suggesting maintenance of a shared epitope. Notably, clone A-D5 exhibited significantly increased potency in neutralisation of mouse CD47 in comparison to the mVH/mVL and VH-A1/VL-B1 did not show the capacity to neutralise the activity of murine CD47. Neither designer clone MH nor TTP exhibited any neutralisation signal and are not plotted here, for clarity. In each graph, the X-axis shows antibody concentration in nM and the Y-axis shows binding signal (OD 450 nm). In the figure legends, "IC" refers to isotype control.

FIG. 5A-FIG. 5G. Binding specificity analyses for prioritized lead clones. Off-target homologue binding risk for mVH/mVL in IgG1 (FIG. 5A) and IgG1null (FIG. 5B) format and library-derived leads A-D5 (FIG. 5C), VH-A1/VL-B1 (FIG. 5D), F-E7 (FIG. 5E), D-H3 (FIG. 5F), and G-B6 (FIG. 5G) in IgG1null format was examined by direct ELISA on CD47-Fc orthologs and a panel of 14 human immunoglobulin superfamily proteins as labelled on each X-axis ("B" refers to blank). Binding to human, cyno and murine CD47-Fcs (h/c/mCD47-Fc) was performed at an IgG concentration of 1 µg/ml. Binding to all other proteins was performed at an IgG concentration of 10 µg/ml. In each plot, the Y-axis shows binding signal (OD 450 nm). For almost all IgGs, binding was observed to hCD47-Fc, mCD37-Fc and cCD47-Fc alone. No binding above background was observed for any other human protein. Notably, clone VH-A1/VL-B1 again did not show reactivity to murine CD47.

FIG. 6A-FIG. 6C. Flow cytometric binding to human and cyno CD47+ CHO-K1 cells. Commercial anti-CD47 antibody MS1991, human IgG1 ("I IgG1") and IgG4 ("I IgG4") Isotype controls, lead library-derived IgGs in both IgG1null ("IgG1N") and IgG4(S228P) formats were examined for specific binding on cyno-transfected CHO-K1 cells (FIG. 6A), human-transfected CHO-K1 cells (FIG. 6B), and wild type (wt, i.e. untransfected) CHO-K1 cells (FIG. 6C). IgGs were tested at concentrations ranging from 24-100,000 ng/ml. Concentration-dependent binding was observed against both human and cyno cell lines for all CD47-specific antibodies but not Isotype controls. Low-level binding signals above background were observed against wild type CHO-K1 cells for most antibodies, with significantly stronger signal for the mVH/mVL-derived IgGs and particularly low signal for VH-A1/VL-B1 IgGs. In each graph, the X-axis shows each IgG tested and its concentration in ng/ml, and the Y-axis shows mean fluorescence intensity (MFI).

FIG. 8A-FIG. 8C. Development risk ELISAs. This assay showed that the A-D5, G-B6, D-H3, VH-A1/VL-B1 and mVH/mVL antibodies in IgG1null form exhibit little or no binding to the negatively charged biomolecules Insulin (FIG. 8A), double-stranded DNA (dsDNA) (FIG. 8B) and single-stranded DNA (ssDNA) (FIG. 8C). In each graph, the X-axis shows IgG concentration in µg/ml and the Y-axis shows binding signal (OD 450 nm). Strong off-target binding to these molecules, as observed for Bococizumab and Briakinumab analogues has been shown to be a high-risk indicator of poor clinical performance of therapeutic antibodies.

FIG. 9A-FIG. 9C. Direct titration ELISA for designer IgGs binding to human, mouse and cyno CD47-Fc proteins. Chimeric anti-CD47 (mVH/mVL), designer A-D5-derived clones in human IgG1null format were titrated (in µg/ml) in a direct binding ELISA against human (FIG. 9A), cyno (FIG. 9B) and mouse (FIG. 9C) CD47-Fc proteins. In each graph, the X-axis shows IgG concentration in µg/ml and the Y-axis shows binding signal (OD 450 nm). Most clones demonstrated binding activity against all 3 orthologs of CD47, although clone A-D5.7 only shows weak binding to cyno CD47 and clone A-D5.10 lost almost all binding function to mouse CD47. In the figure legend, "IgG1NI" refers to IgG1 null isotype.

FIG. 10A-FIG. 10C. ELISA-based CD47-Fc-SIRPa competition assay for designer IgGs. ELISA binding signal for human (FIG. 10A), cyno (FIG. 10B) and mouse (FIG. 10C) CD47-Fc proteins to plate-bound human SIRPα was examined in the presence of titrated competitor designer IgGs in IgG1null format, plus Isotype IgG1 as a negative control (represented by "IgG1NI") and mVH/mVL in IgG1null format as a positive control. In each graph, the X-axis shows IgG concentration in nM and the Y-axis shows binding signal (OD 450 nm). Notably, several A-D5-derived clones again exhibited significantly increased potency in neutralisation of mouse CD47 in comparison to the mVH/mVL. Neither designer clone A-D5.7 nor A-D5.10 exhibited any neutralisation signal on the orthologs for which they showed weak ELISA binding signal and are not plotted here, for clarity.

FIG. 11A-FIG. 11C. Direct titration ELISA for A-D5.4-derived designer IgGs binding to human, mouse and cyno CD47-Fc proteins. Chimeric anti-CD47 (mVH/mVL), designer A-D5.4-derived clones in human IgG1null format were titrated (in µg/ml) in a direct binding ELISA against human (FIG. 11A), cyno (FIG. 11B) and mouse (FIG. 11C) CD47-Fc proteins. In each graph, the X-axis shows IgG concentration in µg/ml and the Y-axis shows binding signal (OD 450 nm). All clones demonstrated binding activity against all 3 orthologs of CD47. In the figure legends, "IgG1NI" refers to IgG1 null isotype.

FIG. 12A-FIG. 12C. ELISA-based CD47-Fc-SIRPα competition assay for designer IgGs. ELISA binding signal for human (FIG. 12A), cyno (FIG. 12B) and mouse (FIG. 12C) CD47-Fc proteins to plate-bound human SIRPα was examined in the presence of titrated competitor designer IgGs in IgG1null format, plus Isotype IgG1 as a negative control (represented by "IgG1NI") and mVH/mVL in IgG1null format as a positive control. In each graph, the X-axis shown IgG concentration in nM and the Y-axis shows binding signal (OD 450 nm). Notably, several A-D5.4-derived clones again exhibited significantly increased potency in neutralisation of mouse CD47 in comparison to the mVH/mVL.

FIG. 15. Flow cytometric binding of library-derived and designer IgGs to CHO-K1 cells. Commercial anti-CD47 antibody MS1991, human IgG1 and IgG4 Isotype controls (represented by "I IgG1" and "I IgG4" respectively), and lead IgGs A-D5, A-D5.4 and A-D5.16 in both IgG1null and IgG4 formats were examined for specific binding on wild type (i.e. untransfected) CHO-K1 cells. IgGs were tested at concentrations ranging from 24-25,000 ng/ml. Concentration-dependent binding was observed for the parental mVH/mVL antibody in both IgG1null and IgG4 formats, but only weak or no binding was observed for Isotype controls, MS1991 and IgGs A-D5, A-D5.4 and A-D5.16 in both IgG formats. In each graph, the X-axis shows concentration of IgG in ng/ml, and the Y-axis shows MFI.

FIG. 16. Flow cytometric testing of binding to human HL60 cells. Commercial anti-CD47 antibody MS1991, human IgG1 and IgG4 Isotype controls (represented by "I IgG1" and "I IgG4", respectively), lead IgGs in both IgG1null and IgG4(S228P) formats were examined for specific binding on HL60 cells. IgGs were tested at concentrations ranging from 24-100000 ng/ml. Concentration-dependent binding was observed for all clones other than the Isotype controls. In each graph, the X-axis shows concentration of IgG in ng/ml, and the Y-axis shows MFI.

FIG. 18A-FIG. 18C. Direct titration ELISA for A-D5.16 and A-D5.16-DI designer IgGs binding to human, mouse and cyno CD47-Fc proteins. Chimeric anti-CD47 (mVH/mVL), designer A-D5.16 and A-D5.16-DI clones in human IgG1null format were titrated (in µg/ml) in a direct binding ELISA against human (FIG. 18A), cyno (FIG. 18B) and mouse (FIG. 18C) CD47-Fc proteins. All clones demonstrated binding activity against all 3 orthologs of CD47. In each graph, the X-axis shows concentration of IgG in µg/ml, and the Y-axis shows binding signal (OD 450 nm).

FIG. 19A-FIG. 19C. ELISA-based CD47-Fc-SIRPα competition assay for designer IgGs. ELISA binding signal for human (FIG. 19A), cyno (FIG. 19B) and mouse (FIG. 19C) CD47-Fc proteins to plate-bound human SIRPα was examined in the presence of titrated competitor designer IgGs in IgG1null format, plus Isotype IgG1 as a negative control and mVH/mVL in IgG1null format as a positive control. In each graph, the X-axis shows antibody concentration in nM, and the Y-axis shows binding signal (OD 450 nm).

(FIG. 20A) Flow cytometric analysis of the phagocytosis of CSFE-labelled HL60 cells by human CD14+ macrophages was performed at multiple concentrations (as shown on the X-axis) for clones A-D5, A-D5.4. A-D5.16 and mVH/mVL in IgG4 (S228P) format and additionally A-D5 in IgG1null format (represented by "IgG1 A-D5N"). The X-axis shows antibody concentration (µg/ml), and the Y-axis shows % cells that are CFSE$^+$ and CD14$^+$. (FIG. 20B) The analysis was then repeated across multiple human macrophage donors for A-D5 and mVH/mVL in IgG4 format, at a standard concentration of 10 µg/ml. The X-axis shows donor number, and the Y-axis shows % cells that are CFSE$^+$ and CD14$^+$. "V" denotes vehicle.

DETAILED DESCRIPTION OF THE INVENTION

Figure 2A:
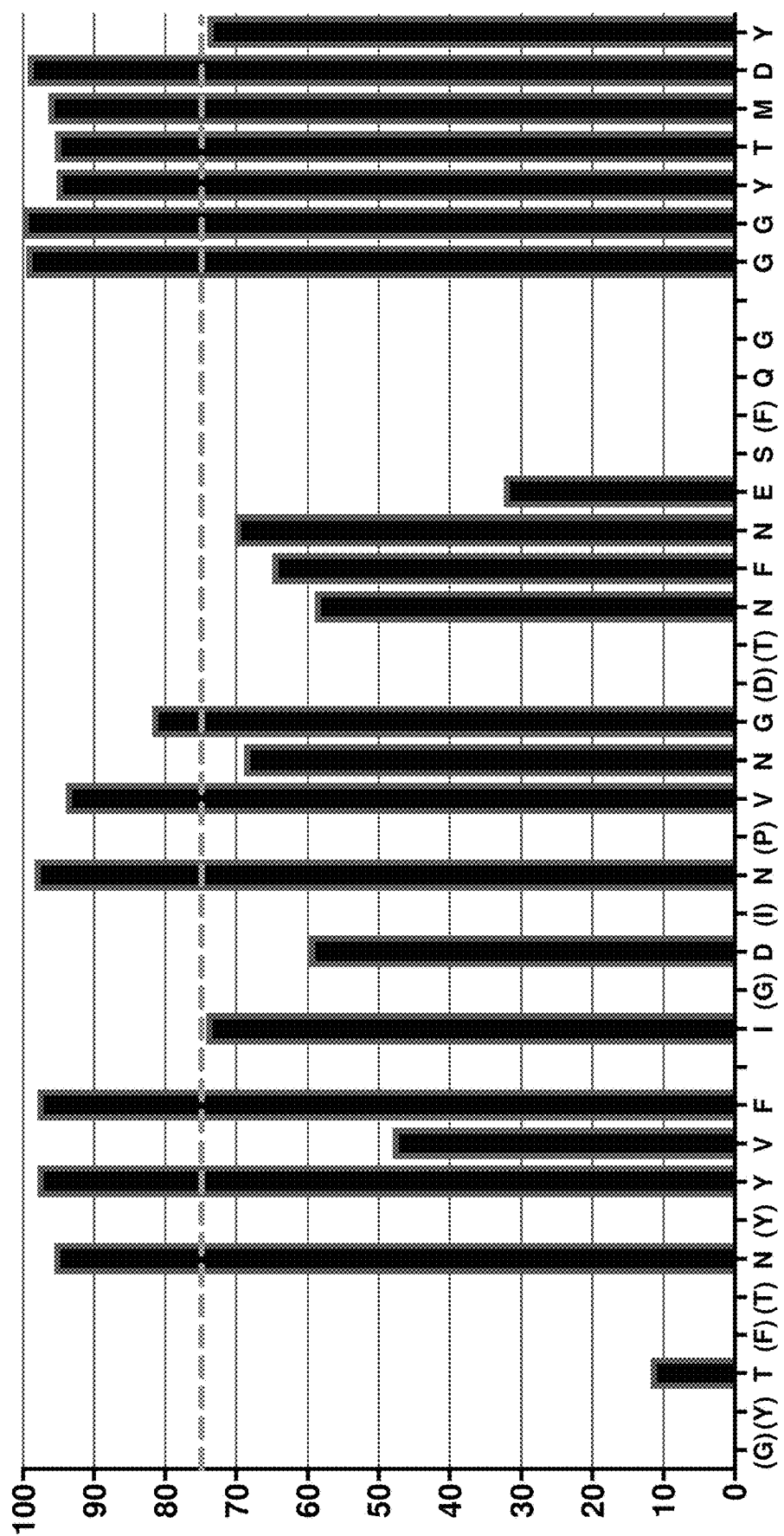
FIG. 2A-FIG. 2B. Analysis of CDR residue tolerance for mutation to germline. A plot of murine amino acid retention frequencies in the CDRs of the ELISA-positive population of 854 unique scFv clones is shown for $V_H$ (FIG. 2A) and $V_L$ (FIG. 2B) domains, respectively. Only those residues targeted for human/murine residue mutagenesis are plotted, other than in the HCDR3. In each plot, CDR residues are shown in the X-axis and the Y-axis shows percentage retention of each murine residue. CDR residues noted in parentheses on the X-axes were identical to those found in the human germlines used for grafting (IGKV2-28 and IGHV5-51). Those residues in the HCDR2 that are not in parentheses, but whose values are set at 0, were mutated to human germline during the grafting process. In both plots the dashed line in grey at 75% represents the cutoff for tolerance of murine residue replacement by human germline.

According to a first aspect of the invention, there is provided an antibody molecule which specifically binds to human CD47 and optionally also to cynomolgus monkey CD47 and/or to mouse CD47, or an antigen-binding portion thereof, wherein the antibody molecule or antigen-binding portion comprises a heavy chain variable region with:

an HCDR1 having amino acids in sequence in the following order: G-Y-T or any amino acid (for example, S, N or R)-F-T or a conservative substitution of T-N or a conservative substitution of N-Y-Y-I or a conservative substitution of I-F or any amino acid (for example, V or G) (SEQ ID NO: 1);

an HCDR2 having amino acids in sequence in the following order: M or a conservative substitution of M-G-I or any amino acid (for example, N, V or D)-I-N or any amino acid (for example, Y)-P-V or any amino acid (for example, G or F)-D or a conservative substitution of D-G or a conservative substitution of G-D-T-N or a conservative substitution of N (for example, R)-Y or a conservative substitution of Y-N or a conservative substitution of N (for example, S)-P-S-F-Q-G (SEQ ID NO: 2); and an HCDR3 having amino acids in sequence in the following order: G-G-Y or any amino acid (for example, H, I, Q or F)-T or any amino acid (for example, V or I)-M or any amino acid (for example, T, R, P, A or L)-D or any amino acid (for example, G)-R or any amino acid (for example, Q, N, Y, S, W, K, A, E, F, H, I, L, M, T or V) (SEQ ID NO: 3).

In aspects of the invention, the HCDR1 of the antibody molecule or antigen-binding portion may exclude the sequence GYTFTNYYVF (SEQ ID NO: 4) (VxP037 murine/humanized antibody HCDR1 disclosed in WO2014/093678A2) and/or the HCDR3 of the antibody molecule or antigen-binding portion may exclude the sequence GGYTMDY (SEQ ID NO: 5) (VxP037 murine/humanized antibody HCDR3 disclosed in WO2014/093678A2).

The antibody molecule or antigen-binding portion thereof according to the invention may further comprise a light chain variable region with:

an LCDR1 having amino acids in sequence in the following order: R-S-S-Q or a conservative substitution of Q-S-L or a conservative substitution of L-L or a conservative substitution of L-H-S-N or any amino acid (for example, Q, S, T, A or G) or a conservative substitution of N (for example, Q, S, T or G)-G or a conservative substitution of G (for example, A)-Y or any amino acid (for example, N or S)-T or a conservative substitution of T (for example, N)-Y-L-H or any amino acid (for example, D) (SEQ ID NO: 6);

an LCDR2 having amino acids in sequence in the following order: K or any amino acid (for example, L or M)-V or any amino acid (for example, G)-S-N or any amino acid (for example, Y)-R-L or any amino acid (for example, F, A or S)-S (SEQ ID NO: 7); and an LCDR3 having amino acids in sequence in the following order: F or any amino acid (for example, L, M, S, T or V)-Q-Q or any amino acid (for example, N, A, T or S)-T or any amino acid (for example, L, M or I)-H or a conservative substitution of H-T or any amino acid (for example, V, I, A or F)-P or any amino acid (for example, L)-R or any amino acid (for example, W)-T (SEQ ID NO: 8).

In aspects of the invention, the LCDR1 of the antibody molecule or antigen-binding portion may exclude the sequence RSSQSLVHSNGNTYLH (SEQ ID NO: 9) (VxP037 murine/humanized antibody LCDR1 disclosed in WO2014/093678A2), and/or the LCDR2 of the antibody molecule or antigen-binding portion may exclude the sequence KVSYRFS (SEQ ID NO: 10) (VxP037 murine/humanized antibody LCDR2 disclosed in WO2014/093678A2) and/or the LCDR3 of the antibody molecule or antigen-binding portion may exclude the sequence SQNTHVPRT (SEQ ID NO: 11) (VxP037 murine/humanized antibody LCDR3 disclosed in WO2014/093678A2).

The CDR sequences above are defined using the "Unified" definition, as set out in Table 1. As an alternative, the CDR sequences in the present invention may be defined using the shorter "AHo" definition (see Table 1), which is based on structural biology and aims to unify nomenclature for all immunoglobulin v-domains.

Using the shorter "AHo" definition, the invention in one aspect provides an antibody molecule which specifically binds to human CD47, and optionally also to cynomolgus monkey CD47 and/or to mouse CD47, or an antigen-binding portion thereof, wherein the antibody molecule or antigen-binding portion comprises a heavy chain variable region with:

an HCDR1 having amino acids in sequence in the following order: G-S-G-Y-T or any amino acid (for example, S, N or R)-F-T or a conservative substitution of T-N or a conservative substitution of N-Y-Y (SEQ ID NO: 12);

an HCDR2 having amino acids in sequence in the following order: I-N or any amino acid (for example, Y)-P-V or any amino acid (for example, G or F)-D or a conservative substitution of G-D or a conservative substitution of G-D-T-N or a conservative substitution of N (for example, R)-Y or a conservative substitution of Y-N or a conservative substitution of N (for example, S)-P-S-F-Q-G (SEQ ID NO: 13); and an HCDR3 having amino acids in sequence in the following order: G-G-Y or any amino acid (for example, H, I, Q or F)-T or any amino acid (for example, V or I)-M or any amino acid (for example, T, R, P, A or L)-D or any amino acid (for example, G) (SEQ ID NO: 14).

Using the AHo definition, the HCDR1 of the antibody molecule or antigen-binding portion may exclude the sequence GSGYTFTNYY (SEQ ID NO: 15) (VxP037 murine/humanized antibody HCDR1 disclosed in WO2014/093678A2) and/or the HCDR3 of the antibody molecule or antigen-binding portion may exclude the sequence GGYTMD (SEQ ID NO: 16) (VxP037 murine/humanized antibody HCDR3 disclosed in WO2014/093678A2).

The antibody molecule or antigen-binding portion may further comprise a light chain variable region with:

an LCDR1 having amino acids in sequence in the following order: S-S-Q or a conservative substitution of Q-S-L or a conservative substitution of L-L or a conservative substitution of L-H-S-N or any amino acid (for example, Q, S, T, A or G) or a conservative substitution of N (for example, Q, S, T or G)-G or a conservative substitution of G (for example, A)-Y or any amino acid (for example, N or S)-T or a conservative substitution of T (for example, N)-Y (SEQ ID NO: 17);

an LCDR2 having amino acids in sequence in the following order: K or any amino acid (for example, L or M)-V or any amino acid (for example, G)-S-N or any amino acid (for example, Y)-R-L or any amino acid (for example, F, A or S)-S (SEQ ID NO: 7); and an LCDR3 having amino acids in sequence in the following order: Q or any amino acid (for example, N, A, T or S)-T or any amino acid (for example, L, M or I)-H or a conservative substitution of H-T or any amino acid (for example, V, I, A or F)-P or any amino acid (for example, L)-R or any amino acid (for example, W) (SEQ ID NO: 18).

Using the AHo definition, in aspects of the invention the LCDR1 of the antibody molecule or antigen-binding portion may exclude the sequence SSQSLVHSNGNTY (SEQ ID NO: 19) (VxP037 murine/humanized antibody LCDR1 disclosed in WO2014/093678A2), and/or the LCDR2 of the antibody molecule or antigen-binding portion may exclude the sequence KVSYRFS (SEQ ID NO: 10) (VxP037 murine/humanized antibody LCDR2 disclosed in WO2014/093678A2) and/or the LCDR3 of the antibody molecule or antigen-binding portion may exclude the sequence NTHVPR (SEQ ID NO: 20) (VxP037 murine/humanized antibody LCDR3 disclosed in WO2014/093678A2).

As elaborated herein, the present inventors have succeeded for the first time in generating a number of optimized anti-CD47 antibody molecules using CDR sequences derived from the murine anti-CD47 antibody VxP037 disclosed in WO2014/093678A2. In embodiments of the present invention, these antibody molecules have been selected to have binding specificity to both human CD47 as well as cynomolgus monkey CD47 and, for some clones, also to mouse CD47 (to facilitate studies in an animal test species). Further refining of the optimized antibody molecules as described herein has provided improved binding to the mouse orthologue of CD47, improved potency in neutralisation of mouse CD47-SIRPa signalling, improved variable domain stability, high expression yields, and/or reduced immunogenicity. For example, we demonstrate herein that the progenitor molecule for the murine anti-CD47 antibody VxP037 carries two major immunogenicity risks in the LCDR1 and LCDR2 that will be carried through with classical humanization techniques (as used in WO2014/093678A2) but are ameliorated in optimized antibody molecules as described herein.

The antibody molecule or antigen-binding portion of the present invention may have improved in silico immunogenicity compared with an antibody molecule comprising the CDR sequences of SEQ ID NOs: 4 (HCDR1), 123 (HCDR2), 5 (HCDR3), 9 (LCDR1), 10 (LCDR2) and 11 (LCDR3).

The antibody molecule or antigen-binding portion of the present invention may exhibit no binding to hamster CD47, or exhibit reduced binding to hamster CD47 compared with an antibody molecule comprising the CDR sequences of SEQ ID NOs: 4 (HCDR1), 123 (HCDR2), 5 (HCDR3), 9 (LCDR1), 10 (LCDR2) and 11 (LCDR3). For example, the antibody molecule or antigen-binding portion of the present invention may exhibit no binding to CHO cells as measured by flow cytometry, or reduced binding to CHO cells as measured by flow cytometry, compared with an antibody comprising the CDR sequences of SEQ ID NOs: 4 (HCDR1), 123 (HCDR2), 5 (HCDR3), 9 (LCDR1), 10 (LCDR2) and 11 (LCDR3). As shown in FIG. 15, representative antibody molecules of the present invention have little or no cross-reactivity with CHO cells, whereas the original murine v-domains of clone mVH/mVL in either IgG1null or IgG4 format drive strong, concentration-dependent binding to CHO cells.

Preferred optimized anti-CD47 antibody molecules of the present invention do not necessarily have the maximum number of human germline substitutions at corresponding murine CDR or other (such as framework) amino acid positions. As elaborated in the experimental section below, we have found that "maximally humanized" antibody molecules are not necessary "maximally optimized" in terms of anti-CD47 binding characteristics and/or other desirable features.

The present invention encompasses modifications to the amino acid sequence of the antibody molecule or antigen-binding portion thereof as defined herein. For example, the invention includes antibody molecules and corresponding antigen-binding portions thereof comprising functionally equivalent variable regions and CDRs which do not significantly affect their properties as well as variants which have enhanced or decreased activity and/or affinity. For example, the amino acid sequence may be mutated to obtain an antibody with the desired binding affinity to CD47. Insertions which include amino- and/or carboxyl-terminal fusions ranging in length from one residue to polypeptides containing a hundred or more residues, as well as intrasequence insertions of single or multiple amino acid residues, are envisaged. Examples of terminal insertions include an antibody molecule with an N-terminal methionyl residue or the antibody molecule fused to an epitope tag. Other insertional variants of the antibody molecule include the fusion to the N- or C-terminus of the antibody of an enzyme or a polypeptide which increases the half-life of the antibody in the blood circulation.

The antibody molecule or antigen-binding portion of the invention may include glycosylated and nonglycosylated polypeptides, as well as polypeptides with other post-translational modifications, such as, for example, glycosylation with different sugars, acetylation, and phosphorylation. The antibody molecule or antigen-binding portion of the invention may be mutated to alter such post-translational modifications, for example by adding, removing or replacing one or more amino acid residues to form or remove a glycosylation site.

The antibody molecule or antigen-binding portion of the invention may be modified for example by amino acid substitution to remove potential proteolytic sites in the antibody.

In the antibody molecule or antigen-binding portion thereof, the HCDR1 may have the amino acid sequence: G-Y-T/S/N/R-F-T/N-N/S-Y-Y-I/V-F/V/G (SEQ ID NO: 21); the HCDR2 may have the amino acid sequence: M/I-G-V/N/I/D-I-N/Y-P-V/G/F-N/D-G/S-D-T-N/R/K-F/Y-N/S-P-S-F-Q-G (SEQ ID NO: 22); and the HCDR3 may have the amino acid sequence: G-G-F/H/I/Q/Y-T/V/I-M/T/R/P/A/L-D/G-Y/Q/N/R/S/W/K/A/E/F/H/I/L/M/T/V (SEQ ID NO: 23). Alternatively, using the AHo definition, in the antibody molecule or antigen-binding portion thereof, the HCDR1 may have the amino acid sequence: G-S-G-Y-T/S/N/R-F-T/N-N/S-Y-Y (SEQ ID NO: 24); the HCDR2 may have the amino acid sequence: I-N/Y-P-V/G/F-N/D-G/S-D-T-N/R/K-F/Y-N/S-P-S-F-Q-G (SEQ ID NO: 25); and the HCDR3 may have the amino acid sequence: G-G-F/H/I/Q/Y-T/V/I-M/T/R/P/A/L-D/G (SEQ ID NO: 26).

For example, the HCDR1 may have the amino acid sequence: G-Y-T/S-F-T-N-Y-Y-I-F (SEQ ID NO: 27); the HCDR2 may have the amino acid sequence: M/I-G-I/D-I-N-P-V-N/D-G-D-T-N/R-F/Y-N/S-P-S-F-Q-G (SEQ ID NO: 28); and the HCDR3 may have the amino acid sequence: G-G-F/Y-T-M/P-D-Y/R/K/I (SEQ ID NO: 29). Alternatively, using the AHo definition, the HCDR1 may have the amino acid sequence: G-S-G-Y-T/S-F-T-N-Y-Y (SEQ ID NO: 30); the HCDR2 may have the amino acid sequence: I-N-P-V-N/D-G-D-T-N/R-F/Y-N/S-P-S-F-Q-G (SEQ ID NO: 31); and the HCDR3 may have the amino acid sequence: G-G-F/Y-T-M/P-D (SEQ ID NO: 32).

In the antibody molecule or antigen-binding portion thereof, the LCDR1 may have the amino acid sequence: R-S-S-Q/H-S-F/L-L/V-H-S-N/Q/A-G/A-Y/N/S-N/T-Y-L-H/D (SEQ ID NO: 33); the LCDR2 may have the amino acid sequence: L/K/M-V/G-S-N/Y-R-A/F/L/S-S (SEQ ID NO: 34); and the LCDR3 may have the amino acid sequence: F/L/M/S/T/V-Q-Q/N/A/T/S-T/L/M/I-Q/H-T/V/I/A/F-P/L-R/W-T (SEQ ID NO: 35). Alternatively, using the AHo definition, in the antibody molecule or antigen-binding portion thereof, the LCDR1 may have the amino acid sequence: S-S-Q/H-S-F/L-L/V-H-S-N/Q/A-G/A-Y/N/S-N/T-Y (SEQ ID NO: 36); the LCDR2 may have the amino acid sequence: L/K/M-V/G-S-N/Y-R-A/F/L/S-S (SEQ ID NO: 34); and the LCDR3 may have the amino acid sequence: Q/N/A/T/S-T/L/M/I-Q/H-T/V/I/A/F-P/L-R/W (SEQ ID NO: 37).

For example, the LCDR1 may have the amino acid sequence: R-S-S-Q-S-L-L/V-H-S-N/Q/A-G-Y/N-N/T-Y-L-H/D (SEQ ID NO: 38); the LCDR2 may have the amino acid sequence: L/K-V/G-S-N/Y-R-A/F/L-S (SEQ ID NO: 39); and the LCDR3 may have the amino acid sequence: F/S-Q-Q/N/A-T/L-Q/H-T/V-P-R-T (SEQ ID NO: 40). Alternatively, using the AHo definition, the LCDR1 may have the amino acid sequence: S-S-Q-S-L-L/V-H-S-N/Q/A-G-Y/N-N/T-Y (SEQ ID NO: 41); the LCDR2 may have the amino acid sequence: L/K-V/G-S-N/Y-R-A/F/L-S (SEQ ID NO: 39); and the LCDR3 may have the amino acid sequence: Q/N/A-T/L-Q/H-T/V-P-R (SEQ ID NO: 42).

In specific embodiments of the invention as defined using the Unified CDR definition, the antibody molecule or antigen-binding portion may comprise:

(a) the amino acid sequences GYSFTNYYIF (SEQ ID NO: 43) (HCDR1), MGDINPVNGDTNYSPSFQG (SEQ ID NO: 44) (HCDR2), GGYTPDY (SEQ ID NO: 45) (HCDR3), RSSQSLLHSNGYNYLH (SEQ ID NO: 46) (LCDR1), KGSNRFS (SEQ ID NO: 47) (LCDR2) and SQNLHVPRT (SEQ ID NO: 48) (LCDR3) [Clone D-H3]; or (b) the amino acid sequences GYTFTNYYIF (SEQ ID NO: 49) (HCDR1), MGIINPVDGDTNYNPSFQG (SEQ ID NO: 50) (HCDR2), GGYTMDR (SEQ ID NO: 51) (HCDR3), RSSQSLLHSNGYTYLH (SEQ ID NO: 52) (LCDR1), KVSNRLS (SEQ ID NO: 53) (LCDR2) and FQNTHTPRT (SEQ ID NO: 54) (LCDR3) [Clone A-D5]; or (c) the amino acid sequences GYSFTNYYIF (SEQ ID NO: 43) (HCDR1), IGDINPVNGDTNFSPSFQG (SEQ ID NO: 55) (HCDR2), GGYTMDK (SEQ ID NO: 56) (HCDR3), RSSQSLVHSNGYTYLH (SEQ ID NO: 57) (LCDR1), KGSYRAS (SEQ ID NO: 58) (LCDR2) and SQNTQTPRT (SEQ ID NO: 59) (LCDR3) [Clone G-B6]; or (d) the amino acid sequences GYSFTNYYIF (SEQ ID NO: 43) (HCDR1), MGIINPVNGDTNYNPSFQG (SEQ ID NO: 60) (HCDR2), GGYTMGK (SEQ ID NO: 61) (HCDR3), RSSQSLVHSNGNTYLD (SEQ ID NO: 62) (LCDR1), KGSYRFS (SEQ ID NO: 63) (LCDR2) and SQATHTPRT (SEQ ID NO: 64) (LCDR3) [Clone F-E7]; or (e) the amino acid sequences GYSFTNYYIF (SEQ ID NO: 43) (HCDR1), MGIINPVDGDTRYSPSFQG (SEQ ID NO: 65) (HCDR2), GGFTMDY (SEQ ID NO: 66) (HCDR3), RSSQSLLHSNGYNYLH (SEQ ID NO: 46) (LCDR1), KGSNRAS (SEQ ID NO: 67) (LCDR2) and SQNTHTPRT (SEQ ID NO: 68) (LCDR3) [Clone VH-A1/VL-B1]; or (f) the amino acid sequences GYSFTNYYIF (SEQ ID NO: 43) (HCDR1), IGIINPVDGDTRYSPSFQG (SEQ ID NO: 69) (HCDR2), GGYTMDI (SEQ ID NO: 70) (HCDR3), RSSQSLLHSNGYNYLH (SEQ ID NO: 46) (LCDR1), LGSNRFS (SEQ ID NO: 71) (LCDR2) and SQNTQTPRT (SEQ ID NO: 59) (LCDR3) [Clone MH]; or (g) the amino acid sequences GYSFTNYYIF (SEQ ID NO: 43) (HCDR1), MGIINPVDGDTRYSPSFQG (SEQ ID NO: 65) (HCDR2), GGYTMDI (SEQ ID NO: 70) (HCDR3), RSSQSLLHSNGYNYLH (SEQ ID NO: 46) (LCDR1), LGSNRAS (SEQ ID NO: 72) (LCDR2) and SQATQTPRT (SEQ ID NO: 73) (LCDR3) [Clone TTP]; or (h) the amino acid sequences GYSFTNYYIF (SEQ ID NO: 43) (HCDR1), MGIINPVDGDTNYNPSFQG (SEQ ID NO: 50) (HCDR2), GGYTMDR (SEQ ID NO: 51) (HCDR3), RSSQSLLHSNGYTYLH (SEQ ID NO: 52) (LCDR1), KVSNRLS (SEQ ID NO: 53) (LCDR2) and FQNTHTPRT (SEQ ID NO: 54) (LCDR3) [Clone A-D5.1]; or (i) the amino acid sequences GYSFTNYYIF (SEQ ID NO: 43) (HCDR1), MGIINPVDGDTRYNPSFQG (SEQ ID NO: 74) (HCDR2), GGYTMDR (SEQ ID NO: 51) (HCDR3), RSSQSLLHSNGYTYLH (SEQ ID NO: 52) (LCDR1), KVSNRLS (SEQ ID NO: 53) (LCDR2) and FQNTHTPRT (SEQ ID NO: 54) (LCDR3) [Clone A-D5.2]; or (j) the amino acid sequences GYSFTNYYIF (SEQ ID NO: 43) (HCDR1), MGIINPVDGDTRYSPSFQG (SEQ ID NO: 65) (HCDR2), GGYTMDR (SEQ ID NO: 51) (HCDR3), RSSQSLLHSNGYTYLH (SEQ ID NO: 52)

(LCDR1), KVSNRLS (SEQ ID NO: 53) (LCDR2) and FQNTHTPRT (SEQ ID NO: 54) (LCDR3) [Clone A-D5.3]; or (k) the amino acid sequences GYTFTNYYIF (SEQ ID NO: 49) (HCDR1), MGIINPVDGDTNYNPSFQG (SEQ ID NO: 50) (HCDR2), GGYTMDR (SEQ ID NO: 51) (HCDR3), RSSQSLLHSNGYNYLH (SEQ ID NO: 46) (LCDR1), KVSNRLS (SEQ ID NO: 53) (LCDR2) and FQNTHTPRT (SEQ ID NO: 54) (LCDR3) [Clone A-D5.4]; or (l) the amino acid sequences GYTFTNYYIF (SEQ ID NO: 49) (HCDR1), MGIINPVDGDTNYNPSFQG (SEQ ID NO: 50) (HCDR2), GGYTMDR (SEQ ID NO: 51) (HCDR3), RSSQSLLHSNGYNYLH (SEQ ID NO: 46) (LCDR1), KGSNRLS (SEQ ID NO: 75) (LCDR2) and FQNTHTPRT (SEQ ID NO: 54) (LCDR3) [Clone A-D5.5]; or (m) the amino acid sequences GYTFTNYYIF (SEQ ID NO: 49) (HCDR1), MGIINPVDGDTNYNPSFQG (SEQ ID NO: 50) (HCDR2), GGYTMDR (SEQ ID NO: 51) (HCDR3), RSSQSLLHSNGYNYLH (SEQ ID NO: 46) (LCDR1), KGSNRLS (SEQ ID NO: 75) (LCDR2) and FQNTQTPRT (SEQ ID NO: 76) (LCDR3) [Clone A-D5.6]; or (n) the amino acid sequences GYTFTNYYIF (SEQ ID NO: 49) (HCDR1), MGIINPVDGDTNYNPSFQG (SEQ ID NO: 50) (HCDR2), GGYTMDR (SEQ ID NO: 51) (HCDR3), RSSQSLLHSNGYNYLH (SEQ ID NO: 46) (LCDR1), LGSNRLS (SEQ ID NO: 77) (LCDR2) and FQNTQTPRT (SEQ ID NO: 76) (LCDR3) [Clone A-D5.7]; or (o) the amino acid sequences GYTFTNYYIF (SEQ ID NO: 49) (HCDR1), MGIINPVDGDTNYNPSFQG (SEQ ID NO: 50) (HCDR2), GGYTMDR (SEQ ID NO: 51) (HCDR3), RSSQSLLHSQGYTYLH (SEQ ID NO: 78) (LCDR1), KVSNRLS (SEQ ID NO: 53) (LCDR2) and FQNTHTPRT (SEQ ID NO: 54) (LCDR3) [Clone A-D5.8]; or (p) the amino acid sequences GYTFTNYYIF (SEQ ID NO: 49) (HCDR1), MGIINPVDGDTNYNPSFQG (SEQ ID NO: 50) (HCDR2), GGYTMDR (SEQ ID NO: 51) (HCDR3), RSSQSLLHSNGYTYLH (SEQ ID NO: 52) (LCDR1), KVSNRLS (SEQ ID NO: 53) (LCDR2) and FQQTHTPRT (SEQ ID NO: 79) (LCDR3) [Clone A-D5.9]; or (q) the amino acid sequences GYTFTNYYIF (SEQ ID NO: 49) (HCDR1), MGIINPVDGDTNYNPSFQG (SEQ ID NO: 50) (HCDR2), GGYTMDR (SEQ ID NO: 51) (HCDR3), RSSQSLLHSQGYTYLH (SEQ ID NO: 78) (LCDR1), KVSNRLS (SEQ ID NO: 53) (LCDR2) and FQQTHTPRT (SEQ ID NO: 79) (LCDR3) [Clone A-D5.10]; or (r) the amino acid sequences GYSFTNYYIF (SEQ ID NO: 43) (HCDR1), MGIINPVDGDTNYNPSFQG (SEQ ID NO: 50) (HCDR2), GGYTMDR (SEQ ID NO: 51) (HCDR3), RSSQSLLHSNGYNYLH (SEQ ID NO: 46) (LCDR1), KVSNRLS (SEQ ID NO: 53) (LCDR2) and FQNTHTPRT (SEQ ID NO: 54) (LCDR3) [Clone A-D5.11]; or (s) the amino acid sequences GYSFTNYYIF (SEQ ID NO: 43) (HCDR1), MGIINPVDGDTRYNPSFQG (SEQ ID NO: 74) (HCDR2), GGYTMDR (SEQ ID NO: 51) (HCDR3), RSSQSLLHSNGYNYLH (SEQ ID NO: 46) (LCDR1), KVSNRLS (SEQ ID NO: 53) (LCDR2) and FQNTHTPRT (SEQ ID NO: 54) (LCDR3) [Clone A-D5.12]; or (t) the amino acid sequences GYSFTNYYIF (SEQ ID NO: 43) (HCDR1), MGIINPVDGDTRYSPSFQG (SEQ ID NO: 65) (HCDR2), GGYTMDR (SEQ ID NO: 51) (HCDR3), RSSQSLLHSNGYNYLH (SEQ ID NO: 46) (LCDR1), KVSNRLS (SEQ ID NO: 53) (LCDR2) and FQNTHTPRT (SEQ ID NO: 54) (LCDR3) [Clone A-D5.13]; or (u) the amino acid sequences GYSFTNYYIF (SEQ ID NO: 43) (HCDR1), MGIINPVDGDTRYSPSFQG (SEQ ID NO: 65) (HCDR2), GGYTMDR (SEQ ID NO: 51) (HCDR3), RSSQSLLHSSGYNYLH (SEQ ID NO: 80) (LCDR1), KVSNRLS (SEQ ID NO: 53) (LCDR2) and FQNTHTPRT (SEQ ID NO: 54) (LCDR3) [Clone A-D5.14]; or (v) the amino acid sequences GYSFTNYYIF (SEQ ID NO: 43) (HCDR1), MGIINPVDGDTRYSPSFQG (SEQ ID NO: 65) (HCDR2), GGYTMDR (SEQ ID NO: 51) (HCDR3), RSSQSLLHSGGYNYLH (SEQ ID NO: 81) (LCDR1), KVSNRLS (SEQ ID NO: 53) (LCDR2) and FQNTHTPRT (SEQ ID NO: 54) (LCDR3) [Clone A-D5.15]; or (w) the amino acid sequences GYSFTNYYIF (SEQ ID NO: 43) (HCDR1), MGIINPVDGDTRYSPSFQG (SEQ ID NO: 65) (HCDR2), GGYTMDR (SEQ ID NO: 51) (HCDR3), RSSQSLLHSAGYNYLH (SEQ ID NO: 82) (LCDR1), KVSNRLS (SEQ ID NO: 53) (LCDR2) and FQNTHTPRT (SEQ ID NO: 54) (LCDR3) [Clone A-D5.16]; or (x) the amino acid sequences GYSFTNYYIF (SEQ ID NO: 43) (HCDR1), MGIINPVDGDTRYSPSFQG (SEQ ID NO: 65) (HCDR2), GGYTMDR (SEQ ID NO: 51) (HCDR3), RSSQSLLHSTGYNYLH (SEQ ID NO: 83) (LCDR1), KVSNRLS (SEQ ID NO: 53) (LCDR2) and FQNTHTPRT (SEQ ID NO: 54) (LCDR3) [Clone A-D5.17]; or (y) the amino acid sequences GYSFTNYYIF (SEQ ID NO: 43) (HCDR1), MGIINPVDGDTRYSPSFQG (SEQ ID NO: 65) (HCDR2), GGYTMDR (SEQ ID NO: 51) (HCDR3), RSSQSLLHSNAYNYLH (SEQ ID NO: 84) (LCDR1), KVSNRLS (SEQ ID NO: 53) (LCDR2) and FQNTHTPRT (SEQ ID NO: 54) (LCDR3) [Clone A-D5.18]; or (z) the amino acid sequences GYSFTNYYIF (SEQ ID NO: 43) (HCDR1), MGIINPVDGDTRYSPSFQG (SEQ ID NO: 65) (HCDR2), GGYTMDR (SEQ ID NO: 51) (HCDR3), RSSQSLLHSAGYNYLH (SEQ ID NO: 82) (LCDR1), KVSNRFS (SEQ ID NO: 85) (LCDR2) and FQNTHTPRT (SEQ ID NO: 54) (LCDR3) [Clone A-D5.16-DI]; or (z.1) the amino acid sequences GYTFTNYYIF (SEQ ID NO: 49) (HCDR1), MGIINPVDGDTNYNPSFQG (SEQ ID NO: 50) (HCDR2), GGYTMDR (SEQ ID NO: 51) (HCDR3), RSSQSLLHSNGYTYLH (SEQ ID NO: 52) (LCDR1), KVSNRFS (SEQ ID NO: 85) (LCDR2) and FQNTHTPRT (SEQ ID NO: 54) (LCDR3) [Clone A-D5-DI].

In the above specific embodiments of the invention, the CDRs may alternatively be defined using the AHo CDR definition such that the antibody molecule or antigen-binding portion comprises:

(a) the amino acid sequences GSGYSFTNYY (SEQ ID NO: 86) (HCDR1), INPVNGDTNYSPSFQG (SEQ ID NO: 87) (HCDR2), GGYTPD (SEQ ID NO: 88) (HCDR3), SSQSLLHSNGYNY (SEQ ID NO: 89) (LCDR1), KGSNRFS (SEQ ID NO: 47) (LCDR2) and NLHVPR (SEQ ID NO: 90) (LCDR3) [Clone D-H3]; or (b) the amino acid sequences GSGYTFTNYY (SEQ ID NO: 15) (HCDR1), INPVDGDTNYNPSFQG (SEQ ID NO: 91) (HCDR2), GGYTMD (SEQ ID NO: 16) (HCDR3), SSQSLLHSNGYTY (SEQ ID NO: 92) (LCDR1), KVSNRLS (SEQ ID NO: 53) (LCDR2) and NTHTPR (SEQ ID NO: 93) (LCDR3) [Clone A-D5]; or (c) the amino acid sequences GSGYSFTNYY (SEQ ID NO: 86) (HCDR1), INPVNGDTNFSPSFQG (SEQ ID NO: 94) (HCDR2), GGYTMD (SEQ ID NO: 16) (HCDR3), SSQSLVHSNGYTY (SEQ ID NO: 95) (LCDR1), KGSYRAS (SEQ ID NO: 58) (LCDR2) and NTQTPR (SEQ ID NO: 96) (LCDR3) [Clone G-B6]; or (d) the amino acid sequences GSGYSFTNYY (SEQ ID NO: 86) (HCDR1), INPVNGDTNYNPSFQG (SEQ ID NO: 97) (HCDR2), GGYTMG (SEQ ID NO: 98) (HCDR3), SSQSLVHSNGNTY (SEQ ID NO: 19) (LCDR1), KGSYRFS (SEQ ID NO: 63) (LCDR2) and ATHTPR (SEQ ID NO: 99) (LCDR3) [Clone F-E7]; or (e) the amino acid sequences GSGYSFTNYY (SEQ ID NO: 86) (HCDR1), INPVDGDTRYSPSFQG (SEQ ID NO: 100) (HCDR2), GGFTMD (SEQ ID NO: 101) (HCDR3), SSQSLLHSNGYNY (SEQ ID NO: 89) (LCDR1), KGSNRAS (SEQ ID NO: 67) (LCDR2) and NTHTPR (SEQ ID NO: 93) (LCDR3) [Clone VH-A1/VL-B1]; or (f) the amino acid sequences GSGYSFTNYY (SEQ ID NO: 86) (HCDR1), INPVDGDTRYSPSFQG (SEQ ID NO: 100) (HCDR2), GGYTMD (SEQ ID NO: 16) (HCDR3), SSQSLLHSNGYNY (SEQ ID NO: 89) (LCDR1), LGSNRFS (SEQ ID NO: 71) (LCDR2) and NTQTPR (SEQ ID NO: 96) (LCDR3) [Clone MH]; or (g) the amino acid sequences GSGYSFTNYY (SEQ ID NO: 86) (HCDR1), INPVDGDTRYSPSFQG (SEQ ID NO: 100) (HCDR2), GGYTMD (SEQ ID NO: 16) (HCDR3), SSQSLLHSNGYNY (SEQ ID NO: 89) (LCDR1), LGSNRAS (SEQ ID NO: 72) (LCDR2) and ATQTPR (SEQ ID NO: 102) (LCDR3) [Clone TTP]; or (h) the amino acid sequences GSGYSFTNYY (SEQ ID NO: 86) (HCDR1), INPVDGDTNYNPSFQG (SEQ ID NO: 91) (HCDR2), GGYTMD (SEQ ID NO: 16) (HCDR3), SSQSLLHSNGYTY (SEQ ID NO: 92) (LCDR1), KVSNRLS (SEQ ID NO: 53) (LCDR2) and NTHTPR (SEQ ID NO: 93) (LCDR3) [Clone A-D5.1]; or (i) the amino acid sequences GSGYSFTNYY (SEQ ID NO: 86) (HCDR1), INPVDGDTRYNPSFQG (SEQ ID NO: 103) (HCDR2), GGYTMD (SEQ ID NO: 16) (HCDR3), SSQSLLHSNGYTY (SEQ ID NO: 92) (LCDR1), KVSNRLS (SEQ ID NO: 53) (LCDR2) and NTHTPR (SEQ ID NO: 93) (LCDR3) [Clone A-D5.2]; or (j) the amino acid sequences GSGYSFTNYY (SEQ ID NO: 86) (HCDR1), INPVDGDTRYSPSFQG (SEQ ID NO: 100) (HCDR2), GGYTMD (SEQ ID NO: 16) (HCDR3), SSQSLLHSNGYTY (SEQ ID NO: 92) (LCDR1), KVSNRLS (SEQ ID NO: 53) (LCDR2) and NTHTPR (SEQ ID NO: 93) (LCDR3) [Clone A-D5.3]; or (k) the amino acid sequences GSGYTFTNYY (SEQ ID NO: 15) (HCDR1), INPVDGDTNYNPSFQG (SEQ ID NO: 91) (HCDR2), GGYTMD (SEQ ID NO: 16) (HCDR3), SSQSLLHSNGYNY (SEQ ID NO: 89) (LCDR1), KVSNRLS (SEQ ID NO: 53) (LCDR2) and NTHTPR (SEQ ID NO: 93) (LCDR3) [Clone A-D5.4]; or (l) the amino acid sequences GSGYTFTNYY (SEQ ID NO: 15) (HCDR1), INPVDGDTNYNPSFQG (SEQ ID NO: 91) (HCDR2), GGYTMD (SEQ ID NO: 16) (HCDR3), SSQSLLHSNGYNY (SEQ ID NO: 89) (LCDR1), KGSNRLS (SEQ ID NO: 75) (LCDR2) and NTHTPR (SEQ ID NO: 93) (LCDR3) [Clone A-D5.5]; or (m) the amino acid sequences GSGYTFTNYY (SEQ ID NO: 15) (HCDR1), INPVDGDTNYNPSFQG (SEQ ID NO: 91) (HCDR2), GGYTMD (SEQ ID NO: 16) (HCDR3), SSQSLLHSNGYNY (SEQ ID NO: 89) (LCDR1), KGSNRLS (SEQ ID NO: 75) (LCDR2) and NTQTPR (SEQ ID NO: 96) (LCDR3) [Clone A-D5.6]; or (n) the amino acid sequences GSGYTFTNYY (SEQ ID NO: 15) (HCDR1), INPVDGDTNYNPSFQG (SEQ ID NO: 91) (HCDR2), GGYTMD (SEQ ID NO: 16) (HCDR3), SSQSLLHSNGYNY (SEQ ID NO: 89) (LCDR1), LGSNRLS (SEQ ID NO: 77) (LCDR2) and NTQTPR (SEQ ID NO: 96) (LCDR3) [Clone A-D5.7]; or (o) the amino acid sequences GSGYTFTNYY (SEQ ID NO: 15) (HCDR1), INPVDGDTNYNPSFQG (SEQ ID NO: 91) (HCDR2), GGYTMD (SEQ ID NO: 16) (HCDR3), SSQSLLHSQGYTY (SEQ ID NO: 104) (LCDR1), KVSNRLS (SEQ ID NO: 53) (LCDR2) and NTHTPR (SEQ ID NO: 93) (LCDR3) [Clone A-D5.8]; or (p) the amino acid sequences GSGYTFTNYY (SEQ ID NO: 15) (HCDR1), INPVDGDTNYNPSFQG (SEQ ID NO: 91) (HCDR2), GGYTMD (SEQ ID NO: 16) (HCDR3), SSQSLLHSNGYTY (SEQ ID NO: 92) (LCDR1), KVSNRLS (SEQ ID NO: 53) (LCDR2) and QTHTPR (SEQ ID NO: 105) (LCDR3) [Clone A-D5.9]; or (q) the amino acid sequences GSGYTFTNYY (SEQ ID NO: 15) (HCDR1), INPVDGDTNYNPSFQG (SEQ ID NO: 91) (HCDR2), GGYTMD (SEQ ID NO: 16) (HCDR3), SSQSLLHSQGYTY (SEQ ID NO: 104) (LCDR1), KVSNRLS (SEQ ID NO: 53) (LCDR2) and QTHTPR (SEQ ID NO: 105) (LCDR3) [Clone A-D5.10]; or (r) the amino acid sequences GSGYSFTNYY (SEQ ID NO: 86) (HCDR1), INPVDGDTNYNPSFQG (SEQ ID NO: 91) (HCDR2), GGYTMD (SEQ ID NO: 16) (HCDR3), SSQSLLHSNGYNY (SEQ ID NO: 89) (LCDR1), KVSNRLS (SEQ ID NO: 53) (LCDR2) and NTHTPR (SEQ ID NO: 93) (LCDR3) [Clone A-D5.11]; or (s) the amino acid sequences GSGYSFTNYY (SEQ ID NO: 86) (HCDR1), INPVDGDTRYNPSFQG (SEQ ID NO: 103) (HCDR2), GGYTMD (SEQ ID NO: 16) (HCDR3), SSQSLLHSNGYNY (SEQ ID NO: 89) (LCDR1), KVSNRLS (SEQ ID NO: 53) (LCDR2) and NTHTPR (SEQ ID NO: 93) (LCDR3) [Clone A-D5.12]; or (t) the amino acid sequences GSGYSFTNYY (SEQ ID NO: 86) (HCDR1), INPVDGDTRYSPSFQG (SEQ ID NO: 100) (HCDR2), GGYTMD (SEQ ID NO: 16) (HCDR3), SSQSLLHSNGYNY (SEQ ID NO: 89) (LCDR1), KVSNRLS (SEQ ID NO: 53) (LCDR2) and NTHTPR (SEQ ID NO: 93) (LCDR3) [Clone A-D5.13]; or (u) the amino acid sequences GSGYSFTNYY (SEQ ID NO: 86) (HCDR1), INPVDGDTRYSPSFQG (SEQ ID NO: 100) (HCDR2), GGYTMD (SEQ ID NO: 16) (HCDR3), SSQSLLHSSGYNY (SEQ ID NO: 106) (LCDR1), KVSNRLS (SEQ ID NO: 53) (LCDR2) and NTHTPR (SEQ ID NO: 93) (LCDR3) [Clone A-D5.14]; or (v) the amino acid sequences GSGYSFTNYY (SEQ ID NO: 86) (HCDR1), INPVDGDTRYSPSFQG (SEQ ID NO: 100) (HCDR2), GGYTMD (SEQ ID NO: 16) (HCDR3), SSQSLLHSGGYNY (SEQ ID NO: 107) (LCDR1), KVSNRLS (SEQ ID NO: 53) (LCDR2) and NTHTPR (SEQ ID NO: 93) (LCDR3) [Clone A-D5.15]; or (w) the amino acid sequences GSGYSFTNYY (SEQ ID NO: 86) (HCDR1), INPVDGDTRYSPSFQG (SEQ ID NO: 100) (HCDR2), GGYTMD (SEQ ID NO: 16) (HCDR3), SSQSLLHSAGYNY (SEQ ID NO: 108) (LCDR1), KVSNRLS (SEQ ID NO: 53) (LCDR2) and NTHTPR (SEQ ID NO: 93) (LCDR3) [Clone A-D5.16]; or (x) the amino acid sequences GSGYSFTNYY (SEQ ID NO: 86) (HCDR1), INPVDGDTRYSPSFQG (SEQ ID NO: 100) (HCDR2), GGYTMD (SEQ ID NO: 16) (HCDR3), SSQSLLHSTGYNY (SEQ ID NO: 109) (LCDR1), KVSNRLS (SEQ ID NO: 53) (LCDR2) and NTHTPR (SEQ ID NO: 93) (LCDR3) [Clone A-D5.17]; or (y) the amino acid sequences GSGYSFTNYY (SEQ ID NO: 86) (HCDR1), INPVDGDTRYSPSFQG (SEQ ID NO: 100) (HCDR2), GGYTMD (SEQ ID NO: 16) (HCDR3), SSQSLLHSNAYNY (SEQ ID NO: 110) (LCDR1), KVSNRLS (SEQ ID NO: 53) (LCDR2) and NTHTPR (SEQ ID NO: 93) (LCDR3) [Clone A-D5.18]; or (z) the amino acid sequences GSGYSFTNYY (SEQ ID NO: 86) (HCDR1), INPVDGDTRYSPSFQG (SEQ ID NO: 100) (HCDR2), GGYTMD (SEQ ID NO: 16) (HCDR3), SSQSLLHSAGYNY (SEQ ID NO: 108) (LCDR1), KVSNRFS (SEQ ID NO: 85) (LCDR2) and NTHTPR (SEQ ID NO: 93) (LCDR3) [Clone A-D5.16-DI]; or (z.1) the amino acid sequences GSGYTFTNYY (SEQ ID NO: 15) (HCDR1), INPVDGDTNYNPSFQG (SEQ ID NO: 91) (HCDR2), GGYTMD (SEQ ID NO: 16) (HCDR3), SSQSLLHSNGYTY (SEQ ID NO: 92) (LCDR1), KVSNRFS (SEQ ID NO: 85) (LCDR2) and NTHTPR (SEQ ID NO: 93) LCDR3) [Clone A-D5-DI].

The antibody molecule or antigen-binding portion of the invention (defined using the AHo definition) may comprise: an HCDR1 having the amino acid sequence GSGYTFTNYY (SEQ ID NO: 15) or GSGYSFTNYY (SEQ ID NO: 86);

an HCDR2 having the amino acid sequence INPVDGDTNYNPSFQG (SEQ ID NO: 91) or INPVDGDTRYSPSFQG (SEQ ID NO: 100); and an HCDR3 having the amino acid sequence GGYTMD (SEQ ID NO: 16), and optionally further comprising:

an LCDR1 having the amino acid sequence SSQSLLHSNGYNY (SEQ ID NO: 89) or SSQSLLHSNGYTY (SEQ ID NO: 92) or SSQSLLHSAGYNY (SEQ ID NO: 108);

an LCDR2 having the amino acid sequence KVSNRLS (SEQ ID NO: 53) or KVSNRFS (SEQ ID NO: 85); and an LCDR3 having the amino acid sequence NTHTPR (SEQ ID NO: 93).

The above antibody molecule or antigen-binding portion may alternatively defined using the equivalent Unified CDR definitions as disclosed herein.

In particular embodiments of the invention, the antibody molecule or antigen-binding portion may comprise the six CDR sequences of Clone A-D5, Clone A-D5.4 or Clone A-D5.16 or Clone A-D5.16-DI or Clone A-D5-DI as defined above, or a suitable combination of the CDR sequences from each of these clones.

For example, in the antibody molecule or antigen-binding portion as defined using the Unified CDR definition, the HCDR1 may have the amino acid sequence: G-Y-T/S-F-T-N-Y-Y-I-F (SEQ ID NO: 27); the HCDR2 may have the amino acid sequence: M-G-I-I-N-P-V-D-G-D-T-N/R-Y-N/S-P-S-F-Q-G (SEQ ID NO: 111); the HCDR3 may have the amino acid sequence: G-G-Y-T-M-D-R (SEQ ID NO: 51); the LCDR1 may have the amino acid sequence: R-S-S-Q-S-L-L-H-S-N/A-G-Y-N/T-Y-L-H (SEQ ID NO: 112); the LCDR2 may have the amino acid sequence: K-V-S-N-R-L/F-S (SEQ ID NO: 113); and the LCDR3 may have the amino acid sequence: F-Q-N-T-H-T-P-R-T (SEQ ID NO: 54).

Alternatively, in the antibody molecule or antigen-binding portion as defined using the AHo definition, the HCDR1 may have the amino acid sequence: G-S-G-Y-T/S-F-T-N-Y-Y (SEQ ID NO: 30); the HCDR2 may have the amino acid sequence: I-N-P-V-D-G-D-T-N/R-Y-N/S-P-S-F-Q-G (SEQ ID NO: 114); the HCDR3 may have the amino acid sequence: G-G-Y-T-M-D (SEQ ID NO: 16); the LCDR1 may have the amino acid sequence: S-S-Q-S-L-L-H-S-N/A-G-Y-N/T-Y (SEQ ID NO: 115); the LCDR2 may have the amino acid sequence: K-V-S-N-R-L/F-S (SEQ ID NO: 113); and the LCDR3 may have the amino acid sequence: N-T-H-T-P-R (SEQ ID NO: 93).

The antibody molecule or antigen-binding portion as defined herein may comprise one or more substitutions, deletions and/or insertions which remove a post-translational modification (PTM) site, for example a glycosylation site (N-linked or O-linked), a deamination site, a phosphorylation site or an isomerisation/fragmentation site.

More than 350 types of PTM are known. Key forms of PTM include phosphorylation, glycosylation (N- and O-linked), sumoylation, palmitoylation, acetylation, sulfation, myristoylation, prenylation and methylation (of K and R residues). Statistical methods to identify putative amino acid sites responsible for specific PTMs are well known in the art (see Zhou et al., 2016, Nature Protocols 1: 1318-1321). Removal of such a site for example by substitution, deletion and/or insertion and then optionally testing (experimentally and/or theoretically) for (a) binding activity and/or (b) loss of the PTM is contemplated.

For example, the VxP037 murine LCDR1 (as defined herein, i.e. the amino acid sequence RSSQSLVHSNGNTYLH (SEQ ID NO: 9)) has been identified to have a putative deamidation site at residue 10 (N) and/or 12 (N). Removal of either of both of these sites at equivalent positions in an LCDR1 of the invention, for example by conservative substitution (such as to S, A, Q or D), is envisaged (as for example in clone A-D5.8, clone A-D5 and other clones in Tables 3 and 4, or clones A-D5.11 to A-D5.18 in Table 5).

Similarly, the VxP037 murine LCDR3 (as defined herein, i.e. the amino acid sequence SQNTHVPRT (SEQ ID NO: 11)) has been identified to have a putative deamidation site at residue 3 (N). Removal of this site at an equivalent position in an LCDR3 of the invention, for example by conservative or non-conservative substitution (such as to A, S, H, D, T, K, G, E, Q or R), is envisaged (as for example in clone F-E7 and other clones in Tables 3 and 4).

Similarly, the VxP037 murine HCDR3 (as defined herein, i.e. the amino acid sequence GGYTMDY (SEQ ID NO: 5)) has been identified to have a putative oxidation site at residue 5 (M). Removal of this site at an equivalent position in an HCDR3 of the invention, for example by conservative or non-conservative substitution (such as to P, A, T, S, L, F, W, V, I, Y or R), is envisaged (as for example in clone D-H3 and other clones in Tables 3 and 4).

The antibody molecule or antigen-binding portion thereof may be human, humanized or chimeric.

The antibody molecule or antigen-binding portion thereof may comprise one or more human variable domain framework scaffolds into which the CDRs have been inserted.

The antibody molecule or antigen-binding portion thereof may comprise an IGHV5-51 human germline scaffold into which the corresponding HCDR sequences have been inserted.

The antibody molecule or antigen-binding portion thereof may comprise an IGKV2-28 human germline scaffold into which the corresponding LCDR sequences have been inserted.

The antibody molecule or antigen-binding portion thereof may comprise an immunologically inert constant region.

The antibody molecule or antigen-binding portion thereof may be a Fab fragment, a F(ab)$_2$ fragment, an Fv fragment, a tetrameric antibody, a tetravalent antibody, a multispecific antibody (for example, a bivalent antibody), a single domain antibody (for example, a shark antibody [V$_{NAR}$ antibody], or a fragment thereof, or a camelid antibody [V$_H$H antibody], or a fragment thereof), a monoclonal antibody or a fusion protein. Antibody molecules and methods for their construction and use are described, in for example Holliger & Hudson (2005, Nature Biotechnol. 23(9): 1126-1136).

In another aspect of the invention, there is provided an immunoconjugate comprising the antibody molecule or antigen-binding portion thereof of the invention as defined herein linked a therapeutic agent.

Examples of suitable therapeutic agents include cytotoxins, radioisotopes, chemotherapeutic agents, immunomodulatory agents, anti-angiogenic agents, antiproliferative agents, pro-apoptotic agents, and cytostatic and cytolytic enzymes (for example RNAses). Further therapeutic agents include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above terms.

Examples of suitable therapeutic agents for use in immunoconjugates include the taxanes, maytansines, CC-1065 and the duocarmycins, the calicheamicins and other enediynes, and the auristatins. Other examples include the antifolates, vinca alkaloids, and the anthracyclines. Plant toxins, other bioactive proteins, enzymes (i.e., ADEPT), radioisotopes, photosensitizers may also be used in immunoconjugates. In addition, conjugates can be made using secondary carriers as the cytotoxic agent, such as liposomes or polymers, Suitable cytotoxins include an agent that inhibits or prevents the function of cells and/or results in destruction of cells. Representative cytotoxins include antibiotics, inhibitors of tubulin polymerization, alkylating agents that bind to and disrupt DNA, and agents that disrupt protein synthesis or the function of essential cellular proteins such as protein kinases, phosphatases, topoisomerases, enzymes, and cyclins.

Representative cytotoxins include, but are not limited to, doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluhdine, pentostatin, broxuhdine, capecitabine, cladhbine, decitabine, floxuhdine, fludarabine, gougerotin, puromycin, tegafur, tiazofuhn, adhamycin, cisplatin, carboplatin, cyclophosphamide, dacarbazine, vinblastine, vincristine, mitoxantrone, bleomycin, mechlorethamine, prednisone, procarbazine, methotrexate, flurouracils, etoposide, taxol, taxol analogs, platins such as cis-platin and carbo-platin, mitomycin, thiotepa, taxanes, vincristine, daunorubicin, epirubicin, actinomycin, authramycin, azaserines, bleomycins, tamoxifen, idarubicin, dolastatins/auristatins, hemiasterlins, esperamicins and maytansinoids.

Suitable immunomodulatory agents include anti-hormones that block hormone action on tumors and immunosuppressive agents that suppress cytokine production, down-regulate self-antigen expression, or mask MHC antigens.

Also provided is a nucleic acid molecule encoding the antibody molecule or antigen-binding portion thereof of the invention as defined herein.

Further provided is a vector comprising the nucleic acid molecule of the invention as defined herein.

Also provided is a host cell comprising the nucleic acid molecule or the vector of the invention as defined herein.

In a further aspect there is provided a method of producing an anti-CD47 antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

The cancer may for example be selected from the group consisting of: pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an ischemia-reperfusion injury, an autoimmune disease or an inflammatory disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The ischemia-reperfusion injury in all aspect may occur in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting or trauma.

The autoimmune disease or inflammatory disease may be selected from the group consisting of: arthritis, multiple sclerosis, psoriasis, Crohn's disease, inflammatory bowel 'disease, lupus, Grave's disease and Hashimoto's thyroiditis, and ankylosing spondylitis.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an ischemia-reperfusion injury, an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an ischemia-reperfusion injury, an autoimmune disease or an inflammatory disease.

The invention also provides a method for treating or preventing a cardiovascular disease or a fibrotic disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of a cardiovascular disease ora fibrotic disease.

The cardiovascular disease in any aspect of the invention may for example be coronary heart disease or atherosclerosis.

The fibrotic disease in any aspect of the invention may be selected from the group consisting of myocardial infarction, angina, osteoarthritis, pulmonary fibrosis, asthma, cystic fibrosis and bronchitis.

The pharmaceutical composition of the invention may comprise a pharmaceutically acceptable excipient. A pharmaceutically acceptable excipient may be a compound or a combination of compounds entering into a pharmaceutical composition which does not provoke secondary reactions and which allows, for example, facilitation of the administration of the anti-CD47 antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-CD47 antibody molecule.

In some embodiments, the anti-CD47 antibody molecule may be provided in a lyophilised form for reconstitution prior to administration. For example, lyophilised antibody molecules may be re-constituted in sterile water and mixed with saline prior to administration to an individual.

The anti-CD47 antibody molecules will usually be administered in the form of a pharmaceutical composition, which may comprise at least one component in addition to the antibody molecule. Thus pharmaceutical compositions may comprise, in addition to the anti-CD47 antibody molecule, a pharmaceutically acceptable excipient, carrier, buffer, stabilizer or other materials well known to those skilled in the art. Such materials should be non-toxic and should not interfere with the efficacy of the anti-CD47 antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-CD47 antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringe's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-CD47 antibody molecule may be administered alone or in combination with other treatments, either simultaneously or sequentially dependent upon the condition to be treated.

An anti-CD47 antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering the anti-CD47 antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al., 1991, Int. J. Cancer 47: 659-664; Bagshawe K. D. et al., 1991, Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The treatment schedule for an individual may be dependent on the pharmacokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-CD47 antibody molecules as described herein may be administered as sub-cutaneous injections. Sub-cutaneous injections may be administered using an auto-injector, for example for long term prophylaxis/treatment.

In some preferred embodiments, the therapeutic effect of the anti-CD47 antibody molecule may persist for several half-lives, depending on the dose. For example, the therapeutic effect of a single dose of the anti-CD47 antibody molecule may persist in an individual for 1 month or more, 2 months or more, 3 months or more, 4 months or more, 5 months or more, or 6 months or more.

The invention also provides a method of producing an antibody molecule which specifically binds to human CD47 and optionally also to cynomolgus monkey CD47 and/or to mouse CD47, or an antigen-binding portion thereof, comprising the steps of:

(1) grafting anti-CD47 CDRs from a non-human source into a human v-domain framework to produce a humanized anti-CD47 antibody molecule or antigen-binding portion thereof;

(2) generating a phage library of clones of the humanized anti-CD47 antibody molecule or antigen-binding portion thereof comprising one or more mutations in the CDRs;

(3) screening the phage library for binding to human CD47 and optionally also to cynomolgus monkey CD47 and/or to mouse CD47;

(4) selecting clones from the screening step (3) having binding specificity to human CD47 and optionally also to cynomolgus monkey CD47 and/or to mouse CD47; and (5) producing an antibody molecule which specifically binds to human CD47 and optionally also to cynomolgus monkey CD47 and/or to mouse CD47, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization, minimise human T cell epitope content and/or improve manufacturing properties in the antibody molecule or antigen-binding portion thereof produced in step (5).

The method may comprise a further step of assessing immunogenicity of one or more v-domains in the clones selected in step (4) or the antibody molecule produced in step (5), and optionally generating one or more further mutations, for example in a CDR and framework region, to reduce immunogenicity. Immunogenicity may be assessed by identifying the location of T cell epitopes, for example using in silico technologies as described herein.

Refinements applicable to the above method are as described in Example 1 below.

As used herein, the term "CD47" refers to Integrin Associated Protein (IAP) and variants thereof that retain at least part of the biological activity of CD47. As used herein, CD47 includes all mammalian species of native sequence CD47, including human, rat, mouse and chicken. The term "CD47" is used to include variants, isoforms and species homologs of human CD47. Antibodies of the invention may cross-react with CD47 from species other than human, in particular CD47 from cynomolgus monkey (*Macaca fascicularis*). In certain embodiments, the antibodies may be completely specific for human CD47 and may not exhibit non-human cross-reactivity.

As used herein, an "antagonist" as used in the context of the antibody of the invention or an "anti-CD47 antagonist antibody" (interchangeably termed "anti-CD47 antibody") refers to an antibody which is able to bind to CD47 and inhibit CD47 biological activity and/or downstream pathway(s) mediated by CD47 signalling. An anti-CD47 antagonist antibody encompasses antibodies that can block, antagonize, suppress or reduce (including significantly) CD47 biological activity, including downstream pathways mediated by CD47 signalling, such as receptor binding and/or elicitation of a cellular response to CD47. For the purposes of the present invention, it will be explicitly understood that the term "anti-CD47 antagonist antibody" encompass all the terms, titles, and functional states and characteristics whereby CD47 itself, and CD47 biological activity (including but not limited to its ability to enhance the activation of phagocytosis by cells of the myeloid lineage), or the consequences of the activity or biological activity, are substantially nullified, decreased, or neutralized in any meaningful degree.

CD47 "specifically binds" "specifically interacts", "preferentially binds", "binds" or "interacts" with CD47 if it binds with greater affinity, avidity, more readily and/or with greater duration than it binds to other receptors.

An "antibody molecule" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody molecule" encompasses not only intact polyclonal or monoclonal antibodies, but also any antigen binding fragment (for example, an "antigen-binding portion") or single chain thereof, fusion proteins comprising an antibody, and any other modified configuration of the immunoglobulin molecule that comprises an antigen recognition site including, for example without limitation, scFv, single domain antibodies (for example, shark antibodies [$V_{NAR}$ antibodies], or a fragment thereof, and camelid antibodies [$V_H$H antibodies], or a fragments thereof), maxibodies, minibodies, intrabodies, diabodies, triabodies, tetrabodies, and bis-scFv.

An "antibody molecule" encompasses an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), for example IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding portion" of an antibody molecule, as used herein, refers to one or more fragments of an intact antibody that retain the ability to specifically bind to CD47. Antigen binding functions of an antibody molecule can be performed by fragments of an intact antibody. Examples of binding fragments encompassed within the term "antigen binding portion" of an antibody molecule include Fab; Fab'; F(ab')2; an Fd fragment consisting of the VH and CH1 domains; an Fv fragment consisting of the VL and VH domains of a single arm of an antibody; a single domain antibody (dAb) fragment, and an isolated complementarity determining region (CDR).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. The Fc region of an immunoglobulin generally comprises two constant domains, CH2 and CH3. As is known in the art, an Fc region can be present in dimer or monomeric form.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, contribute to the formation of the antigen binding site of antibodies. When choosing FR to flank CDRs, for example when humanizing or optimizing an antibody, FRs from antibodies which contain CDR sequences in the same canonical class are preferred.

The CDR definitions used in the present application combine the domains used in the many disparate, often conflicting schemes that have been created in the field, which are based on the combination of immunoglobulin repertoire analyses and structural analyses of antibodies in isolation and in their co-crystals with antigens (see review by Swindells et al., 2016, abYsis: Integrated Antibody Sequence and Structure-Management, Analysis, and Prediction. J Mol Biol. [PMID: 27561707; Epub 22 Aug. 2016]). The CDR definition used herein (a "Unified" definition) incorporates the lessons of all such prior insights and includes all appropriate loop positions required to sample the full residue landscape that potentially mediates target-binding complementarity.

Table 1 shows the amino acid sequences of the VxP037 murine anti-CD47 antibody CDRs as defined herein (a "Unified" scheme), in comparison to well-known alternative systems for defining the same CDRs.

As used herein the term "conservative substitution" refers to replacement of an amino acid with another amino acid which does not significantly deleteriously change the functional activity. A preferred example of a "conservative substitution" is the replacement of one amino acid with another amino acid which has a value 0 in the following BLOSUM 62 substitution matrix (see Henikoff & Henikoff, 1992, PNAS 89: 10915-10919):

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | 1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |

-continued

|   | A  | R  | N  | D  | C  | Q  | E  | G  | H  | I  | L  | K  | M  | F  | P  | S  | T  | W  | Y  | V  |
|---|----|----|----|----|----|----|----|----|----|----|----|----|----|----|----|----|----|----|----|----|
| W | −3 | −3 | −4 | −4 | −2 | −2 | −3 | −2 | −2 | −3 | −2 | −3 | −1 |  1 | −4 | −3 | −2 | 11 |  2 | −3 |
| Y | −2 | −2 | −2 | −3 | −2 | −1 | −2 | −3 |  2 | −1 | −1 | −2 | −1 |  3 | −3 | −2 | −2 |  2 |  7 | −1 |
| V |  0 | −3 | −3 | −3 | −1 | −2 | −2 | −3 | −3 |  3 |  1 | −2 |  1 | −1 | −2 | −2 |  0 | −3 | −1 |  4. |

The term "monoclonal antibody" (Mab) refers to an antibody, or antigen-binding portion thereof, that is derived from a single copy or clone, including for example any eukaryotic, prokaryotic, or phage clone, and not the method by which it is produced. Preferably, a monoclonal antibody of the invention exists in a homogeneous or substantially homogeneous population.

A "humanized" antibody molecule refers to a form of non-human (for example, murine) antibody molecules, or antigen-binding portion thereof, that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Humanized antibodies may be human immunoglobulins (recipient antibody) in which residues from a CDR of the recipient are replaced by residues from a CDR of a non-human species (donor antibody) such as mouse, rat, or rabbit having the desired specificity, affinity, and capacity.

"Human antibody or fully human antibody" refers to an antibody molecule, or antigen-binding portion thereof, derived from transgenic mice carrying human antibody genes or from human cells.

The term "chimeric antibody" is intended to refer to an antibody molecule, or antigen-binding portion thereof, in which the variable region sequences are derived from one species and the constant region sequences are derived from another species, such as an antibody molecule in which the variable region sequences are derived from a mouse antibody and the constant region sequences are derived from a human antibody.

"Antibody-drug conjugate" and "immunoconjugate" refer to an antibody molecule, or antigen-binding portion thereof, including antibody derivatives that binds to CD47 and is conjugated to cytotoxic, cytostatic and/or therapeutic agents.

Antibody molecules of the invention, or antigen-binding portion thereof, can be produced using techniques well known in the art, for example recombinant technologies, phage display technologies, synthetic technologies or combinations of such technologies or other technologies readily known in the art.

The term "epitope" refers to that portion of a molecule capable of being recognized by and bound by an antibody molecule, or antigen-binding portion thereof, at one or more of the antibody molecule's antigen-binding regions. Epitopes can consist of defined regions of primary secondary or tertiary protein structure and includes combinations of secondary structural units or structural domains of the target recognised by the antigen binding regions of the antibody, or antigen-binding portion thereof. Epitopes can likewise consist of a defined chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody molecule can specifically bind as determined by any method well known in the art, for example, by conventional immunoassays, antibody competitive binding assays or by x-ray crystallography or related structural determination methods (for example NMR).

The term "binding affinity" or "KD" refers to the dissociation rate of a particular antigen-antibody interaction. The KD is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 µM indicates weak binding affinity compared to a $K_D$ of 1 nM. KD values for antibodies can be determined using methods well established in the art. One method for determining the KD of an antibody is by using surface plasmon resonance (SPR), typically using a biosensor system such as a Biacore® system.

The term "potency" is a measurement of biological activity and may be designated as $IC_{50}$, or effective concentration of an antibody or antibody drug conjugate to the antigen CD47 to inhibit 50% of activity measured in a CD47 activity assay as described herein.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The term "inhibit" or "neutralize" as used herein with respect to bioactivity of an antibody molecule of the invention means the ability of the antibody to substantially antagonize, prohibit, prevent, restrain, slow, disrupt, eliminate, stop, reduce or reverse for example progression or severity of that which is being inhibited including, but not limited to, a biological activity or binding interaction of the antibody molecule to CD47.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as defined above. The term "treating" also includes adjuvant and neo-adjuvant treatment of a subject. For the avoidance of doubt, reference herein to "treatment" includes reference to curative, palliative and prophylactic treatment. For the avoidance of doubt, references herein to "treatment" also include references to curative, palliative and prophylactic treatment.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The practice of the present invention will employ, unless otherwise indicated, conventional techniques of molecular biology (including recombinant techniques), microbiology, cell biology, biochemistry and immunology, which are within the skill of the art.

Particular non-limiting embodiments of the present invention will now be described with reference to accompanying drawings.

Example 1. Generation and Characterisation of Optimized Anti-CD47 Therapeutic Antibodies Introduction In this example, we successfully generate a panel of antagonistic, optimized anti-CD47 antibodies. These anti-CD47 antibodies are well expressed, biophysically stable, highly soluble and of maximized identity to preferred human germlines.

Materials and Methods

IgG Cloning, Transient Expression, Purification

Antibody v-domain encoding DNA sequences were cloned via restriction-ligation cloning into separate IgG heavy and light-chain expression cassettes in separate plasmid vectors. Antibodies were expressed in two forms of engineered human IgG: IgG4 with the S228P mutation to stabilise the IgG4 hinge, and IgG1null-IgG1 with the lower hinge mutations L234A/L235A/G237A, which minimise Fcγ receptor-driven effector functions. IgGs were expressed in HEK-293expi cells after transient transfection with endotoxin-free IgG expression plasmid preparations, per manufacturer's protocols. IgGs were purified using a single-step protocol: Conditioned media were loaded (neat) onto a 1 ml ProA sepharose column, pre-equilibrated in PBS pH7.4. The column was washed with 5 column volumes of PBS pH7.4, before the protein was eluted with 100 mM glycine, pH 2.7 and subjected to dialysis in PBS pH 7.4 using 30 kDa cutoff dialysis membrane.

IgG Titration Binding ELISAs

To coat Greiner Bio-One High bind ELISA plates, target proteins were diluted to 1 µg/ml in carbonate buffer and added at 100 µl per well, at 4° C., o/n. Coated plates were washed 3× with PBS pH7.4, blocked with 1% BSA in PBS (380 µl/well) for 1 hr at RT, then washed 3× with PBS-Tween 20 (PBST). CD47 antibodies (100 µl/well; diluted in PBST) were then added and then incubated 1 hr at RT. Plates were then washed 3× with PBST and goat anti-human kappa chain-HRP added (100 µl/well) at RT, for 1 hr. Plates were then washed 3× with PBST and twice with PBS before the addition of 100 µl TMB per well. Reactions were stopped by adding 100 µl 2M $H_2SO_4$/well and OD was read on a plate reader at 450 nm.

Anti-CD47 antibodies were tested for polyreactivity by ELISA. Purified, recombinant, target and non-target antigens were coated in 96-well Nunc maxisorp plates at 100 ng per well in carbonate buffer, at 4° C. overnight. Plates were then washed 3× with PBS, blocked with 1% BSA in PBS, then washed 3× with PBS-Tween20. A dilution series of primary antibodies was then applied, plates were washed 3× with PBS-Tween20 followed by application of goat anti-human kappa chain-HRP 1:4,000 secondary antibody. Wells were then washed 3× with PBS-Tween20 and 2× with PBS, 100 µl TMB peroxidase substrate was added per well, the reaction was stopped by adding 100 µl 2M $H_2SO_4$ and absorbances were read at 450 nm. IgG binding analysis via ELISA on negatively charged biomolecular surfaces were performed as previously described (see Mouquet et al., 2010, Nature 467: 591-595).

CD47 Library Generation and Selection

The CD47 scFv repertoire was assembled by mass oligo synthesis and PCR. The amplified scFv repertoire was then cloned via restriction-ligation into a phagemid vector, transformed into E. coli TG-1 cells, and the phage repertoire rescued essentially as previously described in detail (Finlay et al., 2011, Methods Mol Biol 681: 383-401).

Phage selections were performed by coating streptavidin magnetic microbeads with CD47-Fc protein (either human or cyno), washing the beads thrice with PBS and resuspending in PBS pH7.4 plus 5% skim milk protein (MPBS). These beads were coated at 200 nM target protein in round 1 of selection, followed by 100, 50 and 10 nM in subsequent rounds.

CD47-SIRPα Binding Competition Assay

A competition ELISA assay was established to examine the capacity of optimized leads to block the binding interaction of CD47 with SIRPα. To coat Greiner Bio-One High bind ELISA plates, 10 µg/ml human SIRPα-Fc in carbonate coating buffer was added at 100 µl per well, at 4° C., o/n. Coated plates were washed 3× with PBS pH7.4, blocked with 1% BSA in PBS (380 µl/well) for 1 hr at RT, then washed 3× with PBS-Tween 20 (PBST). Biotinylated human, mouse or cyno CD47-Fc was then added at 0.2 µg/ml in PBS, 100 µl per well, at room temperature for 60 minutes with or without the addition of competing IgGs. Plates were then washed 3× with PBST and Streptavidin-HRP added (100 µl/well) at room temperature, for 1 hr. Plates were then washed 3× with PBST and twice with PBS before the addition of 100 µl TMB per well. Reactions were stopped by adding 100 µl 2M $H_2SO_4$/well and OD was read on a plate reader at 450 nm.

Antibody V-Domain T Cell Epitope Content: In Silico Analyses

In silico technologies (Abzena, Ltd.), which are based on identifying the location of T cell epitopes in therapeutic antibodies and proteins, were used for assessing potential immunogenicity in antibody v-domains. iTope™ was used to analyse the VL and VH sequences of key leads for peptides with promiscuous high affinity binding to human MHC class II. Promiscuous high affinity MHC class II binding peptides are thought to correlate with the presence of T cell epitopes that are high risk indicators for clinical immunogenicity of drug proteins. The iTope™ software predicts favourable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9 mer peptides that overlap by eight amino acids spanning the test protein sequence. This process successfully discriminates with high accuracy between peptides that either bind or do not bind MHC class II molecules.

In addition, the sequences were analysed using TCED™ (T Cell Epitope Database™) search for matches to T cell epitopes previously identified by in vitro human T cell epitope mapping analyses of other protein sequences. The TCED™ is used to search any test sequence against a large (>10,000 peptides) database of peptides derived from unrelated protein and antibody sequences.

Cancer Cell Phagocytosis Analysis

Human peripheral blood mononuclear cells (PBMCs) were isolated from whole blood by density gradient centrifugation. CD14+ PBMCs were subsequently isolated via magnetic cell isolation using CD14 microbeads. In parallel, HL-60 cells were labelled using a green CFSE (carboxyfluorescein diacetate, succinimidyl ester) cell tracer dye. A total of $1.25 \times 10^6$ labelled HL-60 cells were pre-incubated in the presence of anti-CD47 antibodies in 24 well plates for 1 hour at 37° C. in a humidified atmosphere containing 5% $CO_2$. Following incubation, $5 \times 10^5$ CD14 positive cells were added to each well and incubated for a further hour under the same culture conditions. Cells were harvested by vigorous pipetting, fixed using ice-cold 4% paraformaldehyde for 10 minutes and then blocked with an Fc receptor binding inhibitor monoclonal antibody for 10 minutes. Following the blocking step cells were incubated with an Alexa Fluor 647 (AF647) conjugated anti-human CD14 antibody at room temperature for 30 minutes and fixed a further time in 4% paraformaldehyde for 5 minutes.

Cells were analysed on the BD Fortessa flow cytometer recording side scatter and forward scatter properties along with CFSE and AF647 fluorescence intensity data. Data was captured until at least $1 \times 10^4$ AF647 positive events were recorded. Data were analysed post-acquisition using FlowJo software (version 10.4.2). Briefly, cell debris was gated out by scatter properties (SSC-Area by FSC-Area). Single cells were also gated for by SSC-Area by SSC-Height and then by FSC-Area by FSC-Height. From the remaining single cell population, CFSE and CD14 double positives cells were gated using a quadrant gate placed based on the population of CD14 positive cells in the vehicle treated test. The percentage of CFSE positive cells from the CD14 positive population was calculated and plotted using Graph Pad Prism software (version 7.0a).

Results and Discussion

CDR Grafting onto Preferred Human Germline v-Genes

The CDRs of an antagonistic murine anti-CD47 IgG VP037 (mVH/mVL; see WO2014/093678 and Table 2) were initially introduced to human germline immunoglobulin v-domain framework sequence scaffolds using CDR grafting. To bias our engineering efforts towards final lead therapeutic IgG compounds with optimal drug-like properties, we chose to graft the CDRs of the parental antibody onto "preferred" germline scaffolds IGHV5-51 and IGKV2-28, which are known to have good solubility and are used at high frequency in the expressed human antibody repertoire.

Those scaffolds and grafted CDR definitions are outlined in Table 2. The heavy and light chain sequences for murine anti-CD47 antibody are also shown in Table 2. While this process of CDR grafting is well known, it is still problematic to predict whether a given set of human v-domain sequences will act as suitable acceptor frameworks for non-human CDR grafting. The use of unsuitable frameworks can lead to the loss of target binding function, protein stability issues or even impaired expression of the final IgG. The IGHV5-51/IGKV2-28 graft was therefore taken forward as the template for CDR mutagenesis and selection of improved clones.

Library Generation and Screening

The CDR-grafted IGHV5-51/IGKV2-28 v-domain sequences were combined into a VL-VH scFv format and a mutagenesis library cassette was generated by mass oligo synthesis and assembly. The final scFv library was ligated into a phage display vector and transformed into E. coli via electroporation to generate $1.3 \times 10^9$ independent clones. Library build quality was verified by sequencing 96 clones. This sequencing data showed that the positions encoding either the murine or human germline residue at each position of variance had been effectively sampled at a frequency of approximately 50%. Libraries were rescued using helper phage M13 and selections performed on biotinylated human, mouse and cynomolgus monkey CD47-Fc proteins in three separate branches A, B and C.

Post-selection screening (FIG. 1) and DNA sequencing revealed the presence of 854 unique, human and mouse CD47-binding scFv clones with significantly increased human content within the CDRs, while the framework sequences remained fully germline. Amongst these 854 clones, germ-lining mutations were observed in all CDRs (Table 3). Lead clones were ranked based on level of CDR germ-lining versus ELISA signal for binding to both human and mouse CD47-Fc (FIG. 1). The v-domains of the 4 top clones from this ranking, plus a $5^{th}$ clone ('VH-A1/VL-B1') that combined the two most humanized observed heavy and light chain v-domains were then sub-cloned into IgG expression vectors for further testing as below (Table 4).

While germ-lining mutations were observed in all CDRs for the lead clones derived directly from library selections, it remained possible that sequence analyses might allow further clones to be designed to have maximal humanization. The 854 sequence-unique hits with binding signals against human and mouse protein were therefore used to analyse the retention frequency for murine amino acids in the CDRs of this functionally characterized population. Positional amino acid retention frequency was expressed as a percentage found in the $V_H$ and $V_L$ domains (FIG. 2A&B). Murine residues with RF<75% were regarded as positions that are possibly not essential to the target-binding paratope and are likely to be open to germ-lining, in a series of combinatorial designs.

A design containing only those murine residues with RF>75% was designated "MH" (MH=Maximally Humanized). Another designer clone ('TTP'=Total Theoretically Possible) was also created that combined the 5 most humanized CDRs observed in the population. The MH and TTP clones were generated by gene synthesis and (along with the 4 library-derived clones outlined above and positive control mVH/mVL and negative control isotype-matched non-CD47-reactive v-domains), cloned into human expression vectors for production as IgG1null and IgG4(S228P). All IgGs were readily expressed and purified from transient transfections of HEK-293 cells.

Lead IgG Specificity and Potency Characteristics

The purified IgGs described above were then tested for binding to human, mouse and cyno CD47-Fc in direct titration ELISA format (FIG. 3). Surprisingly, this analysis demonstrated that while clones MH, A-D5, and D-H3 retained binding affinity for all 3 orthologues of CD47, two clones showed reduced binding to mouse CD47 (G-B6 and F-E7), one clone (VHA-1/VL-B1) maintained comparable binding to both human and mouse CD47, but had lost cross-reactivity to mouse CD47, and one clone (TTP) had lost almost all binding function.

In a CD47-SIRPa blockade assay (FIG. 4), A-D5, G-B6, F-E7 and D-H3 all exhibited concentration-dependent blockade of human, mouse and cyno CD47 interaction with SIRPα-Fc in similar concentration ranges as the mVH/mVL IgG1 antibody. Notably, the VH-A1/VL-B1 IgG1 exhibited potent blockade of human and cyno CD47, but no blockade of mouse CD47. Interestingly, clone MH, despite having demonstrated binding to all 3 orthologues of CD47 in ELISA, showed no blockade signal in any assay. Clone TTP was also negative in all blockade assays.

To ensure that that lead clones had not suffered from loss of target specificity during the mutation and reselection process; lead and control IgG1 clones were tested for binding to a panel of 14 purified human proteins from the immunoglobulin superfamily (FIG. 5). All five IgGs exhibited binding signals at 1 μg/ml to CD47-Fc (human OD450 nm>2.0, cyno>2.0, mouse>1.25), and no detectable binding (OD450 nm<0.1) against any other protein. One notable exception was the VH-A1/VI-B1 clone, which again showed strong binding to human and cyno CD47, but no signal against mouse CD47.

Flow Cytometric Analyses of Lead IgG Binding Specificity at the Cell Membrane

Antibodies to CD47 were analysed for concentration-dependent binding at the cell surface via flow cytometry. CHO-K1 cells were stably transfected with either human, mouse or cyno CD47 full-length cDNAs. Anti-CD47 IgGs mVH/mVL, VH-A1/VL-B1, A-D5, G-B6, F-E7 and D-H3, and an isotype control IgG1 were then all tested in IgG1null and IgG4(S228P) formats, alongside a commercial mouse anti-human CD47 monoclonal MS1991, over a concentration range of 100,000-24 ng/ml for binding to human, cyno or wild type control ('wt', i.e. untransfected) CHO-K1. All IgGs other than the isotype control showed concentration-dependent binding to human and cyno CD47+ cells, with a maximum MFI in each case being >10-fold higher than observed signals for binding to untransfected CHO-K1 (FIG. 6). Measurable binding to CHO-K1 wt cells was observed for all clones other than VH-A1/VL-B1, but only at high antibody concentrations.

The mVH/mVL IgGs, however, showed the strongest reactivity with >10-fold higher signal than the 'no antibody' negative control at concentrations as low as 24 ng/ml. This background binding may be indicative of the original mouse antibody VxP037 having not just cross-reactivity to mouse CD47, but also hamster. The minimisation of this cross-reactivity to hamster CD47 is preferable for a therapeutic protein, as antibodies will typically be produced in CHO cell culture for clinical use. High IgG binding affinity for hamster CD47 protein may potentially lead to a significant increase in the content of unwanted co-purified CD47 host cell protein in production runs, which must be removed from the drug product to avoid immunogenicity in patients.

Figure 7:
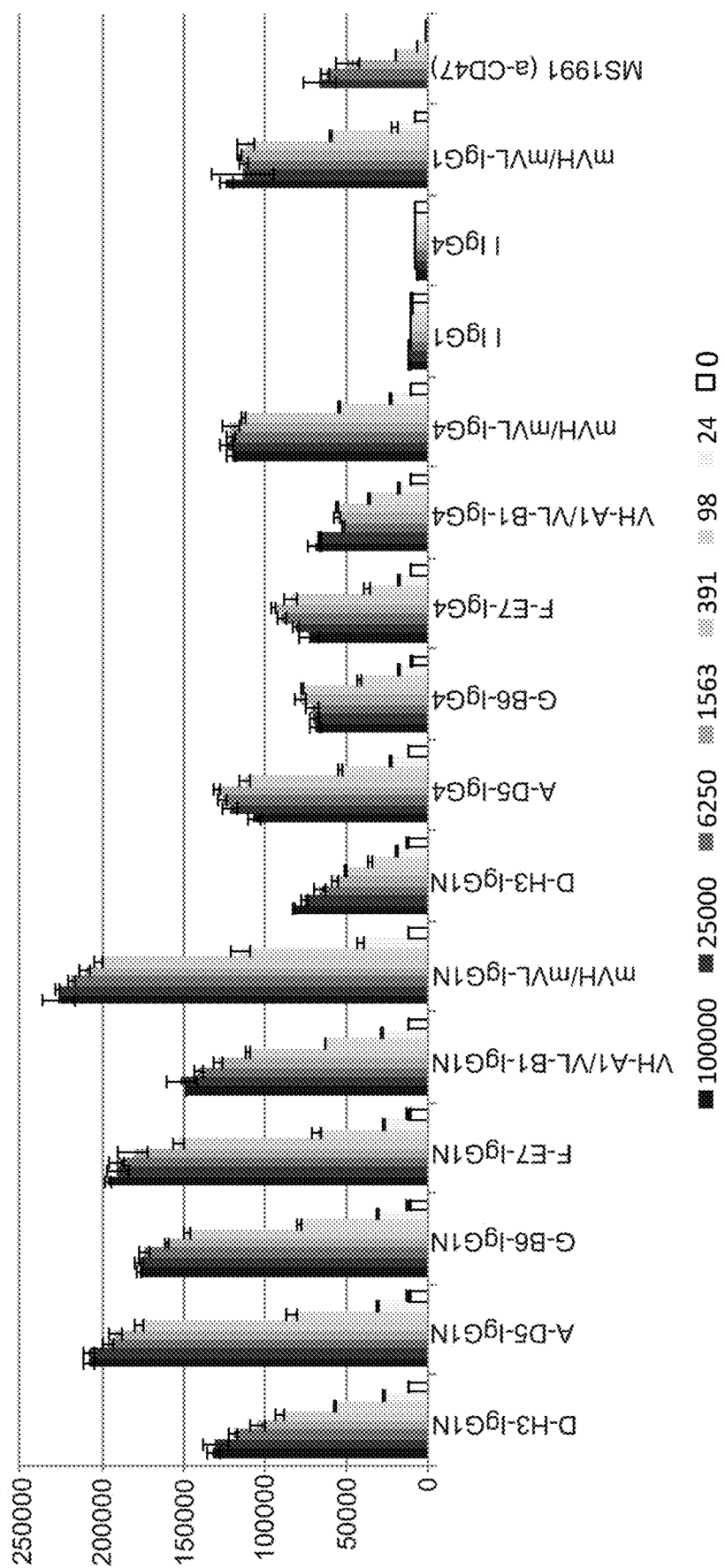
FIG. 7. Flow cytometric testing of binding to human HL60 cells. Commercial anti-CD47 antibody MS1991, human IgG1 and IgG4 Isotype controls ("I IgG1" and "I IgG4", respectively), lead library-derived IgGs in both IgG1null ("IgG1N) and IgG4(S228P) formats were examined for specific binding on HL60 cells. IgGs were tested at concentrations ranging from 24-100000 ng/ml. Concentration-dependent binding was observed for all clones other than the Isotype controls. In each graph, the X-axis shows each IgG tested and its concentration in ng/ml, and the Y-axis shows mean fluorescence intensity (MFI).

To examine the binding of the lead IgGs to CD47+ human cancer cells, HL60 cells (derived from human acute myeloid leukaemia) were also used in flow cytometry analyses, as above. All antibodies other than the Isotype control IgGs showed strong, concentration-dependent binding to the HL60 cells (FIG. 7).

Lead IgG Analyses in 'Developability' ELISA Assays

It is known in the art that the binding of IgGs intended for therapeutic use to several indicative biological substrates is an indicator of high risk for poor performance in patients due to poor bioavailability and short in vivo half-life. Three such biological substrates are Insulin, dsDNA and ssDNA. These three substrates were therefore used to coat ELISA plates and examine the binding of the IgG1null versions of the optimised lead antibodies. Binding signals for these human IgG-based antibodies was compared to 'positive control' human IgG antibodies that have been found to have poly-reactivity and poor performance, which stopped their progress in clinical trials (Bococizumab and Briakinumab human IgG1 analogues). For a negative control human IgG1 antibody, an IgG1 Ustekinumab analogue was used as it reacts with the same therapeutic target as Briakinumab, but has longer pK and was successfully approved as a therapeutic product. In the ELISA analyses shown in FIG. 8, the positive control antibodies exhibited the expected strong reactivity to all 3 substrates, while the negative control showed low reactivity. Importantly, all of the IgG1null lead proteins tested showed binding≤the negative control against all 3 substrates. This finding underlined the maintenance of highly specific, target-driven binding in the optimised clones A-D5, G-B6, D-H3 and VH-A1/VL-B1.

Analyses of Designer IgGs Based on the Lead Clone A-D5

Figure 2B:
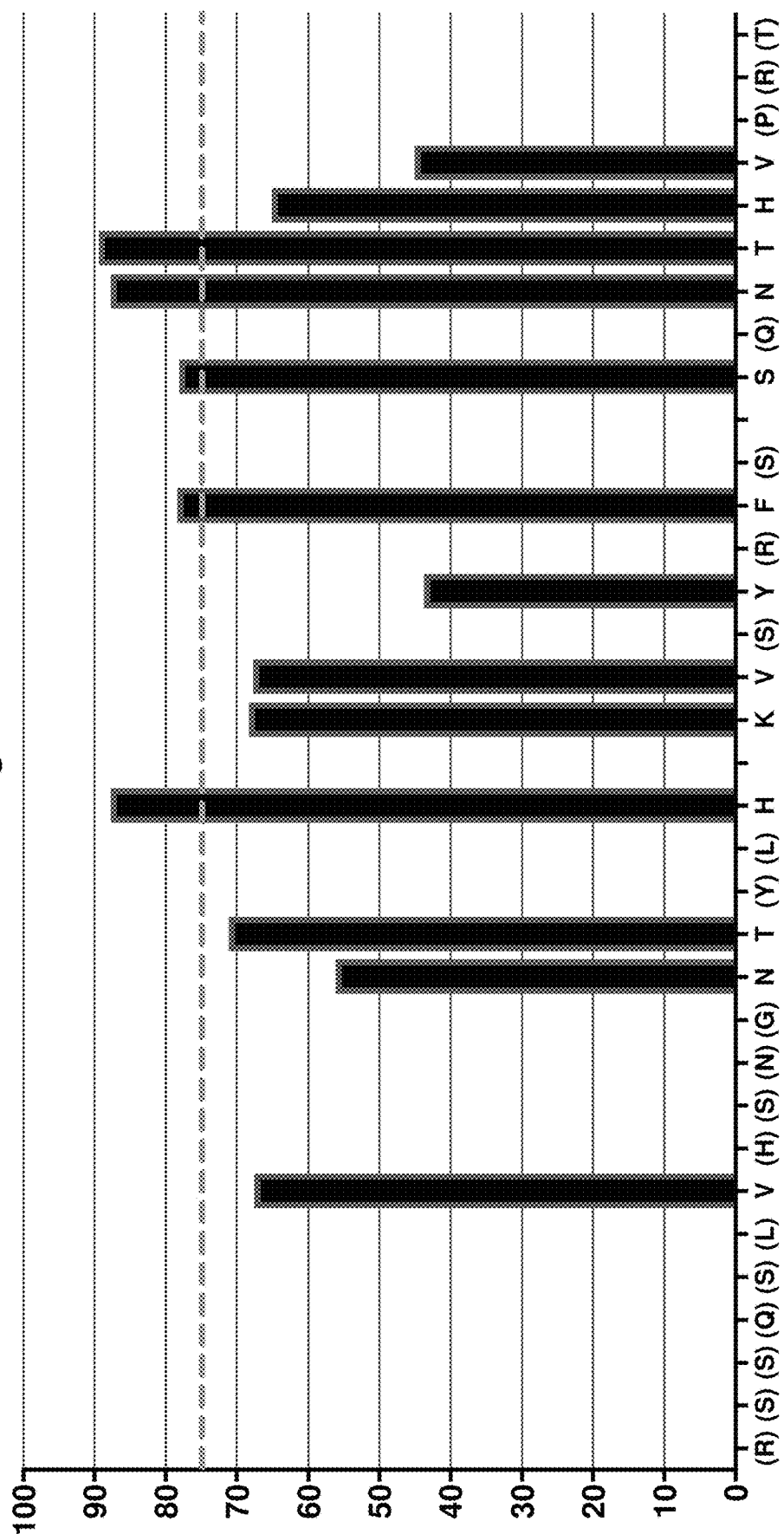

As described above, clone A-D5 had proven to have highly specific binding to human, cyno and mouse CD47, low off-target binding potential, improved neutralisation of mouse CD47, reduced background binding to CHO cells and multiple human germlining mutations in the CDRs. As a library-derived clone, however, the A-D5 sequence still retained a number of non-germline (mouse-derived) residues that were suggested to be potentially superfluous by the data found in FIGS. 2A and 2B. The A-D5 sequence and all other library-derived clones also retained an 'NG' motif in the CDR-L1 that posed high risk for deamidation, as it was found to exhibit high solvent exposure at the apex of the long, flexible, IGKV2-28 germline-template CDR-L1 loop. In an attempt to simultaneously maximise human germline sequence in the variable domains of A-D5 and to minimise high-risk deamidation motif content in the protein, a series of designer clones were created. This effort was carried out in two phases, with the A-D5.1 to A-D5.10 clones from the first phase containing the CDR sequences outlined in Table 4. These clones were expressed and purified in IgG1null format and examined for target binding by ELISA on all CD47 orthologs (FIG. 9A, B, C) and neutralisation of CD47-SIRPa interaction for all orthologs (FIG. 10A, B, C). In this phase, it was found that the human germline and these improvements could be combined with a moderate loss of potency. In addition, the initial mutations attempting to remove the 'NG' motif in the CDR-L1 (via conservative substitution of N to Q) were successful, albeit with associated reductions in potency in both target-binding ELISAs and neutralisation of CD47-SIRPα interaction (FIG. 10A, B, C).

In the second phase, a series of further mutants were designed on the highest-performing mutant from phase 1: A-D5.4 (Table 5). These 9 mutants sampled further humanization of the CDR-H2 of A-D.4, with or without also replacing the 'N' in the 'NG' deamidation risk motif with conservative and non-conservative mutations such as S, G, A and T, or replacing the 'G' residue with A. These clones were again expressed and purified in IgG1null format and examined for target binding by ELISA on all CD47 orthologs (FIG. 11A, B, C) and neutralisation of CD47-SIRPα interaction for all orthologs (FIG. 12A, B, C). In this phase, it was found that the human germline content of the CDR-H2 could be raised by 2 further residues, without loss of potency in comparison to clone A-D5. In addition, the mutations attempting to remove the 'NG' motif in the CDR-L1 via substitution of N were successful, leading to identification of the clone A-D5.16 which contained the non-conservative N to A mutation, plus the maximally humanized CDR-H2, with only minor (approximately 3-fold) reductions in potency in either target-binding ELISAs or neutralisation of CD47-SIRPα, versus both A-D5 and mVL/mVH. The CDR-L1 sequence of A-D.16 'RSSQSLLHSAGYNYLH' (SEQ ID NO: 82) (and clones A-D5.14, A-D5.15, A-D5.17 and A-D5.28) contained non-germline residues at only two positions (underlined) and achieved an optimized balance between maximum human germline content and maximum stability characteristics.

Figure 13A:
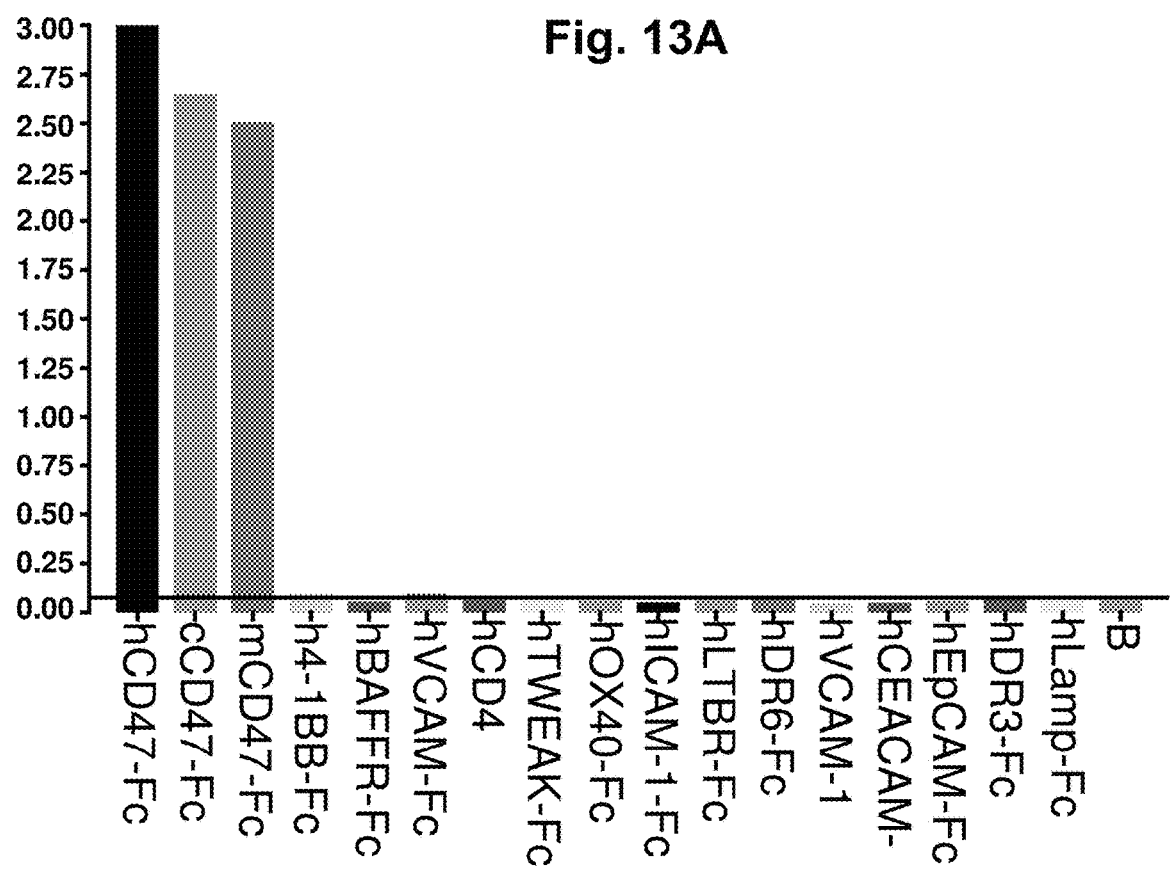
FIG. 13A-FIG. 13B. Binding specificity analyses for designer clones A-D5.4 and A-D5.16. Off-target homologue binding risk for A-D5.4 (FIG. 13A) and A-D5.16 (FIG. 13B) in IgG1null format was examined by direct ELISA on CD47-Fc orthologs and a panel of 14 human immunoglobulin superfamily proteins (as labelled on each X-axis; "B" refers to blank). Binding to all proteins was performed at an IgG concentration of 10 µg/ml. In each plot, the Y-axis shows binding signal (OD 450 nm). For both IgGs, binding was observed to hCD47-Fc, mCD37-Fc and cCD47-Fc alone. No binding above background was observed for any other human protein.
Figure 13B:
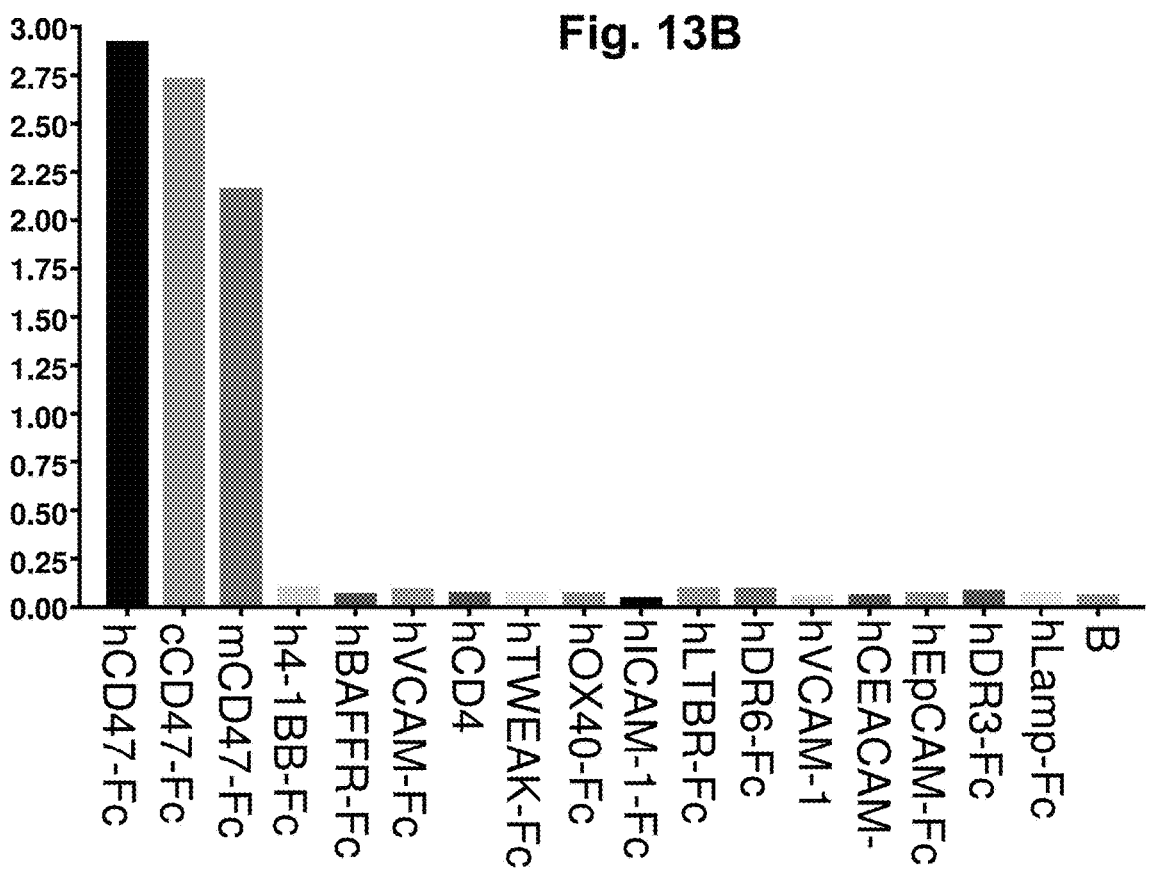
Figure 14A:
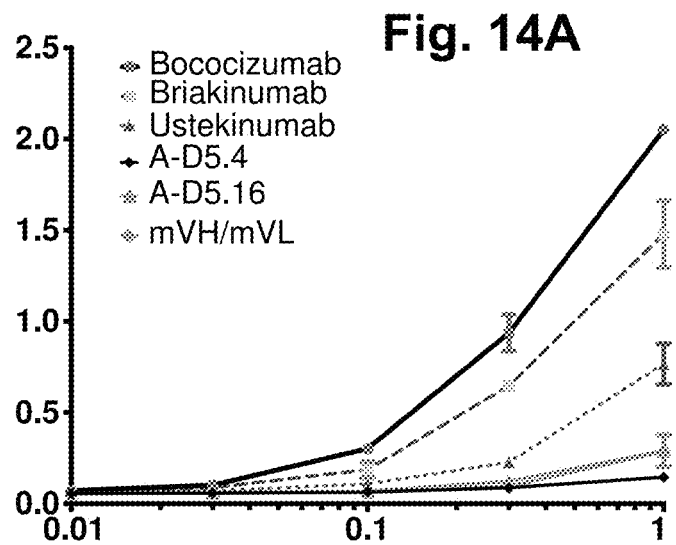
FIG. 14A-FIG. 14C. Development risk ELISAs for designer clones A-D5.4 and A-D5.16. This assay showed that the A-D5.4 and A-D5.16 antibodies in IgG1null form exhibit low (below negative control, Ustekinumab) binding to the negatively charged biomolecules Insulin (FIG. 14A), double-stranded DNA (dsDNA) (FIG. 14B) and single-stranded DNA (ssDNA) (FIG. 14C). In each graph, the X-axis shows IgG concentration in µg/ml and the Y-axis shows binding signal (OD 450 nm). Strong off-target binding to these molecules, as observed for Bococizumab and Briakinumab analogues has been shown to be a high-risk indicator of poor clinical performance of therapeutic antibodies.
Figure 14B:
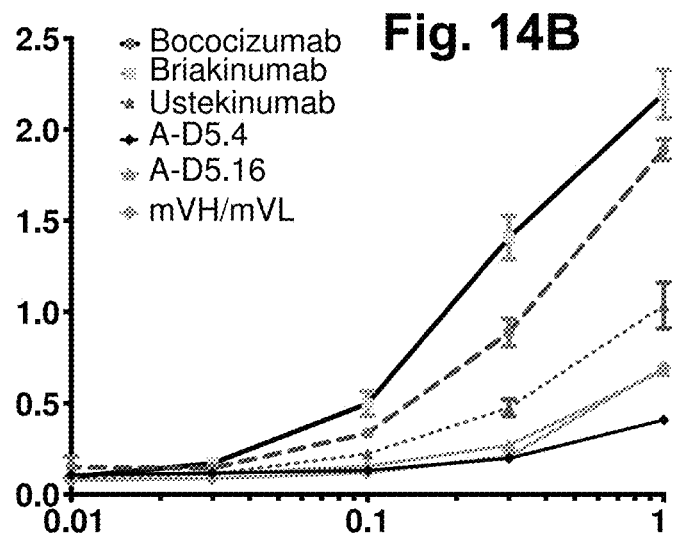
Figure 14C:
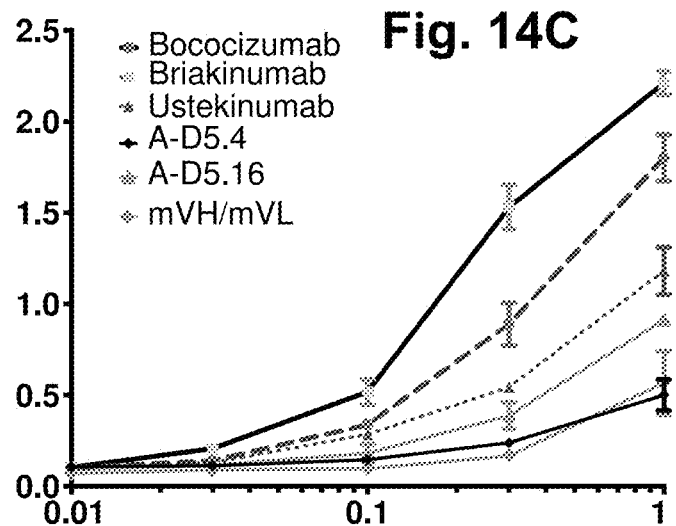

The A-D5 derivatives A-D5.4 and A-D5.16 were subsequently also tested in IgG1null format for maintenance of binding specificity to ensure that there had been no loss of target specificity during the mutation and reselection process; both clones were tested for binding to a panel of 14 purified human proteins from the immunoglobulin superfamily (FIG. 13). Both IgGs exhibited binding signals at 10 µg/ml to CD47-Fc (human, cyno and mouse all >2.0 OD450 nm), and no detectable binding (OD450 nm<0.1) against any other protein. In the 'Developability' ELISA analyses shown in FIG. 14, the positive control antibodies exhibited the expected strong reactivity to all 3 substrates, while the negative control showed low reactivity. Importantly, both A-D5.4 and A-D5.16 IgG1null lead proteins showed binding the negative control against all 3 substrates. This finding underlined the maintenance of highly specific, target-driven binding in the optimised clones A-D5, A-D5.4 and A-D5.16.

Finally, the A-D5 derivative mutant A-D5.4 and A-D5.16 were examined for their binding to wild type CHO (FIG. 15) and HL60 (FIG. 16) cells by flow cytometry. These analyses confirmed that the original murine v-domains of clone mVH/mVL in either IgG1null or IgG4 format drive strong, concentration-dependent binding to CHO cells, whereas clones A-D5, A-D5.4 and A-D5.16 mediate little or no binding signal in either IgG format (FIG. 15). In contrast, clones mVH/mVL, A-D5, A-D5.4 and A-D5.16 all demonstrated strong binding to human CD47+ HL60 cells (FIG. 16), demonstrating that human CD47 binding at the cell membrane had indeed been retained in our optimized clones, but hamster CD47 reactivity had been ameliorated.

Antibody V-Domain T Cell Epitope Analyses

In silico technologies (Abzena, Ltd.), which are based on identifying the location of T cell epitopes in therapeutic antibodies and proteins, were used for assessing the immunogenicity of both the mVH/mVL and lead antibody v-domains. Analysis of the v-domain sequences was performed with overlapping 9 mer peptides (with each overlapping the last peptide by 8 residues) which were tested against each of the 34 MHC class II allotypes. Each 9 mer was scored based on the potential 'fit' and interactions with the MHC class II molecules. The peptide scores calculated by the software lie between 0 and 1. Peptides that produced a high mean binding score (>0.55 in the iTope™ scoring function) were highlighted and, if >50% of the MHC class II binding peptides (i.e. 17 out of 34 alleles) had a high binding affinity (score>0.6), such peptides were defined as 'high affinity' MHC class II binding peptides which are considered a high risk for containing CD4+ T cell epitopes. Low affinity MHC class II binding peptides bind a high number of alleles (>50%) with a binding score>0.55 (but without a majority>0.6). Further analysis of the sequences was performed using the TCED™. The sequences were used to interrogate the TCED™ by BLAST search in order to identify any high sequence homology between peptides (T cell epitopes) from unrelated proteins/antibodies that stimulated T cell responses in previous in vitro T cell epitope mapping studies performed at Abzena Ltd.

Peptides were grouped into four classes: High Affinity Foreign ('HAF'—high immunogenicity risk), Low Affinity Foreign ('LAF'—lower immunogenicity risk), TCED+ (previously identified epitope in TCED™ database), and Germline Epitope ('GE'—human germline peptide sequence with high MHC Class II binding affinity). Germline Epitope 9 mer peptides are unlikely to have immunogenic potential due to T cell tolerance (i.e. these peptides are recognised as 'self' in the host), as validated by previous studies with a wide range of germline peptides. Importantly, such germline v-domain epitopes (aided further by similar sequences in the human antibody constant regions) also compete for MHC Class II occupancy at the membrane of antigen presenting cells, reducing the risk of foreign peptide presentation being sufficient to achieve the 'activation threshold' required for T cell stimulation. High GE content is therefore a beneficial quality in clinical development of an antibody therapeutic.

Figure 17:
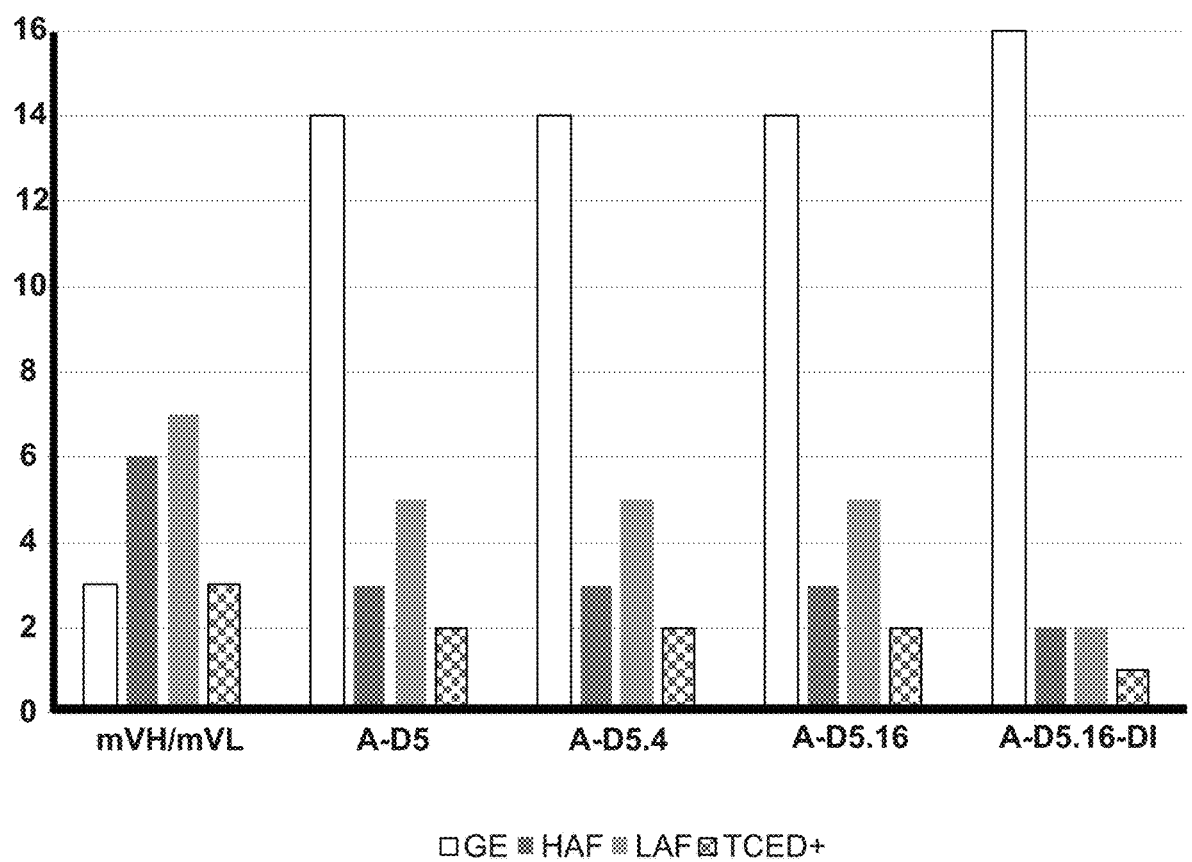
FIG. 17. T cell epitope peptide content in lead antibody v-domains. The v-domains of mVH/mVL, A-D5, A-D5.4 A-D5.16 and A-D5.16-DI antibodies were examined for the presence of Germline (GE), High Affinity Foreign (HAF), Low Affinity Foreign (LAF) and TCED+ T cell receptor epitopes. Both the VH and VL domains of mVH/mVL were found to contain multiple high risk human T cell epitopes and few germline epitopes. In all lead clones, the high risk epitope content was significantly reduced and germline epitope content significantly improved.
Figure 20A:
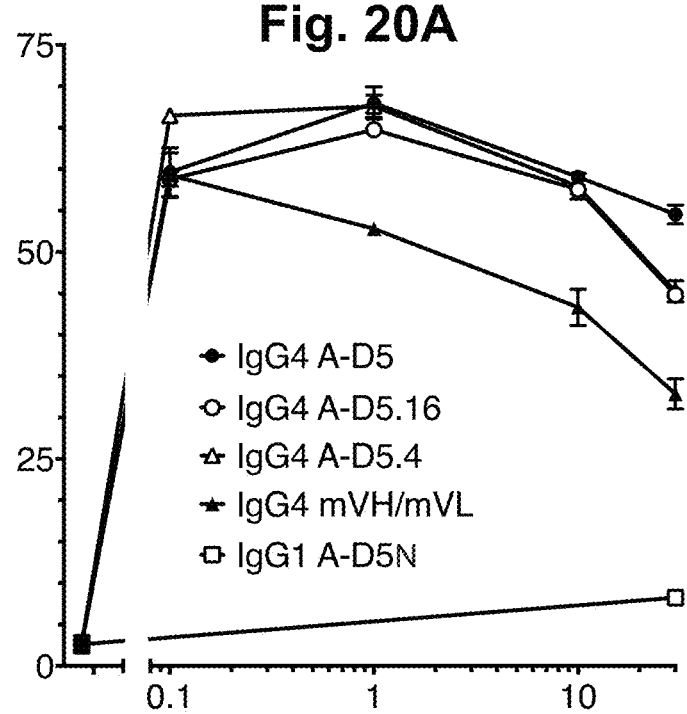
FIG. 20A-FIG. 20B. Flow cytometry phagocytosis analyses.
Figure 20B:
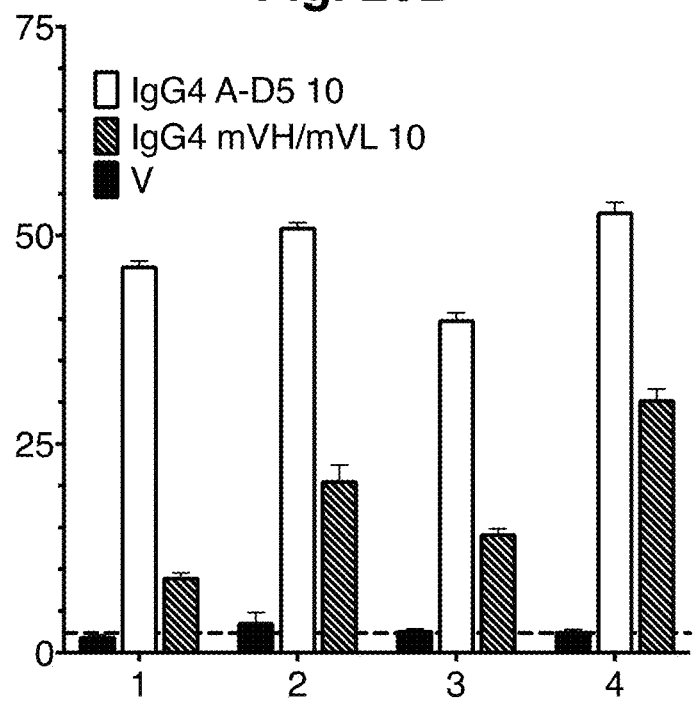

As shown in FIG. 17, key lead v-domains exhibited significant beneficial changes in peptide epitope content in comparison to mVH/mVL. As the v-domain engineering process undertaken here had successfully selected for antibodies that maintained anti-CD47 potency without the need for any murine residues being included in the frameworks (Table 2), multiple HAF and LAF epitopes found in the frameworks of both the heavy and light chain v-domains of mVH/mVL were absent in all library-derived and designer leads (FIG. 17). GE epitope content was also found to be significantly increased (from 3 to ≥14 in all leads), particularly in the VH regions of lead clones where GE content increased from 0 to 9 in all leads, and TCED+ epitopes were reduced from in all leads from 3 to 2 (Table 8). Importantly, however, multiple foreign epitopes were also eliminated by germlining mutations found in the CDRs of lead clones. For example, a TCED+ peptide 'LVHSNGNTY' (SEQ ID NO: 116) found in the LCDR-1 of mVH/mVL (and, therefore, in any forms of VxP037 previously humanized by CDR grafting) was eliminated in the majority of lead clones by the mutation V>L at position 2 and N>Y at position 7 (Tables 4 and 5). Similarly, the LCDR2 from the mVH/mVL sequence encoded for three foreign epitope peptides spanning the VL Framework 2-LCDR2-Framework 3. These included two HAF peptides ('LLIYKVSYR' (SEQ ID NO: 117) and 'YRFSGVPDR' (SEQ ID NO: 118)) and one LAF peptide ('LIYKVSYRF' (SEQ ID NO: 119)). Insertion of the LCDR2 into the human germline framework IGKV2-28 did not fully remove this issue, as the total sequence 'LLIYK-VSYRFSGVPDR' (SEQ ID NO: 120) from mVH/mVL maintains 100% identity in the IGKV2-28 grafted sequence (Table 2). One HAF and two LAF peptides were still found in this region for clones A-D5, A-D5.4 and A-D5.16, while the HAF sequence 'YRFSGVPDR' (SEQ ID NO: 118) was deleted by the mutation Y>N at position 1. Surprisingly however, the LCDR2 sequence KVSNRFS (SEQ ID NO:

85) that had been identified in the functional binding population during library screening (Table 3), and contained the single human germlining mutation Y>N at position 4, was found to fully ameliorate all predicted foreign epitopes in this region (no HAF, LAF or TCED+ peptides predicted), while also generating two further GE sequences (FIG. 18). It was also observed that the lead clones A-D5 and all of its designer derivatives (Tables 4 and 5) retained an HAF peptide 'VGVYYCFQN' (SEQ ID NO: 121) that was also TCED+, spanning the VL Framework 3 and LCDR3 regions. The mutation of V at position 1 of this peptide to A, T or F were all found to disrupt predicted epitope structure and remove the immunogenicity risk of this peptide.

The findings above allowed the design of a maximally deimmunised light chain sequence which was paired with the A-D5.16 VH sequence (Table 4) to form the clone 'A-D5.16-DI'. A-D5.16-DI contained the LCDR sequence 'RSSQSLLHSAGYNYLH' (SEQ ID NO: 82), the LCDR2 sequence 'KVSNRFS' (SEQ ID NO: 85) and the Framework 2-LCDR3 sequence 'AGVYYCFQNTHTPRT' (SEQ ID NO: 122) (Framework 2 residues underlined). This clone was readily expressed in IgG1null format and was found to retain target binding affinity against human, cyno and mouse CD47 (FIG. 18. A-C) comparable to the mVH/mVL IgG (reduced on mouse FIG. 18C). A-D5.16-DI was also found to exhibit improved CD47-SIRPα blockade in comparison to A-D5.16 and comparable blockade to mVH/mVL against human and cyno CD47, slightly reduced on mouse (FIG. 19). These findings thereby led to a deimmunized clone A-D5.4-DI with a light chain design containing the LCDR sequence "RSSQSLLHSNGYTYLH" (SEQ ID NO: 52) (or SSQSLLHSNGYTY [SEQ ID NO: 92]) using the AHo definition), the LCDR2 sequence "KVSNRFS" (SEQ ID NO: 85) and the Framework 2-LCDR3 sequence "AGVYYCFQNTHTPRT" (SEQ ID NO: 122) (Framework 2 residues underlined).

Phagocytosis of Cancer Cells

Studies were performed to examine the relative potency of CD47 blockade in driving the phagocytosis of HL60 human cancer cells by human primary macrophages. As shown in FIG. 20A, in IgG4 (S228P) format—mVH/mVL, A-D5, A-D5.4 and A-D5.16 all drove significant phagocytosis at all concentrations tested. A-D5 in IgG1null format did not show any significant potency at 20 μg/ml, demonstrating the necessity of Fc gamma receptor 1 binding affinity to provoke phagocytosis. Unexpectedly, IgG4 A-D5, A-D5.4 and A-D5.16 all drove significantly more potent phagocytosis at both 1 and 10 μg/ml, when compared to mVH/mVL. This phenomenon was then examined for IgG4 A-D5 and mVH/mVL across 4 separate donors of human macrophage (FIG. 20B). This analysis showed that the higher potency shown in FIG. 20A was correct, with A-D5 being significantly more potent in all donors (FIG. 20B).

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents cited herein are incorporated by reference in their entirety.

TABLE 1

Amino acid sequences murine anti-CD47 CDRs as defined here ("Unified" scheme) in comparison to alternative definitions. SEQ ID NOs are shown in brackets.

| Scheme | HCDR1 | HCDR2 | HCDR3 | LCDR1 | LCDR2 | LCDR3 |
|---|---|---|---|---|---|---|
| Unified | GYTFTNYYVF (4) | IGDINPVNGDTNFNEKFKN (123) | GGYTMDY (5) | RSSQSLVHSNGNTYLH (9) | KVSYRFS (10) | SQNTHVPRT (11) |
| Kabat | NYYVF (124) | DINPVNGDTNFNEKFKN (125) | GGYTMDY (5) | RSSQSLVHSNGNTYLH (9) | KVSYRFS (10) | SQNTHVPRT (11) |
| Chotia | GYTFTNY (126) | NPVNGD (127) | GGYTMDY (5) | RSSQSLVHSNGNTYLH (9) | KVSYRFS (10) | SQNTHVPRT (11) |
| IMGT | GYTFTNYY (128) | INPVNGDT (129) | TRGGYTMDY (130) | QSLVHSNGNTY (131) | KVS | SQNTHVPRT (11) |
| AHo | GSGYTFTNYY (15) | INPVNGDTNFNEKFKN (132) | GGYTMD (16) | SSQSLVHSNGNTY (19) | KVSYRFS (10) | NTHVPR (20) |
| AbM | GYTFTNYYVF (4) | DINPVNGDTN (133) | GGYTMDY (5) | RSSQSLVHSNGNTYLH (9) | KVSYRFS (10) | SQNTHVPRT (11) |
| Contact | TNYYVF (134) | IGDINPVNGDTN (135) | TRGGYTMD (136) | HSNGNTYLHWY (137) | LLIYKVSYRF (138) | SQNTHVPR (139) |

TABLE 2

Amino acid sequence of VXP037 murine anti-CD47 v-domains (mVH/mVL) and human germline CDR grafts (VH1A/L1). SEQ ID NOs are shown in brackets.

| V-DOMAIN | Human germline[1] | Amino acid sequence[2] |
|---|---|---|
| CD47-mVH | n/a | EVQLQQFGAELVKPGASMKLSCKASGYTFTNYYVFWVKQRPGQGLEWIGDINPVNGDTNFNEKFKNKATLTVDKSSTTTYLQLSSLTSEDSAVYYCTRGGYTMDYWGQGTLVTVSS (140) |
| CD47-VH1 | IGHV5-51 | EVQLVQSGAEVKKPGESLKISCKGSGYTFTNYYVFWVRQMPGKGLEWIGDINPVNGDTNFNESFQGQVTISADKSISTAYLQWSSLKASDTAMYYCARGGYTMDYWGQGTLVTVSS (141) |
| CD47-mVL | n/a | DVVMTQTPLSLSVSLGDQASISCRSSQSLVHSNGNTYLHWYLQKPGQSPKLLIYKVSYRFSGVPDRFSGSGSGTDFTLKISRVEAEDLGVYFCSQNTHVPRTFGQGTKVEIK (142) |
| CD47-VL1 | IGKV2-28 | DIVMTQSPLSLPVTPGEPASISCRSSQSLVHSNGNTYLHWYLQKPGQSPQLLIYKVSYRFSGVPDRFSGSGSGTDFTLKISRVEAEDVGVYYCSQNTHVPRTFGQGTKVEIK (143) |

[1]Human germline definitions used for grafting, based on IMGT system.
[2]CDR residues are in bold and underlined. As noted above, the "Unified" CDR definitions used in this manuscript are an expanded definition in comparison to the classical Kabat definition.

TABLE 3

Amino acid sequences of unique CDRs (using Unified definition) from 854 unique anti-CD47 v-domains. SEQ ID NOs are shown in brackets.

| LCDR1 | LCDR2 | LCDR3 | HCDR1 | HCDR2 | HCDR3 |
|---|---|---|---|---|---|
| RSSHSLVHSNGNTYLH (144) | KGSNRAS (67) | FQNTHTPRT (54) | GYNFTMGDINPFNGDGGFTMDY NYYIFTNFNPSFQG (66) (145)(146) | | |
| RSSQSFLHSNGNNYLH (147) | KGSNRFS (47) | LQNTHTPRT (148) | GYRFTMGDINPGDGDGGHTMDY NYYIFTNFNPSFQG (151) (149)(150) | | |
| RSSQSLLHSNGNNYLD (152) | KGSNRSS (153) | MQALHTPWT (154) | GYRFTMGDINPGNGDGGITMDY NYYVFTNFNPSFQG (157) (155)(156) | | |
| RSSQSLLHSNGNNYLH (158) | KGSYRAS (58) | MQALHVPRT (159) | GYSFNMGDINPGNGDGGQTMDQ NYYIFTNYNPSFQG (162) (160)(161) | | |
| RSSQSLLHSNGNTYLD (163) | KGSYRFS (63) | MQALQVPWT (164) | GYSFTMGDINPGNGDGGYIMDY NYYIFTNYSPSFQG (166) (43) (165) | | |
| RSSQSLLHSNGNTYLH (167) | KGSYRLS (168) | MQATHVPWT (169) | GYSFTMGDINPGNGDGGYTADY SYYIFTRFNPSFQG (172) (170)(171) | | |
| RSSQSLLHSNGSNYLH (173) | KVSNRAS (174) | MQATQVPWT (175) | GYSFTMGDINPGNGDGGYTLDY SYYIVTRFSPSFQG (178) (176)(177) | | |
| RSSQSLLHSNGYNYLH (46) | KVSNRFS (85) | MQNLQTPRT (179) | GYSFTMGDINPGNGDGGYTMDA SYYVFTRYNPSFQG (182) (180)(181) | | |
| RSSQSLLHSNGYTYLD (183) | KVSNRLS (53) | MQNTHIPRT (184) | GYSFTMGDINPGNGDGGYTMDE SYYVGTRYSPSFQG (187) (185)(186) | | |
| RSSQSLLHSNGYTYLH (52) | KVSYRAS (188) | MQNTHTLRT (189) | GYTFTMGDINPGNSDGGYTMDF NYYIFTNFNPSFQG (191) (49) (190) | | |
| RSSQSLVHSNGNNYLD (192) | KVSYRLS (193) | MQNTHTPRT (194) | GYTFTMGDINPGNSDGGYTMDH SYYIFTNYNPSFQG (197) (195)(196) | | |
| RSSQSLVHSNGNNYLH (201) | LGSNRAS (72) | MQNTHVPRT (198) | GYTFTMGDINPVDGDGGYTMDI SYYVFTKYNPSFQG (70) (199)(200) | | |
| RSSQSLVHSNGNTYLD (62) | LGSNRFS (71) | MQNTQTPRT (202) | | | MGDINPVDGDGGYTMDK TNFNPSFQG (56) (203) |
| RSSQSLVHSNGYNYLH (207) | LGSNRLS (77) | MQTTHTPRT (204) | | | MGDINPVDGDGGYTMDL TNFSPSFQG (206) (205) |
| RSSQSLVHSNGYTYLD (212) | LGSYRAS (208) | MQTTQIPRT (209) | | | MGDINPVDGDGGYTMDM TNYNPSFQG (211) (210) |
| RSSQSLVHSNGYTYLH (57) | LGSYRFS (213) | SQATHFPRT (214) | | | MGDINPVDGDGGYTMDN TNYSPSFQG (216) (215) |
| | LGSYRLS (217) | SQATQTPRT (73) | | | MGDINPVDGDGGYTMDQ TRFNPSFQG (219) (218) |
| | LVSNRAS (220) | SQNIQTPRT (221) | | | MGDINPVDGDGGYTMDR TRYNPSFQG (51) (222) |
| | PVSNRFS (223) | SQNLHTPRT (224) | | | MGDINPVDGDGGYTMDT TRYSPSFQG (226) (225) |
| | LVSNRLS (227) | SQNLQTPRT (228) | | | MGDINPVDSDGGYTMDV TKFNPSFQG (230) (229) |
| | LVSYRAS (231) | SQNMHTPRT (232) | | | MGDINPVDSDGGYMDW TNFNPSFQG (234) (233) |
| | MGSNRFS (235) | SQNTHFPRT (236) | | | MGDINPVDSDGGYMGK TNYNPSFQG (61) (237) |
| | MGSYRLS (238) | SQNTHVPWT (239) | | | MGDINPVDSDGGYTPDY TNYSPSFQG (45) (240) |
| | MVSNRFS (241) | SQNTQAPRT (242) | | | MGDINPVDSDGGYTRDY TRFNPSFQG (244) (243) |
| | | SQNTQTPRT (59) | | | MGDINPVDSDGGYTTDS TRYNPSFQG (246) (245) |
| | | SQNTQTPWT (247) | | | MGDINPVDSDGGYTTDW TRYSPSFQG (249) (248) |
| | | SQNTQVPRT (250) | | | MGDINPVNGDGGYTTDY TKYNPSFQG (252) (251) |
| | | SQSTHVPRT (253) | | | MGDINPVNGDGGYVMDY TNFSPSFQG (255) (254) |
| | | SQTTHIPRT (256) | | | MGDINPVNGD TNYNPSFQG (257) |
| | | SQTTHVPRT (258) | | | MGDINPVNGD TNYSPSFQG (44) |
| | | SQTTQTPRT (259) | | | MGDINPVNGD TRFNPSFQG (260) |
| | | TQNTHTPRT (261) | | | MGDINPVNGD TRFSPSFQG (262) |
| | | VQNTQVPRT (263) | | | MGDINPVNGD TRYNPSFQG (264) |
| | | | | | MGDINPVNGD TRYSPSFQG (265) |
| | | | | | MGDINPVNSD TKYNPSFQG (266) |
| | | | | | MGDINPVNSD TNFNPSFQG (267) |
| | | | | | MGDINPVNSD TNYSPSFQG (268) |

TABLE 3-continued

Amino acid sequences of unique CDRs (using Unified definition) from 854 unique anti-CD47 v-domains. SEQ ID NOs are shown in brackets.

| LCDR1 | LCDR2 | LCDR3 | HCDR1 | HCDR2 | HCDR3 |
|---|---|---|---|---|---|
| | | | | MGDINPVNSD TRFNPSFQG (269) | |
| | | | | MGDINPVNSD TRFSPSFQG (270) | |
| | | | | MGDINPVNSD TRYNPSFQG (271) | |
| | | | | MGDINPVNSD TRYSPSFQG (272) | |
| | | | | MGDIYPGNSD TKYNPSFQG (273) | |
| | | | | MGDIYPVNGD TRYNPSFQG (274) | |
| | | | | MGIINPGNGD TRYNPSFQG (275) | |
| | | | | MGIINPVDGD TKYNPSFQG (276) | |
| | | | | MGIINPVDGD TNYSPSFQG (277) | |
| | | | | MGIINPVDGD TRFNPSFQG (278) | |
| | | | | MGIINPVDGD TRFSPSFQG (279) | |
| | | | | MGIINPVDGD TRYNPSFQG (74) | |
| | | | | MGIINPVDGD TRYSPSFQG (65) | |
| | | | | MGIINPVDSD TNYNPSFQG (280) | |
| | | | | MGIINPVDSD TRFNPSFQG (281) | |
| | | | | MGIINPVDSD TRYNPSFQG (282) | |
| | | | | MGIINPVDSD TRYSPSFQG (283) | |
| | | | | MGIINPVNGD TKFNPSFQG (284) | |
| | | | | MGIINPVNGD TKYNPSFQG (285) | |
| | | | | MGIINPVNGD TKYSPSFQG (286) | |
| | | | | MGIINPVNGD TNFNPSFQG (287) | |
| | | | | MGIINPVNGD TNFSPSFQG (288) | |
| | | | | MGIINPVNGD TNYNPSFQG (60) | |
| | | | | MGIINPVNGD TNYSPSFQG (289) | |
| | | | | MGIINPVNGD TRFNPSFQG (290) | |
| | | | | MGIINPVNGD TRFSPSFQG (291) | |
| | | | | MGIINPVNGD TRYNPSFQG (292) | |
| | | | | MGIINPVNGD TRYSPSFQG (293) | |
| | | | | MGIINPVNSD TKYNPSFQG (294) | |
| | | | | MGIINPVNSD TNFNPSFQG (295) | |
| | | | | MGIINPVNSD TNYSPSFQG (296) | |
| | | | | MGIINPVNSD TRFSPSFQG (297) | |
| | | | | MGIINPVNSD TRYNPSFQG (298) | |
| | | | | MGIINPVNSD TRYSPSFQG (299) | |
| | | | | MGNINPVDGD TRYNPSFQG (300) | |
| | | | | MGVINPVNSD TNYNPSFQG (301) | |

TABLE 4

Amino acid sequences of CDRs (using Unified definition) of unique, library-derived and designer, CD47-SIRPα interaction-blocking anti-CD47 IgGs. SEQ ID NOs are shown in brackets.

| Clone name | LCDR1 | LCDR2 | LCDR3 | HCDR1 | HCDR2 | HCDR3 |
|---|---|---|---|---|---|---|
| D-H3 | RSSQSLLH SNGYNYLH (46) | KGSNRFS (48) | SQNLHGYSFTMGI VPRT (43) | DINPVNGDGGYTPDY (44) | | NYYIFTNYSPSFQG (45) |
| A-D5 | RSSQSLLH SNGYTYLH (52) | KVSNRLS (54) | FQNTHGYTFTMGI TPRT (43) | INPVDGDGGYTMDR (50) | | NYYIFTNYNPSFQG (51) |
| G-B6 | RSSQSLVH SNGYTYLH (57) | KGSYRAS (59) | SQNTQGYSFTIGI TPRT (43) | DINPVNGDGGYTMDK (55) | | NYYIFTNFSPSFQG (56) |
| F-E7 | RSSQSLVH SNGNTYLD (62) | KGSYRFS (64) | SQATHGYSFTMGI TPRT (43) | INPVNGDGGYTMGK (60) | | NYYIFTNYSPSFQG (61) |
| VH-A1/VL-B1 | RSSQSLLH SNGYNYLH (46) | KGSNRAS (67) | SQNTHGYSFTMGI TPRT (43) | INPVDGDGGFTMDY (65) | | NYYIFTRYSPSFQG (66) |
| MH | RSSQSLLH SNGYNYLH (46) | LGSNRFS (71) | SQNTQGYSFTIGI TPRT (43) | INPVDGDGGYTMDI (69) | | NYYIFTRYSPSFQG (70) |
| TTP | RSSQSLLH SNGYNYLH (46) | LGSNRAS (72) | SQATQGYSFTMGI TPRT (43) | INPVDGDGGYTMDI (65) | | NYYIFTRYSPSFQG (70) |
| A-D5.1 | RSSQSLLH SNGYTYLH (52) | KVSNRLS (54) | FQNTHGYSFTMGI TPRT (43) | INPVDGDGGYTMDR (50) | | NYYIFTNYNPSFQG (51) |
| A-D5.2 | RSSQSLLH SNGYTYLH (52) | KVSNRLS (54) | FQNTHGYSFTMGI TPRT (43) | INPVDGDGGYTMDR (74) | | NYYIFTRYNPSFQG (51) |
| A-D5.3 | RSSQSLLH SNGYTYLH (52) | KVSNRLS (54) | FQNTHGYSFTMGI TPRT (43) | INPVDGDGGYTMDR (65) | | NYYIFTRYSPSFQG (51) |
| A-D5.4 | RSSQSLLH SNGYNYLH (46) | KVSNRLS (54) | FQNTHGYTFTMGI TPRT (43) | INPVDGDGGYTMDR (50) | | NYYIFTNYNPSFQG (51) |
| A-D5.5 | RSSQSLLH SNGYNYLH (46) | KGSNRLS (75) | FQNTHGYTFTMGI TPRT (43) | INPVDGDGGYTMDR (50) | | NYYIFTNYNPSFQG (51) |
| A-D5.6 | RSSQSLLH SNGYNYLH (46) | KGSNRLS (75) | FQNTQGYTFTMGI TPRT (43) | INPVDGDGGYTMDR (50) | | NYYIFTNYNPSFQG (76) |
| A-D5.7 | RSSQSLLH SNGYNYLH (46) | LGSNRLS (77) | FQNTQGYTFTMGI TPRT (43) | INPVDGDGGYTMDR (50) | | NYYIFTNYNPSFQG (76) |
| A-D5.8 | RSSQSLLH SQGYTYLH (78) | KVSNRLS (53) | FQNTHGYTFTMGI TPRT (43) | INPVDGDGGYTMDR (50) | | NYYIFTNYNPSFQG (49) |
| A-D5.9 | RSSQSLLH SNGYTYLH (52) | KVSNRLS (53) | FQQTHGYTFTMGI TPRT (43) | INPVDGDGGYTMDR (50) | | NYYIFTNYNPSFQG (49) |
| A-D5.10 | RSSQSLLH SQGYTYLH (78) | KVSNRLS (53) | FQQTHGYTFTMGI TPRT (43) | INPVDGDGGYTMDR (50) | | NYYIFTNYNPSFQG (49) |

TABLE 5

Amino acid sequences of CDRs (using Unified definition) of unique, A-D5-derived, CD47-SIRPα interaction-blocking, designer anti-CD47 IgGs. SEQ ID NOs are shown in brackets.

| Clone name | LCDR1 | LCDR2 | LCDR3 | HCDR1 | HCDR2 | HCDR3 |
|---|---|---|---|---|---|---|
| A-D5.11 | RSSQSLLH SNGYNYLH (46) | KVSNRLS (53) | FQNTHGYSFTMGI TPRT (43) | INPVDGDGGYTMDR (50) | | NYYIFTNYNPSFQG (51) |
| A-D5.12 | RSSQSLLH SNGYNYLH (46) | KVSNRLS (53) | FQNTHGYSFTMGI TPRT (43) | INPVDGDGGYTMDR (74) | | NYYIFTRYNPSFQG (51) |
| A-D5.13 | RSSQSLLH SNGYNYLH (46) | KVSNRLS (53) | FQNTHGYSFTMGI TPRT (43) | INPVDGDGGYTMDR (65) | | NYYIFTRYSPSFQG (51) |
| A-D5.14 | RSSQSLLH SSGYNYLH (80) | KVSNRLS (53) | FQNTHGYSFTMGI TPRT (43) | INPVDGDGGYTMDR (65) | | NYYIFTRYSPSFQG (51) |
| A-D5.15 | RSSQSLLH SGGYNYLH (81) | KVSNRLS (53) | FQNTHGYSFTMGI TPRT (43) | INPVDGDGGYTMDR (65) | | NYYIFTRYSPSFQG (51) |
| A-D5.16 | RSSQSLLH SAGYNYLH (82) | KVSNRLS (53) | FQNTHGYSFTMGI TPRT (43) | INPVDGDGGYTMDR (65) | | NYYIFTRYSPSFQG (51) |
| A-D5.17 | RSSQSLLH STGYNYLH (83) | KVSNRLS (53) | FQNTHGYSFTMGI TPRT (43) | INPVDGDGGYTMDR (65) | | NYYIFTRYSPSFQG (51) |
| A-D5.18 | RSSQSLLH SNAYNYLH (84) | KVSNRLS (53) | FQNTHGYSFTMGI TPRT (43) | INPVDGDGGYTMDR (65) | | NYYIFTRYSPSFQG (51) |

The invention claimed is:

1. An antibody molecule that specifically binds to human Integrin Associated Protein (CD47) and cynomolgus monkey CD47, or an antigen-binding portion thereof, wherein the antibody molecule or antigen-binding portion comprises:
   (a) a heavy chain variable region comprising a heavy chain complementarity determining region (HCDR) 1 of SEQ ID NO: 49, a HCDR2 of SEQ ID NO: 50, and a HDCR3 of SEQ ID NO: 51; and a light chain variable region comprising a light chain complementarity determining region (LCDR) 1 of SEQ ID NO: 52, a LCDR2 of SEQ ID NO: 53, and a LDCR3 of SEQ ID NO: 54; or
   (b) a heavy chain variable region comprising a HCDR1 of SEQ ID NO: 49, a HCDR2 of SEQ ID NO: 50, and a HDCR3 of SEQ ID NO: 51; and a light chain variable region comprising a LCDR1 of SEQ ID NO: 52, a LCDR2 of SEQ ID NO: 85, and a LDCR3 of SEQ ID NO: 54.

2. The antibody molecule or antigen-binding portion of claim 1, wherein the antibody molecule or antigen-binding portion is humanized or chimeric.

3. The antibody molecule or antigen-binding portion of claim 1, wherein the heavy chain variable region, the light chain variable region, or both the heavy chain variable region and the light chain variable region comprise a human variable domain framework scaffold into which the CDRs have been inserted.

4. The antibody molecule or antigen-binding portion of claim 1, wherein the heavy chain variable region comprises an IGHV5-51 human germline scaffold into which the HCDR1, HCDR2 and HCDR3 sequences have been inserted.

5. The antibody molecule or antigen-binding portion of claim 1, wherein the light chain variable region comprises an IGKV2-28 human germline scaffold into which the LCDR1, LCDR2 and LCDR3 sequences have been inserted.

6. The antibody molecule or antigen-binding portion of claim 1, wherein the antibody molecule or antigen-binding portion comprises an immunologically inert constant region.

7. The antibody molecule or antigen-binding portion of claim 1, wherein the antibody molecule or antigen-binding portion is a Fab fragment, a F(ab)$_2$ fragment, an Fv fragment, a tetrameric antibody, a tetravalent antibody, a multispecific antibody or an scFv.

8. The antibody molecule or antigen-binding portion of claim 7, wherein the multispecific antibody is a bivalent antibody.

9. The antibody molecule or antigen-binding portion of claim 1, wherein the antibody molecule or antigen-binding portion specifically binds to mouse CD47.

10. A pharmaceutical composition comprising the antibody molecule or antigen-binding portion of claim 1 and a pharmaceutically acceptable excipient, carrier, buffer or stabilizer.

* * * * *